US010046040B2

(12) United States Patent
Galen

(10) Patent No.: US 10,046,040 B2
(45) Date of Patent: Aug. 14, 2018

(54) **MULTIVALENT LIVE VECTOR VACCINE AGAINST *CLOSTRIDIUM DIFFICILE*-ASSOCIATED DISEASE**

(75) Inventor: James E. Galen, Sykesville, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 150 days.

(21) Appl. No.: 13/509,818

(22) PCT Filed: Nov. 16, 2010

(86) PCT No.: PCT/US2010/056871

§ 371 (c)(1), (2), (4) Date: May 15, 2012

(87) PCT Pub. No.: WO2011/060431

PCT Pub. Date: May 19, 2011

(65) Prior Publication Data

US 2012/0282293 A1 Nov. 8, 2012

Related U.S. Application Data

(60) Provisional application No. 61/261,406, filed on Nov. 16, 2009.

(51) Int. Cl.

| | |
|---|---|
| ***A61K 39/08*** | (2006.01) |
| ***A61P 31/04*** | (2006.01) |
| ***A61P 37/04*** | (2006.01) |
| *A61K 39/00* | (2006.01) |

(52) U.S. Cl.

CPC ........ *A61K 39/08* (2013.01); *A61K 2039/522* (2013.01); *A61K 2039/523* (2013.01); *A61K 2039/541* (2013.01); *A61K 2039/545* (2013.01); *A61K 2039/55505* (2013.01)

(58) Field of Classification Search

None

See application file for complete search history.

(56) References Cited

U.S. PATENT DOCUMENTS

| | | | | |
|---|---|---|---|---|
| 6,413,768 | B1 | 7/2002 | Galen | |
| 6,703,233 | B1 | 3/2004 | Galen | |
| 6,969,513 | B2 | 11/2005 | Galen | |
| 6,977,176 | B2 | 12/2005 | Galen | |
| 7,056,700 | B2 | 6/2006 | Galen | |
| 7,125,720 | B2 | 10/2006 | Galen | |
| 7,138,112 | B2 | 11/2006 | Galen | |
| 7,141,408 | B2 | 11/2006 | Galen | |
| 7,459,161 | B2 | 12/2008 | Galen | |
| 8,076,130 | B2 | 12/2011 | Galen | |
| 8,137,930 | B2 | 3/2012 | Vindurampulle et al. | |
| 8,206,940 | B2 * | 6/2012 | Feng et al. | 435/7.32 |
| 2002/0146430 | A1 * | 10/2002 | Galen | 424/200.1 |

OTHER PUBLICATIONS

Greenspan et al. (Nature Biotechnology 7: 936-937, 1999).*
Pituch et al. (Journal of Medical Microbiology, vol. 54, pp. 143-147).*
Bowie et al. (Science, 1990, 257:1306-1310).*
Galen et al., Adaptation of the Endogenous *Salmonella enterica* Serovar Typhi clyA-Encoded Hemolysin for Antigen Export Enhances the Immunogenicity of Anthrax Protective Antigen Domain 4 Expressed by the Attenuated Live-Vector Vaccine Strain CVD 908-htrA, Infection and Immunity, 72:7096-7106 (2004), American Society for Microbiology, Washington, D.C.
Galen et al., A New Generation of Stable, Nonantibiotic, Low-Copy-Number Plasmids Improves Immune Responses to Foreign Antigens in *Salmonella enterica* Serovar Typhi Live Vectors, Infection and Immunity,78:337-347 (Nov. 2009), American Society for Microbiology, Washington, D.C.
Ward et al., Immunogenicity of a *Salmonella typhimurium* aroA aroD Vaccine Expressing a Nontoxic Domain of Clostridium difficile Toxin A, Infection and Immunity, 67:2145-2152 (1999), American Society for Microbiology, Washington, D.C.
Schwan et al., Clostridium difficile Toxin CDT Induces Formation of Microtubule-Based Protrusions and Increases Adherence of Bacteria, PLOS Pathogens, 5:e1000626 (Oct. 2009), Public Library of Science, San Francisco, California.

* cited by examiner

*Primary Examiner* — Robert A Zeman

(74) *Attorney, Agent, or Firm* — Nevrivy Patent Law Group P.L.L.C.

(57) ABSTRACT

The invention relates to a multivalent *Clostridium difficile* vaccine comprising a *Salmonella Typhi* live vector comprising the cell binding domain of TcdA toxin (CBD/A) of *Clostridium difficile* or an antigenic fragment thereof and the cell binding domain of TcdB toxin (CBD/B) of *Clostridium difficile* or an antigenic fragment thereof and optionally the cell-binding subunit component (CdtB) of binary toxin of *Clostridium difficile* or an antigenic fragment thereof. The invention further provides methods of inducing an immune response and methods of preventing recurrence of *C. difficile* infections in subjects.

11 Claims, 10 Drawing Sheets

SEQUENCE LISTING

```
<160> NUMBER OF SEQ ID NOS: 19

<210> SEQ ID NO 1
<211> LENGTH: 996
<212> TYPE: DNA
<213> ORGANISM: artificial
```

-continued

<220> FEATURE:
<223> OTHER INFORMATION: synthetic

<400> SEQUENCE: 1
tagtaatgaa tggctagcac cggctatacg agcatcaacg ggaagcattt ttatttcaat 60
accgacggca ttatgcagat cggggtgttc aaagggccca acggtttcga atactttgcg 120
ccggccaaca cggatgcgaa taacatcgaa ggtcaagcca tcctctacca gaacaaattc 180
ctgaccctca atggcaagaa atattacttc gggtccgaca gcaaggctgt cacgggtctg 240
cgcacgattg atgggaaaaa gtattacttc aacaccaata ctgccgtggc ggtcaccgga 300
tggcaaacga tcaacggcaa gaaatactac ttcaatacca acacgtccat tgcctcgacc 360
gggtatacga tcatttccgg caaacacttc tacttcaaca ccgacgggat catgcaaatc 420
ggtgtgttta aagggcccga tggcttcgag tactttgccc cggcgaatac ggacgccaat 480
aacattgaag gtcaggcaat tcggtatcag aatcgttttc tctatctgca tgacaacatc 540
tactatttcg gtaataacag caaggcggcc accgggtggg tcacgattga tggcaaccgg 600
tattacttcg agcccaatac ggcgatgggg gcgaatggtt ataaaacgat cgacaacaag 660
aatttctact ttcgcaacgg gctcccgcag attggcgtgt tcaaagggtc caacggcttt 720
gagtacttcg cccccgcgaa tacggatgcc aacaatatcg agggccaagc gattcggtat 780
caaaaccgct tcctccacct gctcgggaaa atctattact tcggcaataa ctcgaaagcc 840
gtcacgggtt ggcaaacgat taatggcaaa gtgtattact tcatgccgga tactgcaatg 900
gcagccgctg gtggattatt cgaaattgac ggcgtcatct atttctttgg cgtggatggg 960
gtcaaagccc cggggatcta tggctaatga cctagg 996

<210> SEQ ID NO 2
<211> LENGTH: 325
<212> TYPE: PRT
<213> ORGANISM: artificial
<220> FEATURE:
<223> OTHER INFORMATION: synthetic

<400> SEQUENCE: 2

Met Ala Ser Thr Gly Tyr Thr Ser Ile Asn Gly Lys His Phe Tyr Phe
1               5                   10                  15

Asn Thr Asp Gly Ile Met Gln Ile Gly Val Phe Lys Gly Pro Asn Gly
            20                  25                  30

Phe Glu Tyr Phe Ala Pro Ala Asn Thr Asp Ala Asn Asn Ile Glu Gly
        35                  40                  45

Gln Ala Ile Leu Tyr Gln Asn Lys Phe Leu Thr Leu Asn Gly Lys Lys
    50                  55                  60

Tyr Tyr Phe Gly Ser Asp Ser Lys Ala Val Thr Gly Leu Arg Thr Ile
65                  70                  75                  80

Asp Gly Lys Lys Tyr Tyr Phe Asn Thr Asn Thr Ala Val Ala Val Thr
                85                  90                  95

Gly Trp Gln Thr Ile Asn Gly Lys Lys Tyr Tyr Phe Asn Thr Asn Thr
            100                 105                 110

Ser Ile Ala Ser Thr Gly Tyr Thr Ile Ile Ser Gly Lys His Phe Tyr
        115                 120                 125

Phe Asn Thr Asp Gly Ile Met Gln Ile Gly Val Phe Lys Gly Pro Asp
    130                 135                 140

Gly Phe Glu Tyr Phe Ala Pro Ala Asn Thr Asp Ala Asn Asn Ile Glu
145                 150                 155                 160

-continued

```
Gly Gln Ala Ile Arg Tyr Gln Asn Arg Phe Leu Tyr Leu His Asp Asn
                165                 170                 175

Ile Tyr Tyr Phe Gly Asn Asn Ser Lys Ala Ala Thr Gly Trp Val Thr
            180                 185                 190

Ile Asp Gly Asn Arg Tyr Tyr Phe Glu Pro Asn Thr Ala Met Gly Ala
        195                 200                 205

Asn Gly Tyr Lys Thr Ile Asp Asn Lys Asn Phe Tyr Phe Arg Asn Gly
    210                 215                 220

Leu Pro Gln Ile Gly Val Phe Lys Gly Ser Asn Gly Phe Glu Tyr Phe
225                 230                 235                 240

Ala Pro Ala Asn Thr Asp Ala Asn Asn Ile Glu Gly Gln Ala Ile Arg
                245                 250                 255

Tyr Gln Asn Arg Phe Leu His Leu Leu Gly Lys Ile Tyr Tyr Phe Gly
            260                 265                 270

Asn Asn Ser Lys Ala Val Thr Gly Trp Gln Thr Ile Asn Gly Lys Val
        275                 280                 285

Tyr Tyr Phe Met Pro Asp Thr Ala Met Ala Ala Ala Gly Gly Leu Phe
    290                 295                 300

Glu Ile Asp Gly Val Ile Tyr Phe Phe Gly Val Asp Gly Val Lys Ala
305                 310                 315                 320

Pro Gly Ile Tyr Gly
                325
```

<210> SEQ ID NO 3
<211> LENGTH: 1629
<212> TYPE: DNA
<213> ORGANISM: artificial
<220> FEATURE:
<223> OTHER INFORMATION: synthetic

<400> SEQUENCE: 3

```
tagtaatgaa tggctagcgg cctgatctat attaacgatt cactgtacta tttcaagccg     60

cccgtcaata acctcatcac cgggtttgtg acggtcggcg acgataaata ctacttcaat    120

ccgatcaacg gcggagccgc gagcattggg gagaccatca ttgatgacaa gaattattac    180

ttcaaccaga gtggcgtgct gcagacgggg gtcttcagta ccgaggacgg ctttaaatac    240

ttcgcccccg cgaatacgct cgatgagaac ctggaagggg aggcgattga ctttaccggc    300

aagctgatca ttgacgagaa catctactat ttcgatgaca attaccgcgg ggccgtggaa    360

tggaaggagc tcgatggcga gatgcactat tttagcccgg agacggggaa agctttcaaa    420

ggcctgaatc aaattgggga ctacaagtat tacttcaact ctgacggtgt gatgcagaag    480

gggttcgtga gtatcaatga caacaagcat tatttcgacg attctggcgt catgaaagtg    540

gggtacaccg agatcgatgg caagcacttc tactttgccg agaatggtga gatgcaaatc    600

ggcgtgttca atacggaaga cgggtttaag tatttcgcgc atcataacga ggatctcggc    660

aatgaagagg gcgaagagat ctcatattcc ggaatcctca acttcaataa caagatttac    720

tactttgatg actcatttac cgccgtggtc ggctggaagg acctcgagga tgggtcaaag    780

tactatttcg acgaggatac ggcggaggcc tacatcggcc tgtcattaat caacgacggc    840

cagtattact ttaatgatga cggcatcatg caggtcgggt ttgtcaccat caacgataaa    900

gtcttctact tctctgactc tggcattatc gagagcgggg tgcagaacat cgacgataac    960

tatttctaca tcgatgacaa tggcattgtc cagatcggcg tgttcgatac gtcagacggt   1020

tataagtatt ttgcgcccgc caacaccgtc aacgataata tctacggtca agctgttgaa   1080
```

-continued

```
tatagtggtt tggtccgtgt cggtgaagac gtgtactatt tcggcgagac gtacacaatt   1140

gagacgggct ggatctatga tatggagaac gagagtgaca agtactattt caatcctgag   1200

accaagaaag catgcaaggg gatcaacctg atcgatgaca tcaagtacta tttcgacgag   1260

aagggcatta tgcgcacggg gcttatctca tttgagaata acaattatta cttcaatgag   1320

aacggggaaa tgcagtttgg gtacatcaat attgaggaca agatgttcta ttttggcgag   1380

gatggcgtca tgcagatcgg ggtgttcaac accccagatg gtttcaagta tttcgcgcat   1440

cagaatacgc tggatgagaa cttcgagggc gaatcaatca actataccgg gtggctggac   1500

ctcgatgaga agcgctacta tttcacggac gaatacattg cggccaccgg ctcagtcatc   1560

attgatggcg aggaatacta tttcgaccct gatacggcgc agctggtgat cagtgagtaa   1620

tgacctagg                                                           1629
```

```
<210> SEQ ID NO 4
<211> LENGTH: 536
<212> TYPE: PRT
<213> ORGANISM: artificial
<220> FEATURE:
<223> OTHER INFORMATION: synthetic

<400> SEQUENCE: 4

Met Ala Ser Gly Leu Ile Tyr Ile Asn Asp Ser Leu Tyr Tyr Phe Lys
1               5                   10                  15

Pro Pro Val Asn Asn Leu Ile Thr Gly Phe Val Thr Val Gly Asp Asp
            20                  25                  30

Lys Tyr Tyr Phe Asn Pro Ile Asn Gly Gly Ala Ala Ser Ile Gly Glu
        35                  40                  45

Thr Ile Ile Asp Asp Lys Asn Tyr Tyr Phe Asn Gln Ser Gly Val Leu
    50                  55                  60

Gln Thr Gly Val Phe Ser Thr Glu Asp Gly Phe Lys Tyr Phe Ala Pro
65                  70                  75                  80

Ala Asn Thr Leu Asp Glu Asn Leu Glu Gly Glu Ala Ile Asp Phe Thr
                85                  90                  95

Gly Lys Leu Ile Ile Asp Glu Asn Ile Tyr Tyr Phe Asp Asp Asn Tyr
            100                 105                 110

Arg Gly Ala Val Glu Trp Lys Glu Leu Asp Gly Glu Met His Tyr Phe
        115                 120                 125

Ser Pro Glu Thr Gly Lys Ala Phe Lys Gly Leu Asn Gln Ile Gly Asp
    130                 135                 140

Tyr Lys Tyr Tyr Phe Asn Ser Asp Gly Val Met Gln Lys Gly Phe Val
145                 150                 155                 160

Ser Ile Asn Asp Asn Lys His Tyr Phe Asp Asp Ser Gly Val Met Lys
                165                 170                 175

Val Gly Tyr Thr Glu Ile Asp Gly Lys His Phe Tyr Phe Ala Glu Asn
            180                 185                 190

Gly Glu Met Gln Ile Gly Val Phe Asn Thr Glu Asp Gly Phe Lys Tyr
        195                 200                 205

Phe Ala His His Asn Glu Asp Leu Gly Asn Glu Glu Gly Glu Glu Ile
    210                 215                 220

Ser Tyr Ser Gly Ile Leu Asn Phe Asn Asn Lys Ile Tyr Tyr Phe Asp
225                 230                 235                 240

Asp Ser Phe Thr Ala Val Val Gly Trp Lys Asp Leu Glu Asp Gly Ser
                245                 250                 255

Lys Tyr Tyr Phe Asp Glu Asp Thr Ala Glu Ala Tyr Ile Gly Leu Ser
```

-continued

```
            260                 265                 270

Leu Ile Asn Asp Gly Gln Tyr Tyr Phe Asn Asp Asp Gly Ile Met Gln
        275                 280                 285

Val Gly Phe Val Thr Ile Asn Asp Lys Val Phe Tyr Phe Ser Asp Ser
    290                 295                 300

Gly Ile Ile Glu Ser Gly Val Gln Asn Ile Asp Asp Asn Tyr Phe Tyr
305                 310                 315                 320

Ile Asp Asp Asn Gly Ile Val Gln Ile Gly Val Phe Asp Thr Ser Asp
                325                 330                 335

Gly Tyr Lys Tyr Phe Ala Pro Ala Asn Thr Val Asn Asp Asn Ile Tyr
            340                 345                 350

Gly Gln Ala Val Glu Tyr Ser Gly Leu Val Arg Val Gly Glu Asp Val
        355                 360                 365

Tyr Tyr Phe Gly Glu Thr Tyr Thr Ile Glu Thr Gly Trp Ile Tyr Asp
    370                 375                 380

Met Glu Asn Glu Ser Asp Lys Tyr Tyr Phe Asn Pro Glu Thr Lys Lys
385                 390                 395                 400

Ala Cys Lys Gly Ile Asn Leu Ile Asp Asp Ile Lys Tyr Tyr Phe Asp
                405                 410                 415

Glu Lys Gly Ile Met Arg Thr Gly Leu Ile Ser Phe Glu Asn Asn Asn
            420                 425                 430

Tyr Tyr Phe Asn Glu Asn Gly Glu Met Gln Phe Gly Tyr Ile Asn Ile
        435                 440                 445

Glu Asp Lys Met Phe Tyr Phe Gly Glu Asp Gly Val Met Gln Ile Gly
    450                 455                 460

Val Phe Asn Thr Pro Asp Gly Phe Lys Tyr Phe Ala His Gln Asn Thr
465                 470                 475                 480

Leu Asp Glu Asn Phe Glu Gly Glu Ser Ile Asn Tyr Thr Gly Trp Leu
                485                 490                 495

Asp Leu Asp Glu Lys Arg Tyr Tyr Phe Thr Asp Glu Tyr Ile Ala Ala
            500                 505                 510

Thr Gly Ser Val Ile Ile Asp Gly Glu Glu Tyr Tyr Phe Asp Pro Asp
        515                 520                 525

Thr Ala Gln Leu Val Ile Ser Glu
    530                 535


<210> SEQ ID NO 5
<211> LENGTH: 2655
<212> TYPE: DNA
<213> ORGANISM: artificial
<220> FEATURE:
<223> OTHER INFORMATION: synthetic

<400> SEQUENCE: 5

tagtaatgaa tggctagcaa aatccagatg cgtaacaaaa aagttctgag ttttctgacc      60

ctgacggcga tcgtgagcca ggccctggtt tatccggtgt acgcgcagac ctctacgagt     120

aaccatagca acaagaaaaa agaaatcgtg aacgaagata tcctgccgaa caatggcctg     180

atgggttatt actttaccga tgaacacttc aaagacctga aactgatggc gccgattaaa     240

gatggcaacc tgaaattcga agagaaaaaa gttgataaac tgctggataa agataaaagc     300

gatgtgaaat ctatccgttg gaccggtcgc attatcccga gcaaagatgg cgaatatacc     360

ctgtctacgg atcgtgatga tgttctgatg caagtgaata ccgaaagcac gatctctaac     420

accctgaaag ttaacatgaa aaagggtaaa gaatacaaag tgcgcatcga actgcaggat     480
```

```
aaaaacctgg gctctatcga taatctgagc tctccgaacc tgtattggga actggatggt    540
atgaagaaaa ttatcccgga agaaaatctg tttctgcgtg attacagcaa cattgaaaaa    600
gatgatccgt tcatcccgaa caataacttt ttcgatccga aactgatgtc tgattgggaa    660
gatgaagacc tggataccga taatgataac attccggata gttatgaacg caatggttac    720
accatcaaag acctgattgc ggttaaatgg gaagatagct ttgccgaaca gggctacaaa    780
aaatacgtga gcaactacct ggaatctaac accgccggtg atccgtatac ggattacgaa    840
aaagcaagcg gctctttcga taaagcaatt aaaaccgaag cgcgtgatcc gctggttgcg    900
gcctatccga tcgtgggcgt tggtatggaa aaactgatta tctctaccaa cgaacatgcg    960
agtaccgatc agggtaaaac cgtgagtcgc gccaccacga atagtaaaac cgaaagcaac   1020
acggcaggcg tgagcgttaa tgtgggctat cagaacggtt ttaccgcgaa tgttaccacg   1080
aactacagcc acaccacgga taattctacc gccgtgcagg attctaatgg cgaaagttgg   1140
aacacgggtc tgagtattaa caaaggcgaa agcgcctaca tcaacgcaaa cgttcgttac   1200
tacaacaccg gtacggcccc gatgtacaaa gttaccccga ccacgaacct ggtgctggat   1260
ggcgataccc tgagcacgat taaagcacag gaaaaccaga tcggtaataa cctgtctccg   1320
ggcgatacct atccgaaaaa aggtctgagt ccgctggcgc tgaataccat ggatcagttt   1380
agtagccgcc tgattccgat caactacgat cagctgaaaa aactggatgc cggcaaacag   1440
attaaactgg aaaccacgca agttagcggc aatttcggta ccaaaaactc tagtggtcag   1500
atcgtgacgg aaggcaatag ttggagcgat tatattagcc agatcgattc tattagtgca   1560
agcattatcc tggataccga aaatgaatct tacgaacgtc gcgtgacggc gaaaaacctg   1620
caagatccgg aagataaaac cccggaactg acgatcggtg aagccattga aaaagcattt   1680
ggtgcgacca aaaaagatgg cctgctgtat ttcaacgata ttccgatcga tgaaagctgc   1740
gttgaactga tcttcgatga taacaccgca aacaaaatca aagatagtct gaaaacgctg   1800
agcgataaga aaatttataa cgtgaaactg gaacgtggca tgaacattct gatcaaaacc   1860
ccgacgtact tcaccaactt cgatgattac aacaactacc cgagtacgtg gagcaatgtt   1920
aacaccacga accaggatgg cctgcagggt agcgccaaca aactgaacgg tgaaaccaaa   1980
atcaaaatcc cgatgtctga actgaaaccg tataaacgct acgtgttttc tggctatagt   2040
aaagatccgc tgacctctaa tagtatcatc gttaaaatca aagcgaaaga agaaaaaacc   2100
gattacctgg tgccggaaca gggttacacg aaattcagtt acgaatttga aaccacggaa   2160
aaagatagct ctaacattga aatcaccctg attggcagcg gtaccacgta tctggataat   2220
ctgtctatta ccgaactgaa cagtacgccg gaaatcctgg atgaaccgga agtgaaaatc   2280
ccgaccgatc aggaaatcat ggatgcccat aaaatctatt tcgcggatct gaacttcaac   2340
ccgagcaccg gtaatacgta tattaacggc atgtactttg caccgaccca gacgaataaa   2400
gaagcgctgg attatattca gaaataccgt gttgaagcca ccctgcagta tagcggcttc   2460
aaagatatcg gtacgaaaga taaagaaatg cgtaattacc tgggcgatcc gaaccagccg   2520
aaaaccaatt atgtgaacct gcgctcttac tttaccggcg gtgaaaacat catgacgtac   2580
aaaaaactgc gtatctacgc gattaccccg gatgatcgcg aactgctggt tctgagtgtg   2640
gattaataac ctagg                                                    2655
```

<210> SEQ ID NO 6
<211> LENGTH: 878
<212> TYPE: PRT
<213> ORGANISM: artificial

-continued

<220> FEATURE:
<223> OTHER INFORMATION: synthetic

<400> SEQUENCE: 6

Met Ala Ser Lys Ile Gln Met Arg Asn Lys Lys Val Leu Ser Phe Leu
1 5 10 15

Thr Leu Thr Ala Ile Val Ser Gln Ala Leu Val Tyr Pro Val Tyr Ala
20 25 30

Gln Thr Ser Thr Ser Asn His Ser Asn Lys Lys Lys Glu Ile Val Asn
35 40 45

Glu Asp Ile Leu Pro Asn Asn Gly Leu Met Gly Tyr Tyr Phe Thr Asp
50 55 60

Glu His Phe Lys Asp Leu Lys Leu Met Ala Pro Ile Lys Asp Gly Asn
65 70 75 80

Leu Lys Phe Glu Glu Lys Lys Val Asp Lys Leu Leu Asp Lys Asp Lys
85 90 95

Ser Asp Val Lys Ser Ile Arg Trp Thr Gly Arg Ile Ile Pro Ser Lys
100 105 110

Asp Gly Glu Tyr Thr Leu Ser Thr Asp Arg Asp Asp Val Leu Met Gln
115 120 125

Val Asn Thr Glu Ser Thr Ile Ser Asn Thr Leu Lys Val Asn Met Lys
130 135 140

Lys Gly Lys Glu Tyr Lys Val Arg Ile Glu Leu Gln Asp Lys Asn Leu
145 150 155 160

Gly Ser Ile Asp Asn Leu Ser Ser Pro Asn Leu Tyr Trp Glu Leu Asp
165 170 175

Gly Met Lys Lys Ile Ile Pro Glu Glu Asn Leu Phe Leu Arg Asp Tyr
180 185 190

Ser Asn Ile Glu Lys Asp Asp Pro Phe Ile Pro Asn Asn Asn Phe Phe
195 200 205

Asp Pro Lys Leu Met Ser Asp Trp Glu Asp Glu Asp Leu Asp Thr Asp
210 215 220

Asn Asp Asn Ile Pro Asp Ser Tyr Glu Arg Asn Gly Tyr Thr Ile Lys
225 230 235 240

Asp Leu Ile Ala Val Lys Trp Glu Asp Ser Phe Ala Glu Gln Gly Tyr
245 250 255

Lys Lys Tyr Val Ser Asn Tyr Leu Glu Ser Asn Thr Ala Gly Asp Pro
260 265 270

Tyr Thr Asp Tyr Glu Lys Ala Ser Gly Ser Phe Asp Lys Ala Ile Lys
275 280 285

Thr Glu Ala Arg Asp Pro Leu Val Ala Ala Tyr Pro Ile Val Gly Val
290 295 300

Gly Met Glu Lys Leu Ile Ile Ser Thr Asn Glu His Ala Ser Thr Asp
305 310 315 320

Gln Gly Lys Thr Val Ser Arg Ala Thr Thr Asn Ser Lys Thr Glu Ser
325 330 335

Asn Thr Ala Gly Val Ser Val Asn Val Gly Tyr Gln Asn Gly Phe Thr
340 345 350

Ala Asn Val Thr Thr Asn Tyr Ser His Thr Thr Asp Asn Ser Thr Ala
355 360 365

Val Gln Asp Ser Asn Gly Glu Ser Trp Asn Thr Gly Leu Ser Ile Asn
370 375 380

Lys Gly Glu Ser Ala Tyr Ile Asn Ala Asn Val Arg Tyr Tyr Asn Thr
385 390 395 400

-continued

```
Gly Thr Ala Pro Met Tyr Lys Val Thr Pro Thr Thr Asn Leu Val Leu
                405                 410                 415

Asp Gly Asp Thr Leu Ser Thr Ile Lys Ala Gln Glu Asn Gln Ile Gly
            420                 425                 430

Asn Asn Leu Ser Pro Gly Asp Thr Tyr Pro Lys Lys Gly Leu Ser Pro
        435                 440                 445

Leu Ala Leu Asn Thr Met Asp Gln Phe Ser Ser Arg Leu Ile Pro Ile
    450                 455                 460

Asn Tyr Asp Gln Leu Lys Lys Leu Asp Ala Gly Lys Gln Ile Lys Leu
465                 470                 475                 480

Glu Thr Thr Gln Val Ser Gly Asn Phe Gly Thr Lys Asn Ser Ser Gly
                485                 490                 495

Gln Ile Val Thr Glu Gly Asn Ser Trp Ser Asp Tyr Ile Ser Gln Ile
            500                 505                 510

Asp Ser Ile Ser Ala Ser Ile Ile Leu Asp Thr Glu Asn Glu Ser Tyr
        515                 520                 525

Glu Arg Arg Val Thr Ala Lys Asn Leu Gln Asp Pro Glu Asp Lys Thr
    530                 535                 540

Pro Glu Leu Thr Ile Gly Glu Ala Ile Glu Lys Ala Phe Gly Ala Thr
545                 550                 555                 560

Lys Lys Asp Gly Leu Leu Tyr Phe Asn Asp Ile Pro Ile Asp Glu Ser
                565                 570                 575

Cys Val Glu Leu Ile Phe Asp Asp Asn Thr Ala Asn Lys Ile Lys Asp
            580                 585                 590

Ser Leu Lys Thr Leu Ser Asp Lys Lys Ile Tyr Asn Val Lys Leu Glu
        595                 600                 605

Arg Gly Met Asn Ile Leu Ile Lys Thr Pro Thr Tyr Phe Thr Asn Phe
    610                 615                 620

Asp Asp Tyr Asn Asn Tyr Pro Ser Thr Trp Ser Asn Val Asn Thr Thr
625                 630                 635                 640

Asn Gln Asp Gly Leu Gln Gly Ser Ala Asn Lys Leu Asn Gly Glu Thr
                645                 650                 655

Lys Ile Lys Ile Pro Met Ser Glu Leu Lys Pro Tyr Lys Arg Tyr Val
            660                 665                 670

Phe Ser Gly Tyr Ser Lys Asp Pro Leu Thr Ser Asn Ser Ile Ile Val
        675                 680                 685

Lys Ile Lys Ala Lys Glu Glu Lys Thr Asp Tyr Leu Val Pro Glu Gln
    690                 695                 700

Gly Tyr Thr Lys Phe Ser Tyr Glu Phe Glu Thr Thr Glu Lys Asp Ser
705                 710                 715                 720

Ser Asn Ile Glu Ile Thr Leu Ile Gly Ser Gly Thr Thr Tyr Leu Asp
                725                 730                 735

Asn Leu Ser Ile Thr Glu Leu Asn Ser Thr Pro Glu Ile Leu Asp Glu
            740                 745                 750

Pro Glu Val Lys Ile Pro Thr Asp Gln Glu Ile Met Asp Ala His Lys
        755                 760                 765

Ile Tyr Phe Ala Asp Leu Asn Phe Asn Pro Ser Thr Gly Asn Thr Tyr
    770                 775                 780

Ile Asn Gly Met Tyr Phe Ala Pro Thr Gln Thr Asn Lys Glu Ala Leu
785                 790                 795                 800

Asp Tyr Ile Gln Lys Tyr Arg Val Glu Ala Thr Leu Gln Tyr Ser Gly
                805                 810                 815
```

-continued

Phe Lys Asp Ile Gly Thr Lys Asp Lys Glu Met Arg Asn Tyr Leu Gly
820 825 830

Asp Pro Asn Gln Pro Lys Thr Asn Tyr Val Asn Leu Arg Ser Tyr Phe
835 840 845

Thr Gly Gly Glu Asn Ile Met Thr Tyr Lys Lys Leu Arg Ile Tyr Ala
850 855 860

Ile Thr Pro Asp Asp Arg Glu Leu Leu Val Leu Ser Val Asp
865 870 875

<210> SEQ ID NO 7
<211> LENGTH: 8045
<212> TYPE: DNA
<213> ORGANISM: artificial
<220> FEATURE:
<223> OTHER INFORMATION: synthetic

<400> SEQUENCE: 7
gaattctgtg gtagcacaga ataatgaaaa gtgtgtaaag aagggtaaaa aaaaccgaat 60
gcgaggcatc cggttgaaat aggggtaaac agacattcag aaatgaatga cggtaataaa 120
taaagttaat gatgatagcg ggagttattc tagttgcgag tgaaggtttt gttttgacat 180
tcagtgctgt caaatactta agaataagtt attgatttta accttgaatt attattgctt 240
gatgttaggt gcttatttcg ccattccgca ataatcttaa aaagttccct tgcatttaca 300
ttttgaaaca tctatagcga taaatgaaac atcttaaaag ttttagtatc atattcgtgt 360
tggattattc tgcatttttg gggagaatgg acttgccgac tgattaatga gggttaatca 420
gtatgcagtg gcataaaaaa gcaaataaag gcatataaca gatcgatctt aaacatccac 480
aggaggatgg gatccaaaat aaggaggaaa aaaaaatgac tagtattttt gcagaacaaa 540
ctgtagaggt agttaaaagc gcgatcgaaa ccgcagatgg ggcattagat ctttataaca 600
aatacctcga ccaggtcatc ccctggaaga cctttgatga aaccataaaa gagttaagcc 660
gttttaaaca ggagtactcg caggaagctt ctgttttagt tggtgatatt aaagttttgc 720
ttatggacag ccaggacaag tattttgaag cgacacaaac tgtttatgaa tggtgtggtg 780
tcgtgacgca attactctca gcgtatattt tactatttga tgaatataat gagaaaaaag 840
catcagccca gaaagacatt ctcattagga tattagatga tggtgtcaag aaactgaatg 900
aagcgcaaaa atctctcctg acaagttcac aaagtttcaa caacgcttcc ggaaaactgc 960
tggcattaga tagccagtta actaatgatt tttcggaaaa aagtagttat ttccagtcac 1020
aggtggatag aattcgtaag gaagcttatg ccggtgctgc agccggcata gtcgccggtc 1080
cgtttggatt aattatttcc tattctattg ctgcgggcgt gattgaaggg aaattgattc 1140
cagaattgaa taacaggcta aaaacagtgc aaaatttctt tactagctta tcagctacag 1200
tgaaacaagc gaataaagat atcgatgcgg caaaattgaa attagccact gaaatagcag 1260
caattgggga gataaaaacg gaaaccgaaa caaccagatt ctacgttgat tatgatgatt 1320
taatgctttc tttattaaaa ggagctgcaa agaaaatgat taacacctgt aatgaatacc 1380
aacaacgtca tggtaagaag acgcttttcg aggttcctga cgtcgctagc ggcctgatct 1440
atattaacga ttcactgtac tatttcaagc cgcccgtcaa taacctcatc accgggtttg 1500
tgacggtcgg cgacgataaa tactacttca atccgatcaa cggcggagcc gcgagcattg 1560
gggagaccat cattgatgac aagaattatt acttcaacca gagtggcgtg ctgcagacgg 1620
gggtcttcag taccgaggac ggctttaaat acttcgcccc cgcgaatacg ctcgatgaga 1680
acctggaagg ggaggcgatt gactttaccg gcaagctgat cattgacgag aacatctact 1740

-continued

```
atttcgatga caattaccgc ggggccgtgg aatggaagga gctcgatggc gagatgcact   1800
attttagccc ggagacgggg aaagctttca aaggcctgaa tcaaattggg gactacaagt   1860
attacttcaa ctctgacggt gtgatgcaga aggggttcgt gagtatcaat gacaacaagc   1920
attatttcga cgattctggc gtcatgaaag tggggtacac cgagatcgat ggcaagcact   1980
tctactttgc cgagaatggt gagatgcaaa tcggcgtgtt caatacggaa gacgggttta   2040
agtatttcgc gcatcataac gaggatctcg gcaatgaaga gggcgaagag atctcatatt   2100
ccggaatcct caacttcaat aacaagattt actactttga tgactcattt accgccgtgg   2160
tcggctggaa ggacctcgag gatgggtcaa agtactattt cgacgaggat acggcggagg   2220
cctacatcgg cctgtcatta atcaacgacg gccagtatta ctttaatgat gacggcatca   2280
tgcaggtcgg gtttgtcacc atcaacgata aagtcttcta cttctctgac tctggcatta   2340
tcgagagcgg ggtgcagaac atcgacgata actatttcta catcgatgac aatggcattg   2400
tccagatcgg cgtgttcgat acgtcagacg gttataagta ttttgcgccc gccaacaccg   2460
tcaacgataa tatctacggt caagctgttg aatatagtgg tttggtccgt gtcggtgaag   2520
acgtgtacta tttcggcgag acgtacacaa ttgagacggg ctggatctat gatatggaga   2580
acgagagtga caagtactat ttcaatcctg agaccaagaa agcatgcaag ggatcaacc    2640
tgatcgatga catcaagtac tatttcgacg agaagggcat tatgcgcacg ggcttatct    2700
catttgagaa taacaattat tacttcaatg agaacgggga aatgcagttt gggtacatca   2760
atattgagga caagatgttc tattttggcg aggatggcgt catgcagatc ggggtgttca   2820
acaccccaga tggtttcaag tatttcgcgc atcagaatac gctggatgag aacttcgagg   2880
gcgaatcaat caactatacc gggtggctgg acctcgatga gaagcgctac tatttcacgg   2940
acgaatacat tgcggccacc ggctcagtca tcattgatgg cgaggaatac tatttcgacc   3000
ctgatacggc gcagctggtg atcagtgagt aatgacctag ctgataacct agcccgccta   3060
atgagcgggc tttttttct cggcctaggt ttcacctgtt ctattaggtg ttacatgctg    3120
ttcatctgtt acattgtcga tctgttcatg gtgaacagct ttaaatgcac caaaaactcg   3180
taaaagctct gatgtatcta tcttttttac accgttttca tctgtgcata tggacagttt   3240
tccctttgat atctaacggt gaacagttgt tctacttttg tttgttagtc ttgatgcttc   3300
actgatagat acaagagcca taagaacctc agatccttcc gtatttagcc agtatgttct   3360
ctagtgtggt tcgttgtttt tgcgtgagcc atgagaacga accattgaga tcatgcttac   3420
tttgcatgtc actcaaaaat tttgcctcaa aactggtgag ctgaattttt gcagttaaag   3480
catcgtgtag tgtttttctt agtccgttac gtaggtagga atctgatgta atggttgttg   3540
gtattttgtc accattcatt tttatctggt tgttctcaag ttcggttacg agatccattt   3600
gtctatctag ttcaacttgg aaaatcaacg tatcagtcgg gcggcctcgc ttatcaacca   3660
ccaatttcat attgctgtaa gtgtttaaat ctttacttat tggtttcaaa acccattggt   3720
taagcctttt aaactcatgg tagttatttt caagcattaa catgaactta aattcatcaa   3780
ggctaatctc tatatttgcc ttgtgagttt tcttttgtgt tagttctttt aataaccact   3840
cataaatcct catagagtat ttgttttcaa aagacttaac atgttccaga ttatatttta   3900
tgaatttttt taactggaaa agataaggca atatctcttc actaaaaact aattctaatt   3960
tttcgcttga gaacttggca tagtttgtcc actggaaaat ctcaaagcct ttaaccaaag   3a020
gattcctgat ttccacagtt ctcgtcatca gctctctggt tgctttagct aatacaccat   4080
```

-continued

```
aagcattttc cctactgatg ttcatcatct gagcgtattg gttataagtg aacgataccg   4140
tccgttcttt ccttgtaggg ttttcaatcg tggggttgag tagtgccaca cagcataaaa   4200
ttagcttggt ttcatgctcc gttaagtcat agcgactaat cgctagttca tttgctttga   4260
aaacaactaa ttcagacata catctcaatt ggtctaggtg attttaatca ctataccaat   4320
tgagatgggc tagtcaatga taattactag ctagtccttt tcctttgagt tgtgggtatc   4380
tgtaaattct gctagacctt tgctggaaaa cttgtaaatt ctgctagacc ctctgtaaat   4440
tccgctagac ctttgtgtgt ttttttgtt tatattcaag tggttataat ttatagaata   4500
aagaaagaat aaaaaaagat aaaaagaata gatcccagcc ctgtgtataa ctcactactt   4560
tagtcagttc cgcagtatta caaaaggatg tcgcaaacgc tgtttgctcc tctacaaaac   4620
agaccttaaa accctaaagg cttaagtagc accctcgcaa gctcgggcaa atcgctgaat   4680
attccttttg tctccgacca tcaggcacct gagtcgctgt ctttttcgtg acattcagtt   4740
cgctgcgctc acggctctgg cagtgaatgg gggtaaatgg cactacaggc gccttttatg   4800
gattcatgca aggaaactac ccataataca agaaaagccc gtcacgggct tctcagggcg   4860
ttttatggcg ggtctgctat gtggtgctat ctgacttttt gctgttcagc agttcctgcc   4920
ctctgatttt ccagtctgac cacttcggat tatcccgtga caggtcattc agactggcta   4980
atgcacccag taaggcagcg gtatcatcaa caggcttacc cgtcttactg tcaaccggat   5040
ctaaaacact aggcccaaga gtttgtagaa acgcaaaaag gccatccgtc aggatggcct   5100
tctgcttaat ttgatgcctg gcagtttatg gcgggcgtcc tgcccgccac cctccgggcc   5160
gttgcttcgc aacgttcaaa tccgctcccg gcggatttgt cctactcagg agagcgttca   5220
ccgacaaaca acagataaaa cgaaaggccc agtctttcga ctgagccttt cgttttattt   5280
gatgcctggc agttccctac tctcgcatgg ggagacccca cactaccatc ggcgctacgg   5340
cgtttcactt ctgagttcgg catggggtca ggtgggacca ccgcgctact gccgccaggc   5400
aaattctgtt ttatcagacc gcttctgcgt tctgatttaa tctgtatcag gctgaaaatc   5460
ttctctcatc cgccaaaaca gccaagctgg atctaaaaca ctagctctag ctattgtttt   5520
aatgacaaat cagaacggaa tgtcatcatc aaagtccatc ggcggctcgt tagacggcgc   5580
tgccggagcg gactgctgcg ggcgagactg cgcgccgccg ctgaactgat tgccaccctg   5640
cggctgctga ggctgacccc aaccgccctg cggctgacca ccaccgatat tgccacctgc   5700
cggagcgcca ccaccctgac gaccacccag catctgcatg gtgccgccaa cgttcaccac   5760
gacttctgtg gtgtagcgat cctgaccgga ttgatcggtc catttacggg tacgcagctg   5820
accttcgata taaacctgag aacctttacg cagatattcg ctcgccactt ctgccagttt   5880
gccgaacagc acaacgcggt gccattcagt ctgttctttc atctcgccgg tcgctttatc   5940
acgccaggat tcggaagtag ccagcgtaat gttggcaact gcgccaccat ttggcatgta   6000
gcgtacttcc gggtcctgac ccagattacc aacgagaata accttgttta cgcctctgct   6060
ggccatgttc gtgtctcctg aaaaaaatcg ttctgaataa gtgtaaacgc gcgattgtac   6120
cattaccaat agcgctttta ctatgttgtg acctcggttc cgggaaacaa acctggccag   6180
acattgttac acaacactcc ggataatgca ttccaatact gtatattcat tcaggtcaat   6240
catatgaagg gcgaattctg cagatatcca tcacactggc ggccgccagt gtgatggata   6300
tctgcagaat tcgcccttga gaagttccta ttctatatat agtataggaa cttctctaga   6360
acttttgtta cccgccaaac aaaacccaaa aacaacccat acccaaccca ataaaacacc   6420
aaaacaagac aaataatcat tgattgatgg ttgaaatggg gtaaacttga caaacaaacc   6480
```

```
cacttaaaac ccaaaacata cccaaacaca caccaaaaaa acaccataag gagttttata   6540

aatgttggta ttcattgatg acggttcaac aaacatcaaa ctacagtggc aggaaagcga   6600

cggaacaatt aaacagcaca ttagcccgaa cagcttcaaa cgcgagtggg cagtctcttt   6660

tggtgataaa aaggtcttta actacacact gaacggcgaa cagtattcat ttgatccaat   6720

cagcccggat gctgtagtca caaccaatat cgcatggcaa tacagcgacg ttaatgtcgt   6780

tgcagtgcat cacgccttac tgaccagtgg tctgccggta agcgaagtgg atattgtttg   6840

cacacttcct ctgacagagt attacgacag aaataaccaa cccaatacgg aaaatattga   6900

gcgtaagaaa gcaaacttcc ggaaaaaaat tacattaaat ggcggggata cattcacaat   6960

aaaagatgta aaagtcatgc ctgaatctat accggcaggt tatgaagttc tacaagaact   7020

ggatgagtta gattctttat taattataga tctcgggggc accacattag atatttctca   7080

ggtaatgggg aaattatcgg ggatcagtaa aatatacgga gactcatctc ttggtgtctc   7140

tctggttaca tctgcagtaa aagatgccct ttctcttgcg agaacaaaag gaagtagcta   7200

tcttgctgac gatataatca ttcacagaaa agataataac tatctgaagc aacgaattaa   7260

tgatgagaac aaaatatcaa tagtcaccga agcaatgaat gaagcacttc gtaaacttga   7320

gcaacgtgta ttaaatacgc tcaatgaatt ttctggttat actcatgtta tggttatagg   7380

cggtggcgca gaattaatat gcgatgcagt aaaaaaacac acacagattc gtgatgaacg   7440

tttttcaaa accaataact ctcaatatga tttagttaac ggtatgtatc tcataggtaa   7500

ttaatgatgg acaagcgcag aaccattgcc ttcaaactaa atccagatgt aaatcaaaca   7560

gataaaattg tttgtgatac actggacagt atcccgcaag gggaacgaag ccgccttaac   7620

cgggccgcac tgacggcagg tctggcctta tacagacaag atccccggac ccctttcctt   7680

ttatgtgagc tgctgacgaa agaaaccaca ttttcagata tcgtgaatat attgagatcg   7740

ctatttccaa aagagatggc cgattttaat tcttcaatag tcactcaatc ctcttcacaa   7800

caagagcaaa aaagtgatga agagaccaaa aaaaatgcga tgaagctaat aaattaattc   7860

aattattatt gagttccctt tatccactat caggctggat aaagggaact caatcaagtt   7920

attttcttac cagtcattac ataatcgtta ttatgaaata atcgtttgca ctgtctctgt   7980

tattcaggca atttcaataa aggcacttgc tcacgctctg tcattttctg aaactcttca   8040

tgctg                                                               8045
```

```
<210> SEQ ID NO 8
<211> LENGTH: 838
<212> TYPE: PRT
<213> ORGANISM: artificial
<220> FEATURE:
<223> OTHER INFORMATION: synthetic

<400> SEQUENCE: 8

Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80
```

-continued

```
Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Phe Glu Val Pro Asp Val Ala
    290                 295                 300

Ser Gly Leu Ile Tyr Ile Asn Asp Ser Leu Tyr Tyr Phe Lys Pro Pro
305                 310                 315                 320

Val Asn Asn Leu Ile Thr Gly Phe Val Thr Val Gly Asp Asp Lys Tyr
                325                 330                 335

Tyr Phe Asn Pro Ile Asn Gly Gly Ala Ala Ser Ile Gly Glu Thr Ile
            340                 345                 350

Ile Asp Asp Lys Asn Tyr Tyr Phe Asn Gln Ser Gly Val Leu Gln Thr
        355                 360                 365

Gly Val Phe Ser Thr Glu Asp Gly Phe Lys Tyr Phe Ala Pro Ala Asn
    370                 375                 380

Thr Leu Asp Glu Asn Leu Glu Gly Glu Ala Ile Asp Phe Thr Gly Lys
385                 390                 395                 400

Leu Ile Ile Asp Glu Asn Ile Tyr Tyr Phe Asp Asp Asn Tyr Arg Gly
                405                 410                 415

Ala Val Glu Trp Lys Glu Leu Asp Gly Glu Met His Tyr Phe Ser Pro
            420                 425                 430

Glu Thr Gly Lys Ala Phe Lys Gly Leu Asn Gln Ile Gly Asp Tyr Lys
        435                 440                 445

Tyr Tyr Phe Asn Ser Asp Gly Val Met Gln Lys Gly Phe Val Ser Ile
    450                 455                 460

Asn Asp Asn Lys His Tyr Phe Asp Asp Ser Gly Val Met Lys Val Gly
465                 470                 475                 480

Tyr Thr Glu Ile Asp Gly Lys His Phe Tyr Phe Ala Glu Asn Gly Glu
                485                 490                 495
```

```
Met Gln Ile Gly Val Phe Asn Thr Glu Asp Gly Phe Lys Tyr Phe Ala
            500                 505                 510

His His Asn Glu Asp Leu Gly Asn Glu Glu Gly Glu Glu Ile Ser Tyr
        515                 520                 525

Ser Gly Ile Leu Asn Phe Asn Asn Lys Ile Tyr Tyr Phe Asp Asp Ser
    530                 535                 540

Phe Thr Ala Val Val Gly Trp Lys Asp Leu Glu Asp Gly Ser Lys Tyr
545                 550                 555                 560

Tyr Phe Asp Glu Asp Thr Ala Glu Ala Tyr Ile Gly Leu Ser Leu Ile
                565                 570                 575

Asn Asp Gly Gln Tyr Tyr Phe Asn Asp Asp Gly Ile Met Gln Val Gly
            580                 585                 590

Phe Val Thr Ile Asn Asp Lys Val Phe Tyr Phe Ser Asp Ser Gly Ile
        595                 600                 605

Ile Glu Ser Gly Val Gln Asn Ile Asp Asp Asn Tyr Phe Tyr Ile Asp
    610                 615                 620

Asp Asn Gly Ile Val Gln Ile Gly Val Phe Asp Thr Ser Asp Gly Tyr
625                 630                 635                 640

Lys Tyr Phe Ala Pro Ala Asn Thr Val Asn Asp Asn Ile Tyr Gly Gln
                645                 650                 655

Ala Val Glu Tyr Ser Gly Leu Val Arg Val Gly Glu Asp Val Tyr Tyr
            660                 665                 670

Phe Gly Glu Thr Tyr Thr Ile Glu Thr Gly Trp Ile Tyr Asp Met Glu
        675                 680                 685

Asn Glu Ser Asp Lys Tyr Tyr Phe Asn Pro Glu Thr Lys Lys Ala Cys
    690                 695                 700

Lys Gly Ile Asn Leu Ile Asp Asp Ile Lys Tyr Tyr Phe Asp Glu Lys
705                 710                 715                 720

Gly Ile Met Arg Thr Gly Leu Ile Ser Phe Glu Asn Asn Asn Tyr Tyr
                725                 730                 735

Phe Asn Glu Asn Gly Glu Met Gln Phe Gly Tyr Ile Asn Ile Glu Asp
            740                 745                 750

Lys Met Phe Tyr Phe Gly Glu Asp Gly Val Met Gln Ile Gly Val Phe
        755                 760                 765

Asn Thr Pro Asp Gly Phe Lys Tyr Phe Ala His Gln Asn Thr Leu Asp
    770                 775                 780

Glu Asn Phe Glu Gly Glu Ser Ile Asn Tyr Thr Gly Trp Leu Asp Leu
785                 790                 795                 800

Asp Glu Lys Arg Tyr Tyr Phe Thr Asp Glu Tyr Ile Ala Ala Thr Gly
                805                 810                 815

Ser Val Ile Ile Asp Gly Glu Glu Tyr Tyr Phe Asp Pro Asp Thr Ala
            820                 825                 830

Gln Leu Val Ile Ser Glu
        835
```

```
<210> SEQ ID NO 9
<211> LENGTH: 8045
<212> TYPE: DNA
<213> ORGANISM: artificial
<220> FEATURE:
<223> OTHER INFORMATION: synthetic

<400> SEQUENCE: 9

gaattctgtg gtagcacaga ataatgaaaa gtgtgtaaag aagggtaaaa aaaaccgaat      60

gcgaggcatc cggttgaaat aggggtaaac agacattcag aaatgaatga cggtaataaa     120
```

```
taaagttaat gatgatagcg ggagttattc tagttgcgag tgaaggtttt gttttgacat    180
tcagtgctgt caaatactta agaataagtt attgatttta accttgaatt attattgctt    240
gatgttaggt gcttatttcg ccattccgca ataatcttaa aaagttccct tgcatttaca    300
ttttgaaaca tctatagcga taaatgaaac atcttaaaag ttttagtatc atattcgtgt    360
tggattattc tgcatttttg gggagaatgg acttgccgac tgattaatga gggttaatca    420
gtatgcagtg gcataaaaaa gcaaataaag gcatataaca gatcgatctt aaacatccac    480
aggaggatgg gatccaaaat aaggaggaaa aaaaaatgac tagtattttt gcagaacaaa    540
ctgtagaggt agttaaaagc gcgatcgaaa ccgcagatgg ggcattagat ctttataaca    600
aatacctcga ccaggtcatc ccctggaaga cctttgatga aaccataaaa gagttaagcc    660
gttttaaaca ggagtactcg caggaagctt ctgttttagt tggtgatatt aaagttttgc    720
ttatggacag ccaggacaag tattttgaag cgacacaaac tgtttatgaa tggtgtggtg    780
tcgtgacgca attactctca gcgtatattt tactatttga tgaatataat gagaaaaaag    840
catcagccca gaaagacatt ctcattagga tattagatga tggtgtcaag aaactgaatg    900
aagcgcaaaa atctctcctg acaagttcac aaagtttcaa caacgcttcc ggaaaactgc    960
tggcattaga tagccagtta actaatgatt tttcggaaaa aagtagttat ttccagtcac   1020
aggtggatag aattcgtaag gaagcttatg ccggtgctgc agccggcata gtcgccggtc   1080
cgtttggatt aattatttcc tattctaatg ctgcgggcgt gattgaaggg aaattgattc   1140
cagaattgaa taacaggcta aaaacagtgc aaaatttctt tactagctta tcagctacag   1200
tgaaacaagc gaataaagat atcgatgcgg caaaattgaa attagccact gaaatagcag   1260
caattgggga gataaaaacg gaaaccgaaa caaccagatt ctacgttgat tatgatgatt   1320
taatgctttc tttattaaaa ggagctgcaa agaaaatgat taacacctgg aatgaatacc   1380
aacaacgtca tggtaagaag acgcttttcg aggttcctga cgtcgctagc ggcctgatct   1440
atattaacga ttcactgtac tatttcaagc cgcccgtcaa taacctcatc accgggtttg   1500
tgacggtcgg cgacgataaa tactacttca atccgatcaa cggcggagcc gcgagcattg   1560
gggagaccat cattgatgac aagaattatt acttcaacca gagtggcgtg ctgcagacgg   1620
gggtcttcag taccgaggac ggctttaaat acttcgcccc cgcgaatacg ctcgatgaga   1680
acctggaagg ggaggcgatt gactttaccg gcaagctgat cattgacgag aacatctact   1740
atttcgatga caattaccgc ggggccgtgg aatggaagga gctcgatggc gagatgcact   1800
attttagccc ggagacgggg aaagctttca aaggcctgaa tcaaattggg gactacaagt   1860
attacttcaa ctctgacggt gtgatgcaga aggggttcgt gagtatcaat gacaacaagc   1920
attatttcga cgattctggc gtcatgaaag tggggtacac cgagatcgat ggcaagcact   1980
tctactttgc cgagaatggt gagatgcaaa tcggcgtgtt caatacggaa gacgggttta   2040
agtatttcgc gcatcataac gaggatctcg gcaatgaaga gggcgaagag atctcatatt   2100
ccggaatcct caacttcaat aacaagattt actactttga tgactcattt accgccgtgg   2160
tcggctggaa ggacctcgag gatgggtcaa agtactattt cgacgaggat acggcggagg   2220
cctacatcgg cctgtcatta atcaacgacg gccagtatta ctttaatgat gacggcatca   2280
tgcaggtcgg gtttgtcacc atcaacgata aagtcttcta cttctctgac tctggcatta   2340
tcgagagcgg ggtgcagaac atcgacgata actatttcta catcgatgac aatggcattg   2400
tccagatcgg cgtgttcgat acgtcagacg gttataagta ttttgcgccc gccaacaccg   2460
```

-continued

```
tcaacgataa tatctacggt caagctgttg aatatagtgg tttggtccgt gtcggtgaag   2520
acgtgtacta tttcggcgag acgtacacaa ttgagacggg ctggatctat gatatggaga   2580
acgagagtga caagtactat ttcaatcctg agaccaagaa agcatgcaag gggatcaacc   2640
tgatcgatga catcaagtac tatttcgacg agaagggcat tatgcgcacg gggcttatct   2700
catttgagaa taacaattat tacttcaatg agaacgggga aatgcagttt gggtacatca   2760
atattgagga caagatgttc tattttggcg aggatggcgt catgcagatc ggggtgttca   2820
acaccccaga tggtttcaag tatttcgcgc atcagaatac gctggatgag aacttcgagg   2880
gcgaatcaat caactatacc gggtggctgg acctcgatga gaagcgctac tatttcacgg   2940
acgaatacat tgcggccacc ggctcagtca tcattgatgg cgaggaatac tatttcgacc   3000
ctgatacggc gcagctggtg atcagtgagt aatgacctag ctgataacct agcccgccta   3060
atgagcgggc tttttttct cggcctaggt ttcacctgtt ctattaggtg ttacatgctg   3120
ttcatctgtt acattgtcga tctgttcatg gtgaacagct ttaaatgcac caaaaactcg   3180
taaaagctct gatgtatcta tcttttttac accgttttca tctgtgcata tggacagttt   3240
tccctttgat atctaacggt gaacagttgt tctacttttg tttgttagtc ttgatgcttc   3300
actgatagat acaagagcca taagaacctc agatccttcc gtatttagcc agtatgttct   3360
ctagtgtggt tcgttgtttt tgcgtgagcc atgagaacga accattgaga tcatgcttac   3420
tttgcatgtc actcaaaaat tttgcctcaa aactggtgag ctgaattttt gcagttaaag   3480
catcgtgtag tgtttttctt agtccgttac gtaggtagga atctgatgta atggttgttg   3540
gtattttgtc accattcatt tttatctggt tgttctcaag ttcggttacg agatccattt   3600
gtctatctag ttcaacttgg aaaatcaacg tatcagtcgg gcggcctcgc ttatcaacca   3660
ccaatttcat attgctgtaa gtgtttaaat ctttacttat tggtttcaaa acccattggt   3720
taagcctttt aaactcatgg tagttatttt caagcattaa catgaactta aattcatcaa   3780
ggctaatctc tatatttgcc ttgtgagttt tcttttgtgt tagttctttt aataaccact   3840
cataaatcct catagagtat ttgttttcaa aagacttaac atgttccaga ttatatttta   3900
tgaatttttt taactggaaa agataaggca atatctcttc actaaaaact aattctaatt   3960
tttcgcttga gaacttggca tagtttgtcc actggaaaat ctcaaagcct ttaaccaaag   4020
gattcctgat ttccacagtt ctcgtcatca gctctctggt tgctttagct aatacaccat   4080
aagcattttc cctactgatg ttcatcatct gagcgtattg gttataagtg aacgataccg   4140
tccgttcttt ccttgtaggg ttttcaatcg tggggttgag tagtgccaca cagcataaaa   4200
ttagcttggt ttcatgctcc gttaagtcat agcgactaat cgctagttca tttgctttga   4260
aaacaactaa ttcagacata catctcaatt ggtctaggtg attttaatca ctataccaat   4320
tgagatgggc tagtcaatga taattactag ctagtccttt tcctttgagt tgtgggtatc   4380
tgtaaattct gctagacctt tgctggaaaa cttgtaaatt ctgctagacc ctctgtaaat   4440
tccgctagac ctttgtgtgt tttttttgtt tatattcaag tggttataat ttatagaata   4500
aagaaagaat aaaaaaagat aaaaagaata gatcccagcc ctgtgtataa ctcactactt   4560
tagtcagttc cgcagtatta caaaaggatg tcgcaaacgc tgtttgctcc tctacaaaac   4620
agaccttaaa accctaaagg cttaagtagc accctcgcaa gctcgggcaa atcgctgaat   4680
attccttttg tctccgacca tcaggcacct gagtcgctgt ctttttcgtg acattcagtt   4740
cgctgcgctc acggctctgg cagtgaatgg gggtaaatgg cactacaggc gccttttatg   4800
gattcatgca aggaaactac ccataataca agaaaagccc gtcacgggct tctcagggcg   4860
```

-continued

```
ttttatggcg ggtctgctat gtggtgctat ctgacttttt gctgttcagc agttcctgcc   4920
ctctgatttt ccagtctgac cacttcggat tatcccgtga caggtcattc agactggcta   4980
atgcacccag taaggcagcg gtatcatcaa caggcttacc cgtcttactg tcaaccggat   5040
ctaaaacact aggcccaaga gtttgtagaa acgcaaaaag gccatccgtc aggatggcct   5100
tctgcttaat ttgatgcctg gcagtttatg gcgggcgtcc tgcccgccac cctccgggcc   5160
gttgcttcgc aacgttcaaa tccgctcccg gcggatttgt cctactcagg agagcgttca   5220
ccgacaaaca acagataaaa cgaaaggccc agtctttcga ctgagccttt cgttttattt   5280
gatgcctggc agttccctac tctcgcatgg ggagacccca cactaccatc ggcgctacgg   5340
cgtttcactt ctgagttcgg catggggtca ggtgggacca ccgcgctact gccgccaggc   5400
aaattctgtt ttatcagacc gcttctgcgt tctgatttaa tctgtatcag gctgaaaatc   5460
ttctctcatc cgccaaaaca gccaagctgg atctaaaaca ctagctctag ctattgtttt   5520
aatgacaaat cagaacggaa tgtcatcatc aaagtccatc ggcggctcgt tagacggcgc   5580
tgccggagcg gactgctgcg ggcgagactg cgcgccgccg ctgaactgat tgccaccctg   5640
cggctgctga ggctgacccc aaccgccctg cggctgacca ccaccgatat tgccacctgc   5700
cggagcgcca ccaccctgac gaccacccag catctgcatg gtgccgccaa cgttcaccac   5760
gacttctgtg gtgtagcgat cctgaccgga ttgatcggtc catttacggg tacgcagctg   5820
accttcgata taaacctgag aacctttacg cagatattcg ctcgccactt ctgccagttt   5880
gccgaacagc acaacgcggt gccattcagt ctgttctttc atctcgccgg tcgctttatc   5940
acgccaggat tcggaagtag ccagcgtaat gttggcaact gcgccaccat ttggcatgta   6000
gcgtacttcc gggtcctgac ccagattacc aacgagaata accttgttta cgcctctgct   6060
ggccatgttc gtgtctcctg aaaaaaatcg ttctgaataa gtgtaaacgc gcgattgtac   6120
cattaccaat agcgctttta ctatgttgtg acctcggttc cgggaaacaa acctggccag   6180
acattgttac acaacactcc ggataatgca ttccaatact gtatattcat tcaggtcaat   6240
catatgaagg gcgaattctg cagatatcca tcacactggc ggccgccagt gtgatggata   6300
tctgcagaat tcgcccttga gaagttccta ttctatatat agtataggaa cttctctaga   6360
acttttgtta cccgccaaac aaaacccaaa aacaacccat acccaaccca ataaaacacc   6420
aaaacaagac aaataatcat tgattgatgg ttgaaatggg gtaaacttga caaacaaacc   6480
cacttaaaac ccaaaacata cccaaacaca caccaaaaaa acaccataag gagttttata   6540
aatgttggta ttcattgatg acggttcaac aaacatcaaa ctacagtggc aggaaagcga   6600
cggaacaatt aaacagcaca ttagcccgaa cagcttcaaa cgcgagtggg cagtctcttt   6660
tggtgataaa aaggtcttta actacacact gaacggcgaa cagtattcat ttgatccaat   6720
cagcccggat gctgtagtca caaccaatat cgcatggcaa tacagcgacg ttaatgtcgt   6780
tgcagtgcat cacgccttac tgaccagtgg tctgccggta agcgaagtgg atattgtttg   6840
cacacttcct ctgacagagt attacgacag aaataaccaa cccaatacgg aaaatattga   6900
gcgtaagaaa gcaaacttcc ggaaaaaaat tacattaaat ggcggggata cattcacaat   6960
aaaagatgta aaagtcatgc ctgaatctat accggcaggt tatgaagttc tacaagaact   7020
ggatgagtta gattctttat taattataga tctcgggggc accacattag atatttctca   7080
ggtaatgggg aaattatcgg ggatcagtaa aatatacgga gactcatctc ttggtgtctc   7140
tctggttaca tctgcagtaa aagatgccct ttctcttgcg agaacaaaag gaagtagcta   7200
```

```
tcttgctgac gatataatca ttcacagaaa agataataac tatctgaagc aacgaattaa    7260

tgatgagaac aaaatatcaa tagtcaccga agcaatgaat gaagcacttc gtaaacttga    7320

gcaacgtgta ttaaatacgc tcaatgaatt ttctggttat actcatgtta tggttatagg    7380

cggtggcgca gaattaatat gcgatgcagt aaaaaaacac acacagattc gtgatgaacg    7440

tttttttcaaa accaataact ctcaatatga tttagttaac ggtatgtatc tcataggtaa    7500

ttaatgatgg acaagcgcag aaccattgcc ttcaaactaa atccagatgt aaatcaaaca    7560

gataaaattg tttgtgatac actggacagt atcccgcaag gggaacgaag ccgccttaac    7620

cgggccgcac tgacggcagg tctggcctta tacagacaag atccccggac ccctttcctt    7680

ttatgtgagc tgctgacgaa agaaaccaca ttttcagata tcgtgaatat attgagatcg    7740

ctatttccaa aagagatggc cgattttaat tcttcaatag tcactcaatc ctcttcacaa    7800

caagagcaaa aaagtgatga agagaccaaa aaaaatgcga tgaagctaat aaattaattc    7860

aattattatt gagttccctt tatccactat caggctggat aaagggaact caatcaagtt    7920

attttcttac cagtcattac ataatcgtta ttatgaaata atcgtttgca ctgtctctgt    7980

tattcaggca atttcaataa aggcacttgc tcacgctctg tcattttctg aaactcttca    8040

tgctg                                                                8045
```

<210> SEQ ID NO 10
<211> LENGTH: 838
<212> TYPE: PRT
<213> ORGANISM: artificial
<220> FEATURE:
<223> OTHER INFORMATION: synthetic

<400> SEQUENCE: 10

Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Asn Ala Ala Gly Val Ile Glu Gly Lys Leu Ile
        195                 200                 205

-continued

```
Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Trp Asn Glu Tyr
        275                 280                 285

Gln Gln Arg His Gly Lys Lys Thr Leu Phe Glu Val Pro Asp Val Ala
    290                 295                 300

Ser Gly Leu Ile Tyr Ile Asn Asp Ser Leu Tyr Tyr Phe Lys Pro Pro
305                 310                 315                 320

Val Asn Asn Leu Ile Thr Gly Phe Val Thr Val Gly Asp Asp Lys Tyr
                325                 330                 335

Tyr Phe Asn Pro Ile Asn Gly Gly Ala Ala Ser Ile Gly Glu Thr Ile
            340                 345                 350

Ile Asp Asp Lys Asn Tyr Tyr Phe Asn Gln Ser Gly Val Leu Gln Thr
        355                 360                 365

Gly Val Phe Ser Thr Glu Asp Gly Phe Lys Tyr Phe Ala Pro Ala Asn
    370                 375                 380

Thr Leu Asp Glu Asn Leu Glu Gly Glu Ala Ile Asp Phe Thr Gly Lys
385                 390                 395                 400

Leu Ile Ile Asp Glu Asn Ile Tyr Tyr Phe Asp Asp Asn Tyr Arg Gly
                405                 410                 415

Ala Val Glu Trp Lys Glu Leu Asp Gly Glu Met His Tyr Phe Ser Pro
            420                 425                 430

Glu Thr Gly Lys Ala Phe Lys Gly Leu Asn Gln Ile Gly Asp Tyr Lys
        435                 440                 445

Tyr Tyr Phe Asn Ser Asp Gly Val Met Gln Lys Gly Phe Val Ser Ile
    450                 455                 460

Asn Asp Asn Lys His Tyr Phe Asp Asp Ser Gly Val Met Lys Val Gly
465                 470                 475                 480

Tyr Thr Glu Ile Asp Gly Lys His Phe Tyr Phe Ala Glu Asn Gly Glu
                485                 490                 495

Met Gln Ile Gly Val Phe Asn Thr Glu Asp Gly Phe Lys Tyr Phe Ala
            500                 505                 510

His His Asn Glu Asp Leu Gly Asn Glu Glu Gly Glu Glu Ile Ser Tyr
        515                 520                 525

Ser Gly Ile Leu Asn Phe Asn Asn Lys Ile Tyr Tyr Phe Asp Asp Ser
    530                 535                 540

Phe Thr Ala Val Val Gly Trp Lys Asp Leu Glu Asp Gly Ser Lys Tyr
545                 550                 555                 560

Tyr Phe Asp Glu Asp Thr Ala Glu Ala Tyr Ile Gly Leu Ser Leu Ile
                565                 570                 575

Asn Asp Gly Gln Tyr Tyr Phe Asn Asp Asp Gly Ile Met Gln Val Gly
            580                 585                 590

Phe Val Thr Ile Asn Asp Lys Val Phe Tyr Phe Ser Asp Ser Gly Ile
        595                 600                 605

Ile Glu Ser Gly Val Gln Asn Ile Asp Asp Asn Tyr Phe Tyr Ile Asp
    610                 615                 620

Asp Asn Gly Ile Val Gln Ile Gly Val Phe Asp Thr Ser Asp Gly Tyr
```

```
625                 630                 635                 640

Lys Tyr Phe Ala Pro Ala Asn Thr Val Asn Asp Asn Ile Tyr Gly Gln
                645                 650                 655

Ala Val Glu Tyr Ser Gly Leu Val Arg Val Gly Glu Asp Val Tyr Tyr
            660                 665                 670

Phe Gly Glu Thr Tyr Thr Ile Glu Thr Gly Trp Ile Tyr Asp Met Glu
        675                 680                 685

Asn Glu Ser Asp Lys Tyr Tyr Phe Asn Pro Glu Thr Lys Lys Ala Cys
    690                 695                 700

Lys Gly Ile Asn Leu Ile Asp Asp Ile Lys Tyr Tyr Phe Asp Glu Lys
705                 710                 715                 720

Gly Ile Met Arg Thr Gly Leu Ile Ser Phe Glu Asn Asn Asn Tyr Tyr
                725                 730                 735

Phe Asn Glu Asn Gly Glu Met Gln Phe Gly Tyr Ile Asn Ile Glu Asp
            740                 745                 750

Lys Met Phe Tyr Phe Gly Glu Asp Gly Val Met Gln Ile Gly Val Phe
        755                 760                 765

Asn Thr Pro Asp Gly Phe Lys Tyr Phe Ala His Gln Asn Thr Leu Asp
    770                 775                 780

Glu Asn Phe Glu Gly Glu Ser Ile Asn Tyr Thr Gly Trp Leu Asp Leu
785                 790                 795                 800

Asp Glu Lys Arg Tyr Tyr Phe Thr Asp Glu Tyr Ile Ala Ala Thr Gly
                805                 810                 815

Ser Val Ile Ile Asp Gly Glu Glu Tyr Tyr Phe Asp Pro Asp Thr Ala
            820                 825                 830

Gln Leu Val Ile Ser Glu
        835
```

<210> SEQ ID NO 11
<211> LENGTH: 7139
<212> TYPE: DNA
<213> ORGANISM: artificial
<220> FEATURE:
<223> OTHER INFORMATION: synthetic

<400> SEQUENCE: 11

```
gaattctgtg gtagcacaga ataatgaaaa gtgtgtaaag aagggtaaaa aaaaccgaat      60

gcgaggcatc cggttgaaat aggggtaaac agacattcag aaatgaatga cggtaataaa     120

taaagttaat gatgatagcg ggagttattc tagttgcgag tgaaggtttt gttttgacat     180

tcagtgctgt caaatactta agaataagtt attgatttta accttgaatt attattgctt     240

gatgttaggt gcttatttcg ccattccgca ataatcttaa aaagttccct tgcatttaca     300

ttttgaaaca tctatagcga taaatgaaac atcttaaaag ttttagtatc atattcgtgt     360

tggattattc tgcatttttg gggagaatgg acttgccgac tgattaatga gggttaatca     420

gtatgcagtg gcataaaaaa gcaaataaag gcatataaca gatcgatctt aaacatccac     480

aggaggatgg gatccaaaat aaggaggaaa aaaaaatgac tagcggcctg atctatatta     540

acgattcact gtactatttc aagccgcccg tcaataacct catcaccggg tttgtgacgg     600

tcggcgacga taaatactac ttcaatccga tcaacggcgg agccgcgagc attggggaga     660

ccatcattga tgacaagaat tattacttca accagagtgg cgtgctgcag acgggggtct     720

tcagtaccga ggacggcttt aaatacttcg cccccgcgaa tacgctcgat gagaacctgg     780

aaggggaggc gattgacttt accggcaagc tgatcattga cgagaacatc tactatttcg     840
```

-continued

```
atgacaatta ccgcggggcc gtggaatgga aggagctcga tggcgagatg cactatttta    900
gcccggagac ggggaaagct ttcaaaggcc tgaatcaaat tggggactac aagtattact    960
tcaactctga cggtgtgatg cagaaggggt tcgtgagtat caatgacaac aagcattatt   1020
tcgacgattc tggcgtcatg aaagtggggt acaccgagat cgatggcaag cacttctact   1080
ttgccgagaa tggtgagatg caaatcggcg tgttcaatac ggaagacggg tttaagtatt   1140
tcgcgcatca taacgaggat ctcggcaatg aagagggcga agagatctca tattccggaa   1200
tcctcaactt caataacaag atttactact ttgatgactc atttaccgcc gtggtcggct   1260
ggaaggacct cgaggatggg tcaaagtact atttcgacga ggatacggcg gaggcctaca   1320
tcggcctgtc attaatcaac gacggccagt attactttaa tgatgacggc atcatgcagg   1380
tcgggtttgt caccatcaac gataaagtct tctacttctc tgactctggc attatcgaga   1440
gcggggtgca gaacatcgac gataactatt tctacatcga tgacaatggc attgtccaga   1500
tcggcgtgtt cgatacgtca gacggttata agtattttgc gcccgccaac accgtcaacg   1560
ataatatcta cggtcaagct gttgaatata gtggtttggt ccgtgtcggt gaagacgtgt   1620
actatttcgg cgagacgtac acaattgaga cgggctggat ctatgatatg gagaacgaga   1680
gtgacaagta ctatttcaat cctgagacca agaaagcatg caaggggatc aacctgatcg   1740
atgacatcaa gtactatttc gacgagaagg gcattatgcg cacggggctt atctcatttg   1800
agaataacaa ttattacttc aatgagaacg gggaaatgca gtttgggtac atcaatattg   1860
aggacaagat gttctatttt ggcgaggatg gcgtcatgca gatcggggtg ttcaacaccc   1920
cagatggttt caagtatttc gcgcatcaga atacgctgga tgagaacttc gagggcgaat   1980
caatcaacta taccgggtgg ctggacctcg atgagaagcg ctactatttc acggacgaat   2040
acattgcggc caccggctca gtcatcattg atggcgagga atactatttc gaccctgata   2100
cggcgcagct ggtgatcagt gagtaatgac ctagctgata acctagcccg cctaatgagc   2160
gggctttttt ttctcggcct aggtttcacc tgttctatta ggtgttacat gctgttcatc   2220
tgttacattg tcgatctgtt catggtgaac agctttaaat gcaccaaaaa ctcgtaaaag   2280
ctctgatgta tctatctttt ttacaccgtt ttcatctgtg catatggaca gttttccctt   2340
tgatatctaa cggtgaacag ttgttctact tttgtttgtt agtcttgatg cttcactgat   2400
agatacaaga gccataagaa cctcagatcc ttccgtattt agccagtatg ttctctagtg   2460
tggttcgttg tttttgcgtg agccatgaga acgaaccatt gagatcatgc ttactttgca   2520
tgtcactcaa aaattttgcc tcaaaactgg tgagctgaat tttgcagtt aaagcatcgt    2580
gtagtgtttt tcttagtccg ttacgtaggt aggaatctga tgtaatggtt gttggtattt   2640
tgtcaccatt catttttatc tggttgttct caagttcggt tacgagatcc atttgtctat   2700
ctagttcaac ttggaaaatc aacgtatcag tcgggcggcc tcgcttatca accaccaatt   2760
tcatattgct gtaagtgttt aaatctttac ttattggttt caaaacccat tggttaagcc   2820
ttttaaactc atggtagtta ttttcaagca ttaacatgaa cttaaattca tcaaggctaa   2880
tctctatatt tgccttgtga gttttctttt gtgttagttc ttttaataac cactcataaa   2940
tcctcataga gtatttgttt tcaaaagact taacatgttc cagattatat tttatgaatt   3000
tttttaactg gaaaagataa ggcaatatct cttcactaaa aactaattct aatttttcgc   3060
ttgagaactt ggcatagttt gtccactgga aaatctcaaa gcctttaacc aaaggattcc   3120
tgatttccac agttctcgtc atcagctctc tggttgcttt agctaataca ccataagcat   3180
tttccctact gatgttcatc atctgagcgt attggttata agtgaacgat accgtccgtt   3240
```

-continued

```
ctttccttgt agggttttca atcgtggggt tgagtagtgc cacacagcat aaaattagct   3300
tggtttcatg ctccgttaag tcatagcgac taatcgctag ttcatttgct ttgaaaacaa   3360
ctaattcaga catacatctc aattggtcta ggtgatttta atcactatac caattgagat   3420
gggctagtca atgataatta ctagctagtc cttttccttt gagttgtggg tatctgtaaa   3480
ttctgctaga cctttgctgg aaaacttgta aattctgcta gaccctctgt aaattccgct   3540
agacctttgt gtgttttttt tgtttatatt caagtggtta taatttatag aataaagaaa   3600
gaataaaaaa agataaaaag aatagatccc agccctgtgt ataactcact actttagtca   3660
gttccgcagt attacaaaag gatgtcgcaa acgctgtttg ctcctctaca aaacagacct   3720
taaaacccta aaggcttaag tagcaccctc gcaagctcgg gcaaatcgct gaatattcct   3780
tttgtctccg accatcaggc acctgagtcg ctgtcttttt cgtgacattc agttcgctgc   3840
gctcacggct ctggcagtga atgggggtaa atggcactac aggcgccttt tatggattca   3900
tgcaaggaaa ctacccataa tacaagaaaa gcccgtcacg ggcttctcag ggcgttttat   3960
ggcgggtctg ctatgtggtg ctatctgact ttttgctgtt cagcagttcc tgccctctga   4020
ttttccagtc tgaccacttc ggattatccc gtgacaggtc attcagactg gctaatgcac   4080
ccagtaaggc agcggtatca tcaacaggct tacccgtctt actgtcaacc ggatctaaaa   4140
cactaggccc aagagtttgt agaaacgcaa aaaggccatc cgtcaggatg gccttctgct   4200
taatttgatg cctggcagtt tatggcgggc gtcctgcccg ccaccctccg ggccgttgct   4260
tcgcaacgtt caaatccgct cccggcggat ttgtcctact caggagagcg ttcaccgaca   4320
aacaacagat aaaacgaaag gcccagtctt tcgactgagc ctttcgtttt atttgatgcc   4380
tggcagttcc ctactctcgc atggggagac cccacactac catcggcgct acggcgtttc   4440
acttctgagt tcggcatggg gtcaggtggg accaccgcgc tactgccgcc aggcaaattc   4500
tgttttatca gaccgcttct gcgttctgat ttaatctgta tcaggctgaa aatcttctct   4560
catccgccaa aacagccaag ctggatctaa aacactagct ctagctattg ttttaatgac   4620
aaatcagaac ggaatgtcat catcaaagtc catcggcggc tcgttagacg gcgctgccgg   4680
agcggactgc tgcgggcgag actgcgcgcc gccgctgaac tgattgccac cctgcggctg   4740
ctgaggctga ccccaaccgc cctgcggctg accaccaccg atattgccac ctgccggagc   4800
gccaccaccc tgacgaccac ccagcatctg catggtgccg ccaacgttca ccacgacttc   4860
tgtggtgtag cgatcctgac cggattgatc ggtccattta cgggtacgca gctgaccttc   4920
gatataaacc tgagaacctt tacgcagata ttcgctcgcc acttctgcca gtttgccgaa   4980
cagcacaacg cggtgccatt cagtctgttc tttcatctcg ccggtcgctt tatcacgcca   5040
ggattcggaa gtagccagcg taatgttggc aactgcgcca ccatttggca tgtagcgtac   5100
ttccgggtcc tgacccagat taccaacgag aataaccttg tttacgcctc tgctggccat   5160
gttcgtgtct cctgaaaaaa atcgttctga ataagtgtaa acgcgcgatt gtaccattac   5220
caatagcgct tttactatgt tgtgacctcg gttccgggaa acaaacctgg ccagacattg   5280
ttacacaaca ctccggataa tgcattccaa tactgtatat tcattcaggt caatcatatg   5340
aagggcgaat tctgcagata tccatcacac tggcggccgc cagtgtgatg gatatctgca   5400
gaattcgccc ttgagaagtt cctattctat atatagtata ggaacttctc tagaactttt   5460
gttacccgcc aaacaaaacc caaaaacaac ccatacccaa cccaataaaa caccaaaaca   5520
agacaaataa tcattgattg atggttgaaa tggggtaaac ttgacaaaca aacccactta   5580
```

```
aaacccaaaa catacccaaa cacacaccaa aaaaacacca taaggagttt tataaatgtt   5640
ggtattcatt gatgacggtt caacaaacat caaactacag tggcaggaaa gcgacggaac   5700
aattaaacag cacattagcc cgaacagctt caaacgcgag tgggcagtct cttttggtga   5760
taaaaaggtc tttaactaca cactgaacgg cgaacagtat tcatttgatc caatcagccc   5820
ggatgctgta gtcacaacca atatcgcatg gcaatacagc gacgttaatg tcgttgcagt   5880
gcatcacgcc ttactgacca gtggtctgcc ggtaagcgaa gtggatattg tttgcacact   5940
tcctctgaca gagtattacg acagaaataa ccaacccaat acggaaaata ttgagcgtaa   6000
gaaagcaaac ttccggaaaa aaattacatt aaatggcggg gatacattca caataaaaga   6060
tgtaaaagtc atgcctgaat ctataccggc aggttatgaa gttctacaag aactggatga   6120
gttagattct ttattaatta tagatctcgg gggcaccaca ttagatattt ctcaggtaat   6180
ggggaaatta tcggggatca gtaaaatata cggagactca tctcttggtg tctctctggt   6240
tacatctgca gtaaaagatg ccctttctct tgcgagaaca aaaggaagta gctatcttgc   6300
tgacgatata atcattcaca gaaaagataa taactatctg aagcaacgaa ttaatgatga   6360
gaacaaaata tcaatagtca ccgaagcaat gaatgaagca cttcgtaaac ttgagcaacg   6420
tgtattaaat acgctcaatg aattttctgg ttatactcat gttatggtta taggcggtgg   6480
cgcagaatta atatgcgatg cagtaaaaaa acacacacag attcgtgatg aacgtttttt   6540
caaaaccaat aactctcaat atgatttagt taacggtatg tatctcatag gtaattaatg   6600
atggacaagc gcagaaccat tgccttcaaa ctaaatccag atgtaaatca aacagataaa   6660
attgtttgtg atacactgga cagtatcccg caaggggaac gaagccgcct taaccgggcc   6720
gcactgacgg caggtctggc cttatacaga caagatcccc ggacccttt cctttatgt   6780
gagctgctga cgaaagaaac cacattttca gatatcgtga atatattgag atcgctattt   6840
ccaaaagaga tggccgattt taattcttca atagtcactc aatcctcttc acaacaagag   6900
caaaaaagtg atgaagagac caaaaaaaat gcgatgaagc taataaatta attcaattat   6960
tattgagttc cctttatcca ctatcaggct ggataaaggg aactcaatca agttattttc   7020
ttaccagtca ttacataatc gttattatga aataatcgtt tgcactgtct ctgttattca   7080
ggcaatttca ataaaggcac ttgctcacgc tctgtcattt tctgaaactc ttcatgctg    7139
```

```
<210> SEQ ID NO 12
<211> LENGTH: 536
<212> TYPE: PRT
<213> ORGANISM: artificial
<220> FEATURE:
<223> OTHER INFORMATION: synthetic

<400> SEQUENCE: 12

Met Thr Ser Gly Leu Ile Tyr Ile Asn Asp Ser Leu Tyr Tyr Phe Lys
1               5                   10                  15

Pro Pro Val Asn Asn Leu Ile Thr Gly Phe Val Thr Val Gly Asp Asp
            20                  25                  30

Lys Tyr Tyr Phe Asn Pro Ile Asn Gly Gly Ala Ala Ser Ile Gly Glu
        35                  40                  45

Thr Ile Ile Asp Asp Lys Asn Tyr Tyr Phe Asn Gln Ser Gly Val Leu
    50                  55                  60

Gln Thr Gly Val Phe Ser Thr Glu Asp Gly Phe Lys Tyr Phe Ala Pro
65                  70                  75                  80

Ala Asn Thr Leu Asp Glu Asn Leu Glu Gly Glu Ala Ile Asp Phe Thr
                85                  90                  95
```

```
Gly Lys Leu Ile Ile Asp Glu Asn Ile Tyr Tyr Phe Asp Asp Asn Tyr
            100                 105                 110

Arg Gly Ala Val Glu Trp Lys Glu Leu Asp Gly Glu Met His Tyr Phe
        115                 120                 125

Ser Pro Glu Thr Gly Lys Ala Phe Lys Gly Leu Asn Gln Ile Gly Asp
    130                 135                 140

Tyr Lys Tyr Tyr Phe Asn Ser Asp Gly Val Met Gln Lys Gly Phe Val
145                 150                 155                 160

Ser Ile Asn Asp Asn Lys His Tyr Phe Asp Asp Ser Gly Val Met Lys
                165                 170                 175

Val Gly Tyr Thr Glu Ile Asp Gly Lys His Phe Tyr Phe Ala Glu Asn
            180                 185                 190

Gly Glu Met Gln Ile Gly Val Phe Asn Thr Glu Asp Gly Phe Lys Tyr
        195                 200                 205

Phe Ala His His Asn Glu Asp Leu Gly Asn Glu Glu Gly Glu Glu Ile
    210                 215                 220

Ser Tyr Ser Gly Ile Leu Asn Phe Asn Asn Lys Ile Tyr Tyr Phe Asp
225                 230                 235                 240

Asp Ser Phe Thr Ala Val Val Gly Trp Lys Asp Leu Glu Asp Gly Ser
                245                 250                 255

Lys Tyr Tyr Phe Asp Glu Asp Thr Ala Glu Ala Tyr Ile Gly Leu Ser
            260                 265                 270

Leu Ile Asn Asp Gly Gln Tyr Tyr Phe Asn Asp Asp Gly Ile Met Gln
        275                 280                 285

Val Gly Phe Val Thr Ile Asn Asp Lys Val Phe Tyr Phe Ser Asp Ser
    290                 295                 300

Gly Ile Ile Glu Ser Gly Val Gln Asn Ile Asp Asp Asn Tyr Phe Tyr
305                 310                 315                 320

Ile Asp Asp Asn Gly Ile Val Gln Ile Gly Val Phe Asp Thr Ser Asp
                325                 330                 335

Gly Tyr Lys Tyr Phe Ala Pro Ala Asn Thr Val Asn Asp Asn Ile Tyr
            340                 345                 350

Gly Gln Ala Val Glu Tyr Ser Gly Leu Val Arg Val Gly Glu Asp Val
        355                 360                 365

Tyr Tyr Phe Gly Glu Thr Tyr Thr Ile Glu Thr Gly Trp Ile Tyr Asp
    370                 375                 380

Met Glu Asn Glu Ser Asp Lys Tyr Tyr Phe Asn Pro Glu Thr Lys Lys
385                 390                 395                 400

Ala Cys Lys Gly Ile Asn Leu Ile Asp Asp Ile Lys Tyr Tyr Phe Asp
                405                 410                 415

Glu Lys Gly Ile Met Arg Thr Gly Leu Ile Ser Phe Glu Asn Asn Asn
            420                 425                 430

Tyr Tyr Phe Asn Glu Asn Gly Glu Met Gln Phe Gly Tyr Ile Asn Ile
        435                 440                 445

Glu Asp Lys Met Phe Tyr Phe Gly Glu Asp Gly Val Met Gln Ile Gly
    450                 455                 460

Val Phe Asn Thr Pro Asp Gly Phe Lys Tyr Phe Ala His Gln Asn Thr
465                 470                 475                 480

Leu Asp Glu Asn Phe Glu Gly Glu Ser Ile Asn Tyr Thr Gly Trp Leu
                485                 490                 495

Asp Leu Asp Glu Lys Arg Tyr Tyr Phe Thr Asp Glu Tyr Ile Ala Ala
            500                 505                 510
```

Thr Gly Ser Val Ile Ile Asp Gly Glu Glu Tyr Tyr Phe Asp Pro Asp
        515                 520                 525

Thr Ala Gln Leu Val Ile Ser Glu
    530                 535

<210> SEQ ID NO 13
<211> LENGTH: 1102
<212> TYPE: DNA
<213> ORGANISM: Salmonella enterica Typhi

<400> SEQUENCE: 13
ggaggtaata ggtaagaata ctttataaaa caggtactta attgcaattt atatatttaa 60
agaggcaaat gattatgacc ggaatatttg cagaacaaac tgtagaggta gttaaaagcg 120
cgatcgaaac cgcagatggg gcattagatc tttataacaa atacctcgac caggtcatcc 180
cctggaagac ctttgatgaa accataaaag agttaagccg ttttaaacag gagtactcgc 240
aggaagcttc tgttttagtt ggtgatatta aagttttgct tatggacagc caggacaagt 300
attttgaagc gacacaaact gtttatgaat ggtgtggtgt cgtgacgcaa ttactctcag 360
cgtatatttt actatttgat gaatataatg agaaaaaagc atcagcccag aaagacattc 420
tcattaggat attagatgat ggtgtcaaga aactgaatga agcgcaaaaa tctctcctga 480
caagttcaca aagtttcaac aacgcttccg gaaaactgct ggcattagat agccagttaa 540
ctaatgattt ttcggaaaaa agtagttatt tccagtcaca ggtggataga attcgtaagg 600
aagcttatgc cggtgctgca gccggcatag tcgccggtcc gtttggatta attatttcct 660
attctattgc tgcgggcgtg attgaaggga aattgattcc agaattgaat aacaggctaa 720
aaacagtgca aaatttcttt actagcttat cagctacagt gaaacaagcg aataaagata 780
tcgatgcggc aaaattgaaa ttagccactg aaatagcagc aattggggag ataaaaacgg 840
aaaccgaaac aaccagattc tacgttgatt atgatgattt aatgctttct ttattaaaag 900
gagctgcaaa gaaaatgatt aacacctgta atgaatacca acaaagacac ggtaagaaga 960
cgcttttcga ggttcctgac gtctgataca ttttcattcg atctgtgtac ttttaacgcc 1020
cgatagcgta aagaaaatga gagacggaga aaaagcgata ttcaacagcc cgataaacaa 1080
gagtcgttac cgggctgacg ag 1102

<210> SEQ ID NO 14
<211> LENGTH: 303
<212> TYPE: PRT
<213> ORGANISM: Salmonella enterica Thyphi

<400> SEQUENCE: 14

Met Thr Gly Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln

-continued

```
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Phe Glu Val Pro Asp Val
    290                 295                 300


<210> SEQ ID NO 15
<211> LENGTH: 879
<212> TYPE: PRT
<213> ORGANISM: Clostridium difficile

<400> SEQUENCE: 15

Gly Leu Ile Asn Ile Asn Asn Ser Leu Phe Tyr Phe Asp Pro Ile Glu
1               5                   10                  15

Phe Asn Leu Val Thr Gly Trp Gln Thr Ile Asn Gly Lys Lys Tyr Tyr
            20                  25                  30

Phe Asp Ile Asn Thr Gly Ala Ala Leu Thr Ser Tyr Lys Ile Ile Asn
        35                  40                  45

Gly Lys His Phe Tyr Phe Asn Asn Asp Gly Val Met Gln Leu Gly Val
    50                  55                  60

Phe Lys Gly Pro Asp Gly Phe Glu Tyr Phe Ala Pro Ala Asn Thr Gln
65                  70                  75                  80

Asn Asn Asn Ile Glu Gly Gln Ala Ile Val Tyr Gln Ser Lys Phe Leu
                85                  90                  95

Thr Leu Asn Gly Lys Lys Tyr Tyr Phe Asp Asn Asn Ser Lys Ala Val
            100                 105                 110

Thr Gly Trp Arg Ile Ile Asn Asn Glu Lys Tyr Tyr Phe Asn Pro Asn
        115                 120                 125

Asn Ala Ile Ala Ala Val Gly Leu Gln Val Ile Asp Asn Asn Lys Tyr
    130                 135                 140

Tyr Phe Asn Pro Asp Thr Ala Ile Ile Ser Lys Gly Trp Gln Thr Val
145                 150                 155                 160

Asn Gly Ser Arg Tyr Tyr Phe Asp Thr Asp Thr Ala Ile Ala Phe Asn
                165                 170                 175
```

-continued

```
Gly Tyr Lys Thr Ile Asp Gly Lys His Phe Tyr Phe Asp Ser Asp Cys
            180                 185                 190

Val Val Lys Ile Gly Val Phe Ser Thr Ser Asn Gly Phe Glu Tyr Phe
        195                 200                 205

Ala Pro Ala Asn Thr Tyr Asn Asn Asn Ile Glu Gly Gln Ala Ile Val
    210                 215                 220

Tyr Gln Ser Lys Phe Leu Thr Leu Asn Gly Lys Lys Tyr Tyr Phe Asp
225                 230                 235                 240

Asn Asn Ser Lys Ala Val Thr Gly Leu Gln Thr Ile Asp Ser Lys Lys
                245                 250                 255

Tyr Tyr Phe Asn Thr Asn Thr Ala Glu Ala Ala Thr Gly Trp Gln Thr
            260                 265                 270

Ile Asp Gly Lys Lys Tyr Tyr Phe Asn Thr Asn Thr Ala Glu Ala Ala
        275                 280                 285

Thr Gly Trp Gln Thr Ile Asp Gly Lys Lys Tyr Tyr Phe Asn Thr Asn
    290                 295                 300

Thr Ala Ile Ala Ser Thr Gly Tyr Thr Ile Ile Asn Gly Lys His Phe
305                 310                 315                 320

Tyr Phe Asn Thr Asp Gly Ile Met Gln Ile Gly Val Phe Lys Gly Pro
                325                 330                 335

Asn Gly Phe Glu Tyr Phe Ala Pro Ala Asn Thr Asp Ala Asn Asn Ile
            340                 345                 350

Glu Gly Gln Ala Ile Leu Tyr Gln Asn Glu Phe Leu Thr Leu Asn Gly
        355                 360                 365

Lys Lys Tyr Tyr Phe Gly Ser Asp Ser Lys Ala Val Thr Gly Trp Arg
    370                 375                 380

Ile Ile Asn Asn Lys Lys Tyr Tyr Phe Asn Pro Asn Asn Ala Ile Ala
385                 390                 395                 400

Ala Ile His Leu Cys Thr Ile Asn Asn Asp Lys Tyr Tyr Phe Ser Tyr
                405                 410                 415

Asp Gly Ile Leu Gln Asn Gly Tyr Ile Thr Ile Glu Arg Asn Asn Phe
            420                 425                 430

Tyr Phe Asp Ala Asn Asn Glu Ser Lys Met Val Thr Gly Val Phe Lys
        435                 440                 445

Gly Pro Asn Gly Phe Glu Tyr Phe Ala Pro Ala Asn Thr His Asn Asn
    450                 455                 460

Asn Ile Glu Gly Gln Ala Ile Val Tyr Gln Asn Lys Phe Leu Thr Leu
465                 470                 475                 480

Asn Gly Lys Lys Tyr Tyr Phe Asp Asn Asp Ser Lys Ala Val Thr Gly
                485                 490                 495

Trp Gln Thr Ile Asp Gly Lys Lys Tyr Tyr Phe Asn Leu Asn Thr Ala
            500                 505                 510

Glu Ala Ala Thr Gly Trp Gln Thr Ile Asp Gly Lys Lys Tyr Tyr Phe
        515                 520                 525

Asn Leu Asn Thr Ala Glu Ala Ala Thr Gly Trp Gln Thr Ile Asp Gly
    530                 535                 540

Lys Lys Tyr Tyr Phe Asn Thr Asn Thr Phe Ile Ala Ser Thr Gly Tyr
545                 550                 555                 560

Thr Ser Ile Asn Gly Lys His Phe Tyr Phe Asn Thr Asp Gly Ile Met
                565                 570                 575

Gln Ile Gly Val Phe Lys Gly Pro Asn Gly Phe Glu Tyr Phe Ala Pro
            580                 585                 590

Ala Asn Thr Asp Ala Asn Asn Ile Glu Gly Gln Ala Ile Leu Tyr Gln
```

```
        595                 600                 605

Asn Lys Phe Leu Thr Leu Asn Gly Lys Lys Tyr Tyr Phe Gly Ser Asp
    610                 615                 620

Ser Lys Ala Val Thr Gly Leu Arg Thr Ile Asp Gly Lys Lys Tyr Tyr
625                 630                 635                 640

Phe Asn Thr Asn Thr Ala Val Ala Val Thr Gly Trp Gln Thr Ile Asn
                645                 650                 655

Gly Lys Lys Tyr Tyr Phe Asn Thr Asn Thr Ser Ile Ala Ser Thr Gly
            660                 665                 670

Tyr Thr Ile Ile Ser Gly Lys His Phe Tyr Phe Asn Thr Asp Gly Ile
        675                 680                 685

Met Gln Ile Gly Val Phe Lys Gly Pro Asp Gly Phe Glu Tyr Phe Ala
    690                 695                 700

Pro Ala Asn Thr Asp Ala Asn Asn Ile Glu Gly Gln Ala Ile Arg Tyr
705                 710                 715                 720

Gln Asn Arg Phe Leu Tyr Leu His Asp Asn Ile Tyr Tyr Phe Gly Asn
                725                 730                 735

Asn Ser Lys Ala Ala Thr Gly Trp Val Thr Ile Asp Gly Asn Arg Tyr
            740                 745                 750

Tyr Phe Glu Pro Asn Thr Ala Met Gly Ala Asn Gly Tyr Lys Thr Ile
        755                 760                 765

Asp Asn Lys Asn Phe Tyr Phe Arg Asn Gly Leu Pro Gln Ile Gly Val
    770                 775                 780

Phe Lys Gly Ser Asn Gly Phe Glu Tyr Phe Ala Pro Ala Asn Thr Asp
785                 790                 795                 800

Ala Asn Asn Ile Glu Gly Gln Ala Ile Arg Tyr Gln Asn Arg Phe Leu
                805                 810                 815

His Leu Leu Gly Lys Ile Tyr Tyr Phe Gly Asn Asn Ser Lys Ala Val
            820                 825                 830

Thr Gly Trp Gln Thr Ile Asn Gly Lys Val Tyr Tyr Phe Met Pro Asp
        835                 840                 845

Thr Ala Met Ala Ala Ala Gly Gly Leu Phe Glu Ile Asp Gly Val Ile
    850                 855                 860

Tyr Phe Phe Gly Val Asp Gly Val Lys Ala Pro Gly Ile Tyr Gly
865                 870                 875
```

<210> SEQ ID NO 16
<211> LENGTH: 879
<212> TYPE: PRT
<213> ORGANISM: Clostridium difficile

<400> SEQUENCE: 16

```
Gly Leu Ile Asn Ile Asn Asn Ser Leu Phe Tyr Phe Asp Pro Ile Glu
1               5                   10                  15

Ser Asn Leu Val Thr Gly Trp Gln Thr Ile Asn Gly Lys Lys Tyr Tyr
            20                  25                  30

Phe Asp Ile Asn Thr Gly Ala Ala Ser Thr Ser Tyr Lys Ile Ile Asn
        35                  40                  45

Gly Lys His Phe Tyr Phe Asn Asn Asn Gly Val Met Gln Leu Gly Val
    50                  55                  60

Phe Lys Gly Pro Asp Gly Phe Glu Tyr Phe Ala Pro Ala Asn Thr Gln
65                  70                  75                  80

Asn Asn Asn Ile Glu Gly Gln Ala Ile Val Tyr Gln Ser Lys Phe Leu
                85                  90                  95
```

-continued

```
Thr Leu Asn Gly Lys Lys Tyr Tyr Phe Asp Asn Asp Ser Lys Ala Val
            100                 105                 110

Thr Gly Trp Arg Ile Ile Asn Asn Glu Lys Tyr Tyr Phe Asn Pro Asn
        115                 120                 125

Asn Ala Ile Ala Ala Val Gly Leu Gln Val Ile Asp Asn Asn Lys Tyr
    130                 135                 140

Tyr Phe Asn Pro Asp Thr Ala Ile Ile Ser Lys Gly Trp Gln Thr Val
145                 150                 155                 160

Asn Gly Ser Arg Tyr Tyr Phe Asp Thr Asp Thr Ala Ile Ala Phe Asn
                165                 170                 175

Gly Tyr Lys Thr Ile Asp Gly Lys His Phe Tyr Phe Asp Ser Asp Cys
            180                 185                 190

Val Val Lys Ile Gly Val Phe Ser Gly Ser Asn Gly Phe Glu Tyr Phe
        195                 200                 205

Ala Pro Ala Asn Thr Tyr Asn Asn Asn Ile Glu Gly Gln Ala Ile Val
    210                 215                 220

Tyr Gln Ser Lys Phe Leu Thr Leu Asn Gly Lys Lys Tyr Tyr Phe Asp
225                 230                 235                 240

Asn Asn Ser Lys Ala Val Thr Gly Trp Gln Thr Ile Asp Ser Lys Lys
                245                 250                 255

Tyr Tyr Phe Asn Thr Asn Thr Ala Glu Ala Ala Thr Gly Trp Gln Thr
            260                 265                 270

Ile Asp Gly Lys Lys Tyr Tyr Phe Asn Thr Asn Thr Ala Glu Ala Ala
        275                 280                 285

Thr Gly Trp Gln Thr Ile Asp Gly Lys Lys Tyr Tyr Phe Asn Thr Asn
    290                 295                 300

Thr Ser Ile Ala Ser Thr Gly Tyr Thr Ile Ile Asn Gly Lys Tyr Phe
305                 310                 315                 320

Tyr Phe Asn Thr Asp Gly Ile Met Gln Ile Gly Val Phe Lys Val Pro
                325                 330                 335

Asn Gly Phe Glu Tyr Phe Ala Pro Ala Asn Thr His Asn Asn Asn Ile
            340                 345                 350

Glu Gly Gln Ala Ile Leu Tyr Gln Asn Lys Phe Leu Thr Leu Asn Gly
        355                 360                 365

Lys Lys Tyr Tyr Phe Gly Ser Asp Ser Lys Ala Ile Thr Gly Trp Gln
    370                 375                 380

Thr Ile Asp Gly Lys Lys Tyr Tyr Phe Asn Pro Asn Asn Ala Ile Ala
385                 390                 395                 400

Ala Thr His Leu Cys Thr Ile Asn Asn Asp Lys Tyr Tyr Phe Ser Tyr
                405                 410                 415

Asp Gly Ile Leu Gln Asn Gly Tyr Ile Thr Ile Glu Arg Asn Asn Phe
            420                 425                 430

Tyr Phe Asp Ala Asn Asn Glu Ser Lys Met Val Thr Gly Val Phe Lys
        435                 440                 445

Gly Pro Asn Gly Phe Glu Tyr Phe Ala Pro Ala Asn Thr His Asn Asn
    450                 455                 460

Asn Ile Glu Gly Gln Ala Ile Val Tyr Gln Asn Lys Phe Leu Thr Leu
465                 470                 475                 480

Asn Gly Lys Lys Tyr Tyr Phe Asp Asn Asp Ser Lys Ala Val Thr Gly
                485                 490                 495

Trp Gln Thr Ile Asp Ser Lys Lys Tyr Tyr Phe Asn Leu Asn Thr Ala
            500                 505                 510

Val Ala Val Thr Gly Trp Gln Thr Ile Asp Gly Glu Lys Tyr Tyr Phe
```

```
        515                 520                 525

Asn Leu Asn Thr Ala Glu Ala Ala Thr Gly Trp Gln Thr Ile Asp Gly
    530                 535                 540

Lys Arg Tyr Tyr Phe Asn Thr Asn Thr Tyr Ile Ala Ser Thr Gly Tyr
545                 550                 555                 560

Thr Ile Ile Asn Gly Lys His Phe Tyr Phe Asn Thr Asp Gly Ile Met
                565                 570                 575

Gln Ile Gly Val Phe Lys Gly Pro Asp Gly Phe Glu Tyr Phe Ala Pro
            580                 585                 590

Ala Asn Thr His Asn Asn Asn Ile Glu Gly Gln Ala Ile Leu Tyr Gln
        595                 600                 605

Asn Lys Phe Leu Thr Leu Asn Gly Lys Lys Tyr Tyr Phe Gly Ser Asp
    610                 615                 620

Ser Lys Ala Val Thr Gly Leu Arg Thr Ile Asp Gly Lys Lys Tyr Tyr
625                 630                 635                 640

Phe Asn Thr Asn Thr Ala Val Ala Val Thr Gly Trp Gln Thr Ile Asn
                645                 650                 655

Gly Lys Lys Tyr Tyr Phe Asn Thr Asn Thr Tyr Ile Ala Ser Thr Gly
            660                 665                 670

Tyr Thr Ile Ile Ser Gly Lys His Phe Tyr Phe Asn Thr Asp Gly Ile
        675                 680                 685

Met Gln Ile Gly Val Phe Lys Gly Pro Asp Gly Phe Glu Tyr Phe Ala
    690                 695                 700

Pro Ala Asn Thr Asp Ala Asn Asn Ile Glu Gly Gln Ala Ile Arg Tyr
705                 710                 715                 720

Gln Asn Arg Phe Leu Tyr Leu His Asp Asn Ile Tyr Tyr Phe Gly Asn
                725                 730                 735

Asp Ser Lys Ala Ala Thr Gly Trp Ala Thr Ile Asp Gly Asn Arg Tyr
            740                 745                 750

Tyr Phe Glu Pro Asn Thr Ala Met Gly Ala Asn Gly Tyr Lys Thr Ile
        755                 760                 765

Asp Asn Lys Asn Phe Tyr Phe Arg Asn Gly Leu Pro Gln Ile Gly Val
    770                 775                 780

Phe Lys Gly Pro Asn Gly Phe Glu Tyr Phe Ala Pro Ala Asn Thr Asp
785                 790                 795                 800

Ala Asn Asn Ile Asp Gly Gln Ala Ile Arg Tyr Gln Asn Arg Phe Leu
                805                 810                 815

His Leu Leu Gly Lys Ile Tyr Tyr Phe Gly Asn Asn Ser Lys Ala Val
            820                 825                 830

Thr Gly Trp Gln Thr Ile Asn Ser Lys Val Tyr Tyr Phe Met Pro Asp
        835                 840                 845

Thr Ala Met Ala Ala Ala Gly Gly Leu Phe Glu Ile Asp Gly Val Ile
    850                 855                 860

Tyr Phe Phe Gly Val Asp Gly Val Lys Ala Pro Gly Ile Tyr Gly
865                 870                 875
```

<210> SEQ ID NO 17
<211> LENGTH: 879
<212> TYPE: PRT
<213> ORGANISM: Clostridium difficile

<400> SEQUENCE: 17

```
Gly Leu Ile Asn Ile Asn Asn Ser Leu Phe Tyr Phe Asp Pro Ile Glu
1               5                   10                  15
```

-continued

```
Phe Asn Leu Val Thr Gly Trp Gln Thr Ile Asn Gly Lys Lys Tyr Tyr
            20                  25                  30

Phe Asp Ile Asn Thr Gly Ala Ala Leu Ile Ser Tyr Lys Ile Ile Asn
        35                  40                  45

Gly Lys His Phe Tyr Phe Asn Asn Asp Gly Val Met Gln Leu Gly Val
    50                  55                  60

Phe Lys Gly Pro Asp Gly Phe Glu Tyr Phe Ala Pro Ala Asn Thr Gln
65                  70                  75                  80

Asn Asn Asn Ile Glu Gly Gln Ala Ile Val Tyr Gln Ser Lys Phe Leu
                85                  90                  95

Thr Leu Asn Gly Lys Lys Tyr Tyr Phe Asp Asn Asp Ser Lys Ala Val
            100                 105                 110

Thr Gly Trp Arg Ile Ile Asn Asn Glu Lys Tyr Tyr Phe Asn Pro Asn
        115                 120                 125

Asn Ala Ile Ala Ala Val Gly Leu Gln Val Ile Asp Asn Asn Lys Tyr
    130                 135                 140

Tyr Phe Asn Pro Asp Thr Ala Ile Ile Ser Lys Gly Trp Gln Thr Val
145                 150                 155                 160

Asn Gly Ser Arg Tyr Tyr Phe Asp Thr Asp Thr Ala Ile Ala Phe Asn
                165                 170                 175

Gly Tyr Lys Thr Ile Asp Gly Lys His Phe Tyr Phe Asp Ser Asp Cys
            180                 185                 190

Val Val Lys Ile Gly Val Phe Ser Thr Ser Asn Gly Phe Glu Tyr Phe
        195                 200                 205

Ala Pro Ala Asn Thr Tyr Asn Asn Asn Ile Glu Gly Gln Ala Ile Val
    210                 215                 220

Tyr Gln Ser Lys Phe Leu Thr Leu Asn Gly Lys Lys Tyr Tyr Phe Asp
225                 230                 235                 240

Asn Asn Ser Lys Ala Val Thr Gly Trp Gln Thr Ile Asp Ser Lys Lys
                245                 250                 255

Tyr Tyr Phe Asn Thr Asn Thr Ala Glu Ala Ala Thr Gly Trp Gln Thr
            260                 265                 270

Ile Asp Gly Lys Lys Tyr Tyr Phe Asn Thr Asn Thr Ala Glu Ala Ala
        275                 280                 285

Thr Gly Trp Gln Thr Ile Asp Gly Lys Lys Tyr Tyr Phe Asn Thr Asn
    290                 295                 300

Thr Ala Ile Ala Ser Thr Gly Tyr Thr Ile Ile Asn Gly Lys His Phe
305                 310                 315                 320

Tyr Phe Asn Thr Asp Gly Ile Met Gln Ile Gly Val Phe Lys Gly Pro
                325                 330                 335

Asn Gly Phe Glu Tyr Phe Ala Pro Ala Asn Thr Asp Ala Asn Asn Ile
            340                 345                 350

Glu Gly Gln Ala Ile Leu Tyr Gln Asn Glu Phe Leu Thr Leu Asn Gly
        355                 360                 365

Lys Lys Tyr Tyr Phe Gly Ser Asp Ser Lys Ala Val Thr Gly Trp Arg
    370                 375                 380

Ile Ile Asn Asn Lys Lys Tyr Tyr Phe Asn Pro Asn Asn Ala Ile Ala
385                 390                 395                 400

Ala Ile His Leu Cys Thr Ile Asn Asn Asp Lys Tyr Tyr Phe Ser Tyr
                405                 410                 415

Asp Gly Ile Leu Gln Asn Gly Tyr Ile Thr Ile Glu Arg Asn Asn Phe
            420                 425                 430
```

-continued

```
Tyr Phe Asp Ala Asn Asn Glu Ser Lys Met Val Thr Gly Val Phe Lys
        435                 440                 445

Gly Pro Asn Gly Phe Glu Tyr Phe Ala Pro Ala Asn Thr His Asn Asn
    450                 455                 460

Asn Ile Glu Gly Gln Ala Ile Val Tyr Gln Asn Lys Phe Leu Thr Leu
465                 470                 475                 480

Asn Gly Lys Lys Tyr Tyr Phe Asp Asn Asp Ser Lys Ala Val Thr Gly
                485                 490                 495

Trp Gln Thr Ile Asp Gly Lys Lys Tyr Tyr Phe Asn Leu Asn Thr Ala
            500                 505                 510

Glu Ala Ala Thr Gly Trp Gln Thr Ile Asp Gly Lys Lys Tyr Tyr Phe
        515                 520                 525

Asn Leu Asn Thr Ala Glu Ala Ala Thr Gly Trp Gln Thr Ile Asp Gly
    530                 535                 540

Lys Lys Tyr Tyr Phe Asn Thr Asn Thr Phe Ile Ala Ser Thr Gly Tyr
545                 550                 555                 560

Thr Ser Ile Asn Gly Lys His Phe Tyr Phe Asn Thr Asp Gly Ile Met
                565                 570                 575

Gln Ile Gly Val Phe Lys Gly Pro Asn Gly Phe Glu Tyr Phe Ala Pro
            580                 585                 590

Ala Asn Thr His Asn Asn Asn Ile Glu Gly Gln Ala Ile Leu Tyr Gln
        595                 600                 605

Asn Lys Phe Leu Thr Leu Asn Gly Lys Lys Tyr Tyr Phe Gly Ser Asp
    610                 615                 620

Ser Lys Ala Val Thr Gly Leu Arg Thr Ile Asp Gly Lys Lys Tyr Tyr
625                 630                 635                 640

Phe Asn Thr Asn Thr Ala Val Ala Val Thr Gly Trp Gln Thr Ile Asn
                645                 650                 655

Gly Lys Lys Tyr Tyr Phe Asn Thr Asn Thr Ser Ile Ala Ser Thr Gly
            660                 665                 670

Tyr Thr Ile Ile Ser Gly Lys His Phe Tyr Phe Asn Thr Asp Gly Ile
        675                 680                 685

Met Gln Ile Gly Val Phe Lys Gly Pro Asp Gly Phe Glu Tyr Phe Ala
    690                 695                 700

Pro Ala Asn Thr Asp Ala Asn Asn Ile Glu Gly Gln Ala Ile Arg Tyr
705                 710                 715                 720

Gln Asn Arg Phe Leu Tyr Leu His Asp Asn Ile Tyr Tyr Phe Gly Asn
                725                 730                 735

Asn Ser Lys Ala Ala Thr Gly Trp Val Thr Ile Asp Gly Asn Arg Tyr
            740                 745                 750

Tyr Phe Glu Pro Asn Thr Ala Met Gly Ala Asn Gly Tyr Lys Thr Ile
        755                 760                 765

Asp Asn Lys Asn Phe Tyr Phe Arg Asn Gly Leu Pro Gln Ile Gly Val
    770                 775                 780

Phe Lys Gly Ser Asn Gly Phe Glu Tyr Phe Ala Pro Ala Asn Thr Asp
785                 790                 795                 800

Ala Asn Asn Ile Glu Gly Gln Ala Ile Arg Tyr Gln Asn Arg Phe Leu
                805                 810                 815

His Leu Leu Gly Lys Ile Tyr Tyr Phe Gly Asn Asn Ser Lys Ala Val
            820                 825                 830

Thr Gly Trp Gln Thr Ile Asn Gly Lys Val Tyr Tyr Phe Met Pro Asp
        835                 840                 845
```

Thr Ala Met Ala Ala Ala Gly Gly Leu Phe Glu Ile Asp Gly Val Ile
850 855 860

Tyr Phe Phe Gly Val Asp Gly Val Lys Ala Pro Gly Ile Tyr Gly
865 870 875

<210> SEQ ID NO 18
<211> LENGTH: 533
<212> TYPE: PRT
<213> ORGANISM: Clostridium difficile

<400> SEQUENCE: 18

Gly Leu Val Tyr Ile Asn Asp Ser Leu Tyr Tyr Phe Lys Pro Pro Ile
1 5 10 15

Lys Asn Leu Ile Thr Gly Phe Thr Thr Ile Gly Asp Asp Lys Tyr Tyr
20 25 30

Phe Asn Pro Asp Asn Gly Gly Ala Ala Ser Val Gly Glu Thr Ile Ile
35 40 45

Asp Gly Lys Asn Tyr Tyr Phe Ser Gln Asn Gly Val Leu Gln Thr Gly
50 55 60

Val Phe Ser Thr Glu Asp Gly Phe Lys Tyr Phe Ala Pro Ala Asp Thr
65 70 75 80

Leu Asp Glu Asn Leu Glu Gly Glu Ala Ile Asp Phe Thr Gly Lys Leu
85 90 95

Thr Ile Asp Glu Asn Val Tyr Tyr Phe Gly Asp Asn Tyr Arg Ala Ala
100 105 110

Ile Glu Trp Gln Thr Leu Asp Asp Glu Val Tyr Tyr Phe Ser Thr Asp
115 120 125

Thr Gly Arg Ala Phe Lys Gly Leu Asn Gln Ile Gly Asp Asp Lys Phe
130 135 140

Tyr Phe Asn Ser Asp Gly Ile Met Gln Lys Gly Phe Val Asn Ile Asn
145 150 155 160

Asp Lys Thr Phe Tyr Phe Asp Asp Ser Gly Val Met Lys Ser Gly Tyr
165 170 175

Thr Glu Ile Asp Gly Lys Tyr Phe Tyr Phe Ala Glu Asn Gly Glu Met
180 185 190

Gln Ile Gly Val Phe Asn Thr Ala Asp Gly Phe Lys Tyr Phe Ala His
195 200 205

His Asp Glu Asp Leu Gly Asn Glu Glu Gly Glu Ala Leu Ser Tyr Ser
210 215 220

Gly Ile Leu Asn Phe Asn Asn Lys Ile Tyr Tyr Phe Asp Asp Ser Phe
225 230 235 240

Thr Ala Val Val Gly Trp Lys Asp Leu Glu Asp Gly Ser Lys Tyr Tyr
245 250 255

Phe Asp Glu Asp Thr Ala Glu Ala Tyr Ile Gly Ile Ser Ile Ile Asn
260 265 270

Asp Gly Lys Tyr Tyr Phe Asn Asp Ser Gly Ile Met Gln Ile Gly Phe
275 280 285

Val Thr Ile Asn Asn Glu Val Phe Tyr Phe Ser Asp Ser Gly Ile Val
290 295 300

Glu Ser Gly Met Gln Asn Ile Asp Asp Asn Tyr Phe Tyr Ile Asp Glu
305 310 315 320

Asn Gly Leu Val Gln Ile Gly Val Phe Asp Thr Ser Asp Gly Tyr Lys
325 330 335

Tyr Phe Ala Pro Ala Asn Thr Val Asn Asp Asn Ile Tyr Gly Gln Ala
340 345 350

-continued

```
Val Glu Tyr Ser Gly Leu Val Arg Val Gly Glu Asp Val Tyr Tyr Phe
        355                 360                 365

Gly Glu Thr Tyr Thr Ile Glu Thr Gly Trp Ile Tyr Asp Met Glu Asn
    370                 375                 380

Glu Ser Asp Lys Tyr Tyr Phe Asp Pro Glu Thr Lys Lys Ala Tyr Lys
385                 390                 395                 400

Gly Ile Asn Val Ile Asp Asp Ile Lys Tyr Tyr Phe Asp Glu Asn Gly
                405                 410                 415

Ile Met Arg Thr Gly Leu Ile Thr Phe Glu Asp Asn His Tyr Tyr Phe
            420                 425                 430

Asn Glu Asp Gly Ile Met Gln Tyr Gly Tyr Leu Asn Ile Glu Asp Lys
        435                 440                 445

Thr Phe Tyr Phe Ser Glu Asp Gly Ile Met Gln Ile Gly Val Phe Asn
    450                 455                 460

Thr Pro Asp Gly Phe Lys Tyr Phe Ala His Gln Asn Thr Leu Asp Glu
465                 470                 475                 480

Asn Phe Glu Gly Glu Ser Ile Asn Tyr Thr Gly Trp Leu Asp Leu Asp
                485                 490                 495

Glu Lys Arg Tyr Tyr Phe Thr Asp Glu Tyr Ile Ala Ala Thr Gly Ser
            500                 505                 510

Val Ile Ile Asp Gly Glu Glu Tyr Tyr Phe Asp Pro Asp Thr Ala Gln
        515                 520                 525

Leu Val Ile Ser Glu
    530


<210> SEQ ID NO 19
<211> LENGTH: 533
<212> TYPE: PRT
<213> ORGANISM: Clostridium difficile

<400> SEQUENCE: 19

Gly Leu Ile Tyr Ile Asn Asp Ser Leu Tyr Tyr Phe Lys Pro Pro Val
1               5                   10                  15

Asn Asn Leu Ile Thr Gly Phe Val Thr Val Gly Asp Asp Lys Tyr Tyr
            20                  25                  30

Phe Asn Pro Ile Asn Gly Gly Ala Ala Ser Ile Gly Glu Thr Ile Ile
        35                  40                  45

Asp Asp Lys Asn Tyr Tyr Phe Asn Gln Ser Gly Val Leu Gln Thr Gly
    50                  55                  60

Val Phe Ser Thr Glu Asp Gly Phe Lys Tyr Phe Ala Pro Ala Asn Thr
65                  70                  75                  80

Leu Asp Glu Asn Leu Glu Gly Glu Ala Ile Asp Phe Thr Gly Lys Leu
                85                  90                  95

Ile Ile Asp Glu Asn Ile Tyr Tyr Phe Asp Asp Asn Tyr Arg Gly Ala
            100                 105                 110

Val Glu Trp Lys Glu Leu Asp Gly Glu Met His Tyr Phe Ser Pro Glu
        115                 120                 125

Thr Gly Lys Ala Phe Lys Gly Leu Asn Gln Ile Gly Asp Tyr Lys Tyr
    130                 135                 140

Tyr Phe Asn Ser Asp Gly Val Met Gln Lys Gly Phe Val Ser Ile Asn
145                 150                 155                 160

Asp Asn Lys His Tyr Phe Asp Asp Ser Gly Val Met Lys Val Gly Tyr
                165                 170                 175

Thr Glu Ile Asp Gly Lys His Phe Tyr Phe Ala Glu Asn Gly Glu Met
            180                 185                 190
```

-continued

```
Gln Ile Gly Val Phe Asn Thr Glu Asp Gly Phe Lys Tyr Phe Ala His
        195                 200                 205

His Asn Glu Asp Leu Gly Asn Glu Glu Gly Glu Glu Ile Ser Tyr Ser
    210                 215                 220

Gly Ile Leu Asn Phe Asn Asn Lys Ile Tyr Tyr Phe Asp Asp Ser Phe
225                 230                 235                 240

Thr Ala Val Val Gly Trp Lys Asp Leu Glu Asp Gly Ser Lys Tyr Tyr
                245                 250                 255

Phe Asp Glu Asp Thr Ala Glu Ala Tyr Ile Gly Leu Ser Leu Ile Asn
            260                 265                 270

Asp Gly Gln Tyr Tyr Phe Asn Asp Asp Gly Ile Met Gln Val Gly Phe
        275                 280                 285

Val Thr Ile Asn Asp Lys Val Phe Tyr Phe Ser Asp Ser Gly Ile Ile
    290                 295                 300

Glu Ser Gly Val Gln Asn Ile Asp Asp Asn Tyr Phe Tyr Ile Asp Asp
305                 310                 315                 320

Asn Gly Ile Val Gln Ile Gly Val Phe Asp Thr Ser Asp Gly Tyr Lys
                325                 330                 335

Tyr Phe Ala Pro Ala Asn Thr Val Asn Asp Asn Ile Tyr Gly Gln Ala
            340                 345                 350

Val Glu Tyr Ser Gly Leu Val Arg Val Gly Glu Asp Val Tyr Tyr Phe
        355                 360                 365

Gly Glu Thr Tyr Thr Ile Glu Thr Gly Trp Ile Tyr Asp Met Glu Asn
    370                 375                 380

Glu Ser Asp Lys Tyr Tyr Phe Asn Pro Glu Thr Lys Lys Ala Cys Lys
385                 390                 395                 400

Gly Ile Asn Leu Ile Asp Asp Ile Lys Tyr Tyr Phe Asp Glu Lys Gly
                405                 410                 415

Ile Met Arg Thr Gly Leu Ile Ser Phe Glu Asn Asn Asn Tyr Tyr Phe
            420                 425                 430

Asn Glu Asn Gly Glu Met Gln Phe Gly Tyr Ile Asn Ile Glu Asp Lys
        435                 440                 445

Met Phe Tyr Phe Gly Glu Asp Gly Val Met Gln Ile Gly Val Phe Asn
    450                 455                 460

Thr Pro Asp Gly Phe Lys Tyr Phe Ala His Gln Asn Thr Leu Asp Glu
465                 470                 475                 480

Asn Phe Glu Gly Glu Ser Ile Asn Tyr Thr Gly Trp Leu Asp Leu Asp
                485                 490                 495

Glu Lys Arg Tyr Tyr Phe Thr Asp Glu Tyr Ile Ala Ala Thr Gly Ser
            500                 505                 510

Val Ile Ile Asp Gly Glu Glu Tyr Tyr Phe Asp Pro Asp Thr Ala Gln
        515                 520                 525

Leu Val Ile Ser Glu
    530
```

MULTIVALENT LIVE VECTOR VACCINE AGAINST *CLOSTRIDIUM DIFFICILE*-ASSOCIATED DISEASE

CROSS REFERENCE TO RELATED APPLICATIONS

This application is the U.S. National Stage under 35 U.S.C.§ 371 of International Application No.: PCT/US2010/056871, filed Nov. 16. 2010. which claims the benefit of U.S. Appl. No. 61/261,406, filed Nov. 16, 2009. The content of the aforesaid application is relied upon and incorporated by reference in its entirety.

STATEMENT OF FEDERALLY SPONSORED RESEARCH AND DEVELOPMENT

This invention was made with government support under Grant No. AI057168 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 108,528 Byte ASCII (Text) file named "SEQ_Listing.TXT," created on Nov. 16, 2010.

FIELD OF THE INVENTION

The field of the invention relates to vaccines. In particular, the field of the invention relates to therapies to treat and prevent *Clostridium difficile* infections (CDI), including recurrent infections in patients previously infected with *Clostridium difficile.*

BACKGROUND OF THE INVENTION

*C. difficile* is a rapidly emerging enteric pathogen which is now the leading cause of nosocomial infectious diarrhea in developed countries. Infections are caused by an anaerobic, spore-forming *bacillus* that often attacks elderly patients in various healthcare settings following treatment of unrelated infections with antibiotics (Blossom D B, McDonald L C. The challenges posed by reemerging *Clostridium difficile* infection. *Clin Infect Dis.* 2007; 45:222-227; Gould C V, McDonald L C. Bench-to-bedside review: *Clostridium difficile* colitis. *Crit. Care.* 2008; 12:203). Clinical symptoms range in severity from mild antibiotic-associated diarrhea to a more severe and life-threatening pseudomembranous colitis which if untreated leads to fulminant colitis and death. (Kelly C P, LaMont J T. *Clostridium difficile* infection. *Annu Rev Med.* 1998; 49:375-390). Deaths attributable to *C. difficile* disease have quadrupled in the United States from 5.7 per million persons in 1999 to 23.7 per million in 2004 (Redelings M D, Sorvillo F, Mascola L. Increase in *Clostridium difficile*-related mortality rates, United States, 1999-2004. *Emerg Infect Dis.* 2007; 13:1417-1419). Estimates of the cost for treatment for CDI in the United States have been dramatically revised upward from $1 billion in 2002 to $3.2 billion in 2007, due to a dramatic increase in the number of cases and increasing severity of the disease (O'Brien J A, Lahue B J, Caro J J, Davidson D M. The emerging infectious challenge of *Clostridium difficile*-associated disease in Massachusetts hospitals: clinical and economic consequences. *Infect Control Hosp Epidemiol.* 2007; 28:1219-1227). Rapidly emerging hypervirulent antibiotic-resistant strains of *C. difficile* have been associated with recent epidemics of CDI in North America and Europe with increased morbidity and mortality in healthcare settings (Warny M, Pepin J, Fang A et al. Toxin production by an emerging strain of *Clostridium difficile* associated with outbreaks of severe disease in North America and Europe. *Lancet.* 2005; 366:1079-1084). However, epidemic strains of *C. difficile* are being increasingly reported in community-acquired disease in which no previous history of antibiotic use was evident. Since epidemic strains of *C. difficile* spores have now been repeatedly detected in commercial beef, poultry, and other food products, increasing attention is now being focused on food products as one possible source of community infection (Rodriguez-Palacios A, Staempfli Duffield T, Weese J S. *Clostridium difficile* in retail ground meat, Canada. *Emerg Infect Dis.* 2007; 13:485-487). Although primary CDI can be successfully treated with metronidazole or vancomycin, recurrent episodes of antibiotic-resistant CDI complicate management, and development of a vaccine against infection with *Clostridium difficile* could be useful to prevent relapse (Musher D M, Nuila F, Logan N. The long-term outcome of treatment of *Clostridium difficile* colitis. *Clin Infect Dis.* 2007; 45:523-524).

One significant challenge in the management of CDI is successful treatment of recurrent disease after resolution of primary disease symptoms. Recurrent CDI (RCDI) typically occurs within 7 days to 3 weeks following cessation of antibiotic treatment for the initial episode. The most significant risk factor for recurrence is recurrence itself (Blossom D B, McDonald L C. The challenges posed by reemerging *Clostridium difficile* infection. *Clin Infect Dis.* 2007; 45:222-227). The risk of recurrent infection rises from about 20% after the primary infection to approximately 40% after the first recurrence, further increasing to >60% after two or more recurrences (Kelly C P, LaMont J T. *Clostridium difficile*—more difficult than ever. *N Engl J. Med.* 2008; 359:1932-1940). Epidemic strains of *C. difficile*, including PCR ribotypes 027 and 078, are associated with recurrence and increased severity of disease (Leav B A, Blair B, Leney M et al. Serum anti-toxin B antibody correlates with protection from recurrent *Clostridium difficile* infection (CDI). *Vaccine.* 2010; 28:965-969; Goorhuis A, Bakker D, Corver J et al. Emergence of *Clostridium difficile* infection due to a new hypervirulent strain, polymerase chain reaction ribotype 078. *Clin Infect Dis.* 2008; 47:1162-1170; Burns K, Morris-Downes M, Fawley W N, Smyth E, Wilcox M H, Fitzpatrick F. Infection due to *C. difficile* ribotype 078: first report of cases in the Republic of Ireland. *J Hosp Infect.* 2010; 75:287-291). In one recent study, these two ribotypes accounted for 54% of typeable isolates from recurrent CDI cases, and 34% of primary cases identified over a one month period (Burns K, Skally M, Solomon K et al. *Clostridium difficile* Infection in the Republic of Ireland: Results of a 1-Month National Surveillance and Ribotyping Project, March 2009. *Infect Control Hosp Epidemiol.* 2010). Other risk factors for RCDI include age >65 years, sever underlying illness, and continued use of antibiotics for unrelated disease after resolution of CDI; however, the coincidence of more than one of these factors dramatically increases the probability of recurrence (Kyne L, Wanly M, Qamar A, Kelly C P. Association between antibody response to toxin A and protection against recurrent *Clostridium difficile* diarrhoea. *Lancet.* 2001; 357:189-193; Hu M Y, Katchar K, Kyne L et al. Prospective derivation and validation of a clinical prediction rule for recurrent *Clostridium difficile* infection. *Gastroenterology.* 2009; 136:1206-1214).

The genome of *C. difficile* is highly dynamic, and recent studies point to multiple paths leading to the emergence of hypervirulence in epidemic strains (He M, Sebaihia M, Lawley T D et al., Evolutionary dynamics of *Clostridium difficile* over short and long time scales. *Proc Natl Acad Sci USA.* 2010; 107:7527-7532). Such genome fluidity suggests that modulation of virulence would be expected, with variation shaped through positive selection by host immunity as well as clinical pressures including routine antibiotic therapy (He M, Sebaihia M, Lawley T D et al. Evolutionary dynamics of *Clostridium difficile* over short and long time, scales. *Proc Natl Acad Sci USA.* 2010; 107:7527-7532; Stabler R A, He M, Dawson L et al. Comparative genome and phenotypic analysis of *Clostridium difficile* 027 strains provides insight into the evolution of a hypervirulent bacterium. *Genome Biol.* 2009; 10:R102; Stabler R A, Valiente E, Dawson L F, He M, Parkhill J, Wren B W. In-depth genetic analysis of *Clostridium difficile* PCR-ribotype 027 strains reveals high genome fluidity including point mutations and inversions. Gut Microbes. 2010; 1:1-8). Genome fluidity seems to explain the repeated isolation of clinical strains of *C. difficile* in which expected virulence factors are not always present.

Enterotoxins A (TcdA) and B (TcdB) are the primary virulence factors of *C. difficile*. These toxins are exoenzymes that monoglucosylate small Rho-like GTPases, ultimately leading to the disruption of the actin cytoskeleton of colonic intestinal epithelial cells, destruction of tight junctions, and apoptosis (Voth D E, Ballard J D. *Clostridium difficile* toxins: mechanism of action and role in disease. *Clin Microbiol Rev.* 2005; 18:247-263; Aktories K, Barbieri J T. Bacterial cytotoxins: targeting eukaryotic switches. *Nat Rev Microbiol.* 2005; 3:397-410). Release of cytokines from intoxicated target cells also leads to massive infiltration of neutrophils into damaged tissue regions, a hallmark of pseudomembranous colitis (Thielman Nathan M., Wilson Kenneth H. Antibiotic-Associated Colitis. In: Mandell G L, Bennett John E, Dolin R, eds. *Principles and Practice of Infectious Diseases.* 6 ed. Philadelphia: Elsevier Churchill Livingstone; 2005:1249-63). Both enterotoxins are not required to cause disease, and clinical strains in which TcdA is absent have been repeatedly isolated from patients (Kim S J, Kim H, Seo Y et al. Molecular characterization of toxin A-negative, toxin B-positive variant strains of *Clostridium difficile* isolated in Korea. *Diagn Microbiol Infect Dis.* 2010; 67:198-201; Pituch H, Brazier J S, Obuch-Woszczatynski P, Wultanska D, Meisel-Mikolajczyk F, Luczak M. Prevalence and association of PCR ribotypes of *Clostridium difficile* isolated from symptomatic patients from Warsaw with macrolide-lincosamide-streptogramin B (MLSB) type resistance. *J Med. Microbiol.* 2006; 55:207-213; Pituch H, van LW, Maquelin K et al. Toxin profiles and resistances to macrolides and newer fluoroquinolones as epidemicity determinants of clinical isolates of *Clostridium difficile* from Warsaw, Poland. *J Clin Microbiol.* 2007; 45:1607-1610). To date, all clinical isolates of *C. difficile* express TcdB, and TcdB is the only virulence factor suggested to be specifically required for manifestation of disease in humans (Lyras D, O'Connor J R, Howarth P M et al. Toxin B is essential for virulence of *Clostridium difficile. Nature.* 2009). Recent studies suggest that TcdB expressed by epidemic strains is hypertoxic due to an extended range of tissue tropism and increased penetration into the cytoplasm of target cells (Lanis J M, Barua S, Ballard J D. Variations in TcdB Activity and the Hypervirulence of Emerging Strains of *Clostridium difficile*. PLoS Pathog. 2010; 6:e1001061). However, epidemic strains of *C. difficile*, including PCR ribotypes 027 and 078, typically express both TcdA and TcdB, suggesting that co-expression of both toxins may play an important role in the severity of disease caused by these epidemic strains.

In addition to toxins A and B, PCR-ribotypes 027 and 078 also invariably carry an additional toxin affecting the actin cytoskeleton called *C. difficile* transferase (Cdt); this toxin has also been called binary toxin because it is composed of a catalytic A subunit and a cell-binding B subunit (Perelle S, Gibed M, Bourlioux P, Corthier G, Popoff M R. Production of a complete binary toxin (actin-specific ADP-ribosyltransferase) by *Clostridium difficile* CD196. *Infect Immun.* 1997; 65:1402-1407; Rupnik M, Grabnar M, Geric B. Binary toxin producing *Clostridium difficile* strains. *Anaerobe.* 2003; 9:289-294). The activity of Cdt causes rearrangement of the actin cytoskeleton of intestinal epithelial cells, disrupting tight junctions and allowing better penetration and binding of toxin B to basolateral receptors, possibly enhancing the virulence of epidemic strains (Carter G P, Rood J I, Lyras D. The role of toxin A and toxin B in *Clostridium difficile*-associated disease. *Gut Microbes.* 2010; 1:58-64). Surprisingly, it was recently discovered that Cdt also appears to enhance colonization of the intestinal tract by inducing microtubule-based protrusions which enhance the adherence of *C. difficile* (Schwan C, Stecher B, Tzivelekidis T et al. *Clostridium difficile* toxin CDT induces formation of microtubule-based protrusions and increases adherence of bacteria. *PLoS Pathog.* 2009; 5:e1000626).

Since antibiotic use is a major contributing factor to the occurrence of CDI, a non-antibiotic vaccine-based approach for preventing disease could potentially reduce patient morbidity and mortality due to recurrent infection following cessation of antibiotic treatment. Recent economic computer models strongly indicate that development of a vaccine against infection with *C. difficile* could be cost-effective over a wide range of vaccine efficacies and costs when used to prevent recurrent disease (Lee B Y, Popovich M J, Tian Y et al. The potential value of *Clostridium difficile* vaccine: an economic computer simulation model. Vaccine. 2010; 28:5245-5253). However, no such vaccine is currently on the market.

Reduced serum IgG antibody responses to *C. difficile* toxin A has been proposed as a risk factor linked to recurrence of infection with *C. difficile* (Kyne L, Wamy M, Qamar A, Kelly C P. Asymptomatic carriage of *Clostridium difficile* and serum levels of IgG antibody against toxin A. *N Engl J. Med.* 2000; 342:390-397; Aboudola S, Kotloff K L, Kyne L et al. *Clostridium difficile* vaccine and serum immunoglobulin G antibody response to toxin A. *Infect Immun.* 2003; 71:1608-1610), and evidence from a recent Phase 2 clinical trial indicates that lower serum concentrations of neutralizing antibody against both TcdA and TcdB are associated with recurrence of CDI (Leav B A, Blair B, Leney M et al. Serum anti-toxin B antibody correlates with protection from recurrent *Clostridium difficile* infection (CDI). *Vaccine.* 2010; 28:965-969). Additional data from a related Phase 2 trial showed that co-administration of antibiotics to patients with CDI, along with humanized IgG monoclonal antibodies neutralizing toxin A (CDA1) and toxin B (CDB1), provided significant protection against recurrent disease, with patients suffering from multiple recurrences being particularly likely to benefit (Lowy I, Molrine D C, Leav B A et al. Treatment with monoclonal antibodies against *Clostridium difficile* toxins. *N Engl J. Med.* 2010; 362:197-205). Sanofi-Aventis has conducted a series of Phase 1 clinical trials testing the immunogenicity of a 3 dose toxoid-based bivalent vaccine targeting both TcdA and TcdB from *C. difficile*; encouraging serum IgG titers against toxins A and B were observed for both healthy subjects (18-55 years of age) and elderly subjects (≥65), with seroconversion rates of 75% against TcdA and TcdB in both age groups after 3 intramuscular 50 μg doses of toxoid (Foglia, G. ACAM-CDIFFTM: An Active Vaccine Against *Clostridium difficile* Infection (CDI). 2010. Ref Type: Conference Proceeding). The mechanism(s) by which serum antibody responses are effective against infection and disease caused by *C. difficile* are unclear, although it has been proposed that entry of IgG antitoxin from the blood into mucosal tissues of the large bowel or intestinal lumen may prevent toxin binding (Kelly C P. Immune response to *Clostridium difficile* infection. *Eur J Gastroenterol Hepatol.* 1996; 8:1048-1053; Warny M, Vaerman J P, Avesani V, Delmee M. Human antibody response to *Clostridium difficile* toxin A in relation to clinical course of infection. *Infect Immun.* 1994; 62:384-389).

There is a need for new treatments against *C. difficile* infections, in particular, treatments aimed at preventing recurrent infections of *C. difficile* in patients. The present invention of a multivalent live *Salmonella enterica* serovar Typhi (*Salmonella Typhi; S. Typhi*) vector expressing various toxins from *Clostridium difficile* satisfies this need.

SUMMARY OF THE INVENTION

The invention provides a *Clostridium difficile* vaccine comprising a live *Salmonella Typhi* vector comprising the cell binding domain of *Clostridium difficile* toxin TcdA (CBD/A) or an antigenic fragment thereof and the cell binding domain of *Clostridium difficile* toxin TcdB (CBD/B) or an antigenic fragment thereof.

In another aspect, the invention further provides a *Clostridium difficile* vaccine comprising a *Salmonella Typhi* vector comprising the cell binding domains of the *Clostridium difficile* toxins TcdA (CBD/A) and TcdB (CBD/B) or antigenic fragments thereof, and additionally comprises the cell-binding subunit (CdtB) of the *Clostridium difficile* colonization factor binary toxin, or an antigenic fragment thereof.

In another aspect, the invention provides a *Clostridium difficile* vaccine comprising a *Salmonella Typhi* vector wherein domains of one or more of the TcdA (CBD/A) toxin, the TcdB (CBD/B) toxin and CdtB toxin are expressed on a non-antibiotic plasmid selection system in *Salmonella Typhi*. In some embodiments of the vaccine of the invention, the plasmid expresses a gene that is essential for the growth of *Salmonella Typhi*, and has necessarily also been deleted from the *Salmonella Typhi* chromosome. In some embodiments, the gene encodes single stranded binding protein (SSB).

In some aspects, the invention provides a *Clostridium difficile* vaccine comprising a *Salmonella Typhi* vector wherein synthetic genes encoding domains of one or more of the TcdA (CBD/A) toxin, the TcdB (CBD/B) toxin and CdtB toxin are chromosomally integrated into the genome of *Salmonella Typhi*. In some embodiments of the invention, the TcdB (CBD/B) toxin is expressed on a non-antibiotic plasmid expression system in *Salmonella Typhi*, and synthetic genes encoding domains of TcdA (CBD/A) and CdtB toxins are chromosomally integrated into the genome of *Salmonella Typhi*. In some embodiments, one or both synthetic genes encoding domains of TcdA (CBD/A) and CdtB are inserted into the guaBA locus of *Salmonella Typhi*. In some embodiments of the invention, synthetic genes encoding domains of either the TcdA (CBD/A) toxin or CdtB binary toxin is inserted into the guaBA locus of *S. Typhi* and the remaining gene is inserted into the htrA locus of *S. Typhi.*

In another aspect, the invention provides a *Clostridium difficile* vaccine comprising a *Salmonella Typhi* vector wherein domains of one or more of TcdA toxin protein (CBD/A), TcdB toxin protein (CBD/B) and CdtB binary toxin protein are fused to a cytolysin A (ClyA) protein from *Salmonella Typhi* to facilitate export of the toxin from the cell. In some embodiments, ClyA is mutated to reduce hemolytic activity of ClyA, while still retaining the ability to export the toxin from the cell. In one embodiment, the ClyA mutant is ClyA I198N. In another embodiment, the ClyA mutant is ClyA C285W.

In another aspect, the invention provides a *Clostridium difficile* vaccine comprising a *Salmonella Typhi* live vector wherein the nucleic acid sequences encoding non-toxic cell-binding domains of TcdA toxin (CBD/A), TcdB toxin (CBD/B) and CdtB or antigenic fragments thereof are genetically optimized for expression and stability in *Salmonella Typhi.*

In another aspect, the present invention is directed to methods of inducing an immune response against *Clostridium difficile* in a subject in need thereof, comprising administering to the subject an immunologically-effective amount of a *Salmonella Typhi* live vector of the invention.

In another aspect, the present invention is directed to methods of inducing an immune response against *Clostridium difficile* in a subject in need thereof, comprising administering to the subject an immunologically-effective amount of a *Salmonella Typhi* live vector of the invention as a prime, and subsequently administering a boost comprising a polypeptide selected from the group consisting of TcdA toxin (CBD/A) or an antigenic fragment thereof, TcdB toxin (CBD/B) or an antigenic fragment thereof, and CdtB or an antigenic fragment thereof, or combinations thereof.

In another aspect, the invention is directed to preventing recurrence of a *Clostridium difficile* infection in a subject in need thereof, comprising administering to the subject an immunologically-effective amount of a *Salmonella Typhi* live vector of the invention. In another aspect, the present invention is directed to preventing recurrence of a *Clostridium difficile* infection in a subject in need thereof, comprising administering to the subject an immunologically-effective amount of a *Salmonella Typhi* live vector of the invention as a prime, and subsequently administering a boost that comprises a polypeptide selected from the group consisting of TcdA toxin (CBD/A) or an antigenic fragment thereof, TcdB toxin (CBD/B) or an antigenic fragment thereof, and CdtB or an antigenic fragment thereof, or combinations thereof.

In some aspects of the invention, the *S. Typhi* live vector is administered mucosally.

DETAILED DESCRIPTION OF THE INVENTION

The present invention provides a multivalent vaccine to treat and/or prevent *Clostridium difficile* infection comprising a *Salmonella Typhi* live vector comprising the cell-binding domain of the TcdA toxin (CBD/A) of *Clostridium difficile* or an antigenic fragment thereof and the cell-binding domain of TcdB (CBD/B) toxin of *C. difficile* or an antigenic fragment thereof for eliciting a balanced and robust mucosal as well as serum neutralizing antibody response. In addition to targeting toxins A and B, in some aspects, the invention further provides a *S. Typhi* live vector that further comprises the cell-binding subunit of binary toxin, CdtB from *C. difficile* or an antigenic fragment thereof, thereby encompassing a trivalent live vector vaccine. Binary toxin may act to enhance the virulence of epidemic strains carrying all 3 toxins, including ribotypes 027 and 078, by promoting better colonization of *C. difficile* from germinating spores for delivering higher levels of the toxins while improving penetration and binding of TcdB. Without being bound by any particular theory as to how the invention works, the present invention is believed to encompass targeting live vector-mediated immunity against the actions of toxins A and B at two levels: 1] by blocking the binding of both toxins through targeting of serum and mucosal immunity to their cell-binding domains, and 2] reducing the binding of toxin B by maintaining the integrity of intestinal epithelial tissue through mucosal neutralization of the binding domain of CdtB. Neutralization of CdtB can also provide mucosal immunity against intestinal colonization and recurrent infection. In accordance with the embodiments of the invention, the cell binding domains of TcdA toxin (CBD/A), TcdB toxin (CBD/B), and/or CdtB can be expressed in *Salmonella Typhi* on a plasmid, chromosomally, or some combination of plasmid-based and chromosomalbased expression systems.

Figure 1:
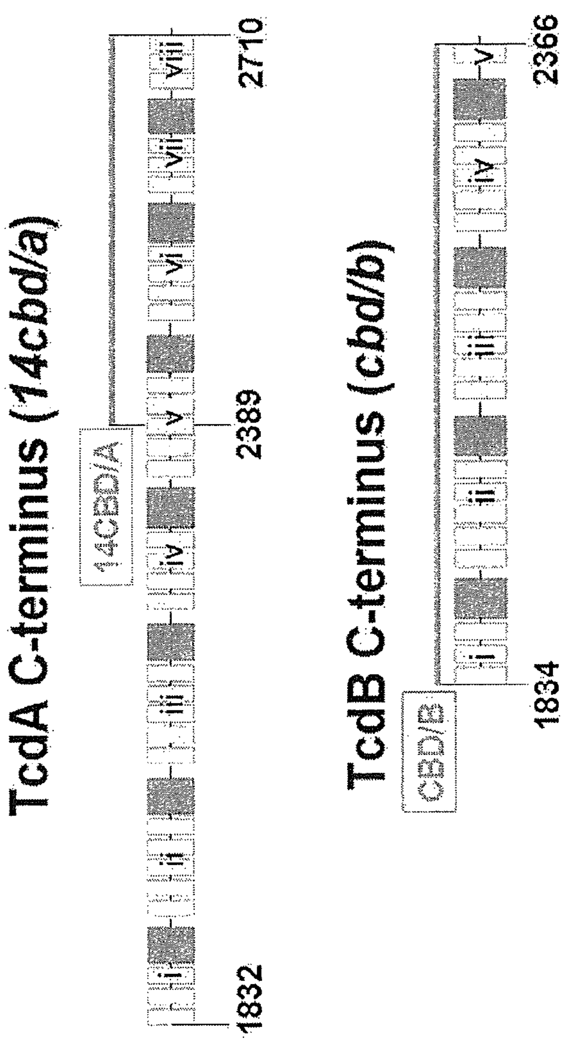
FIG. 1. Synthetic codon-optimized gene cassettes encoding regions of the cell-binding domains of *C. difficile* toxins A and B. 14CBD/A comprises residues 2389 to 2710 of toxin A and CBD/B comprises residues 1834-2366 of toxin B.

The cell binding domain of TcdA toxin (CBD/A) as described herein includes amino acids 1832-2710 of TcdA from *C. difficile* (see FIG. 1). In some embodiments, the *Salmonella Typhi* live vector expresses a truncated cell binding domain comprising amino acids 2389-2710. The amino acid sequence of the cell binding domains of TcdA of various *C. difficile* strains is provided by SEQ ID NOS:15-17.

The cell binding domain of TcdB toxin (CBD/B) as described herein includes amino acids 1834-2366 of TcdB from *C. difficile* (see FIG. 1). The amino acid sequence of the cell binding domains of various *C. difficile* strains is provided by SEQ ID NOS:18-19.

The invention further provides synthetic genes encoding the TcdA toxin (CBD/A) and TcdB toxin (CBD/B) that have been optimized for both genetic stability and efficient expression within the *S. Typhi* live vectors of the invention.

Figure 7:
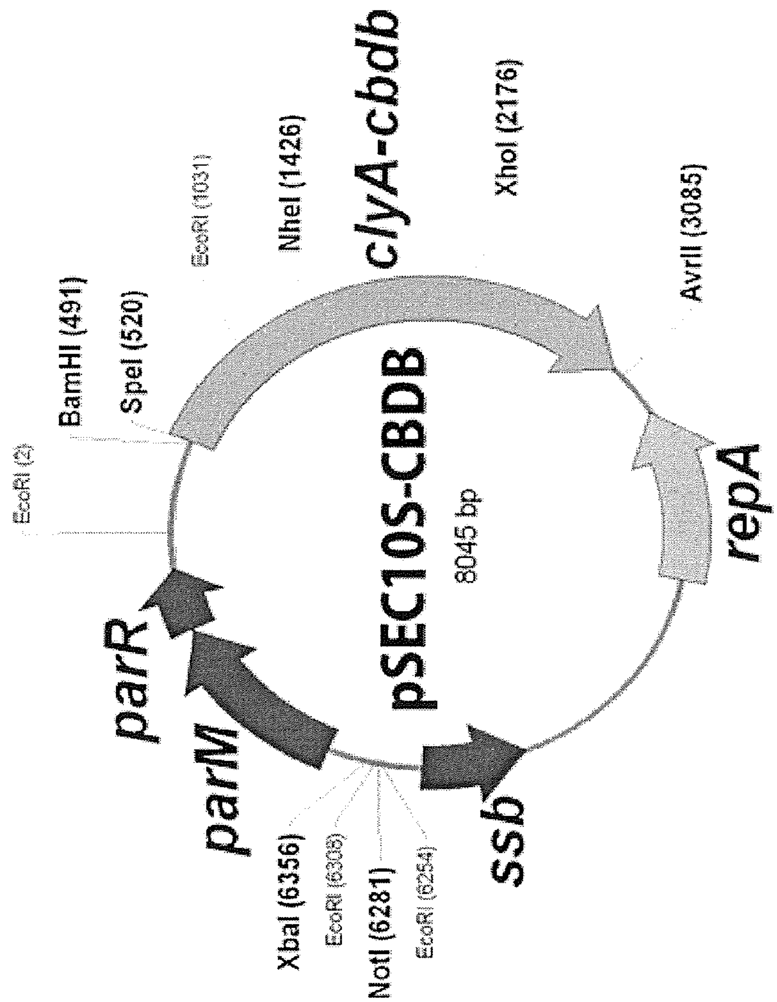
FIG. 7. A plasmid map of pSEC10S-CBDB, an expression vector for *S. Typhi* encoding a fusion of ClyA and the cell-binding domain fragment of TcdB (CBD/B).
Figure 8:
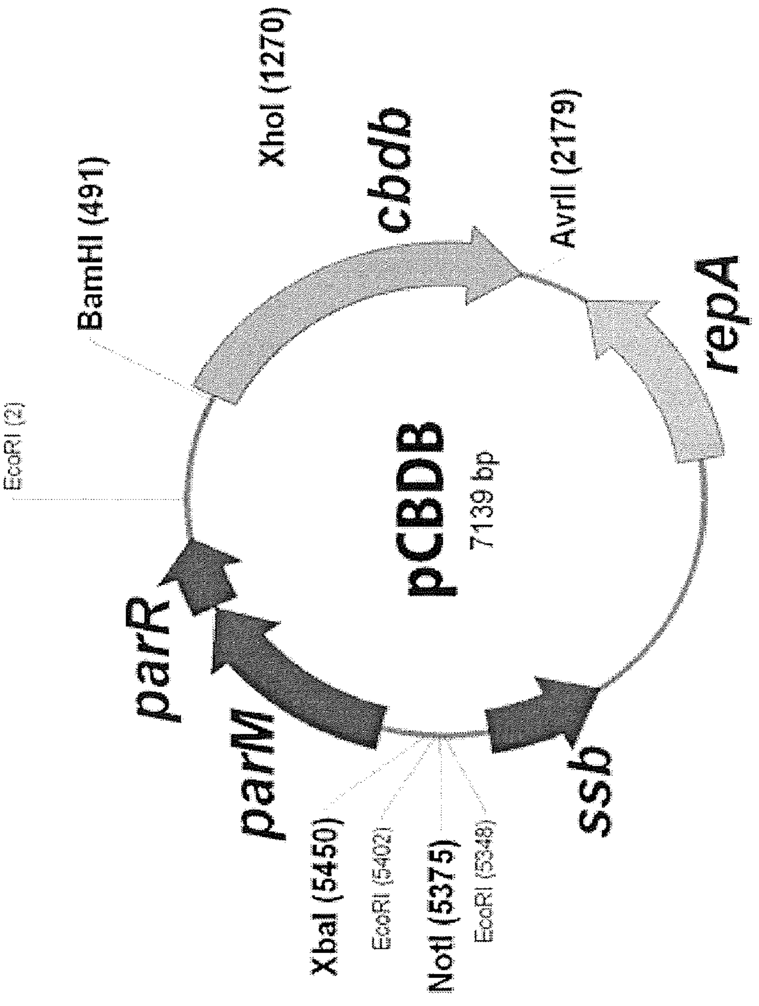
FIG. 8. A plasmid map of pCBDB, an expression vector for *S. Typhi* encoding a cell-binding domain fragment of TcdB (CBD/B).

Expression cassettes provided herein for TcdA toxin (CBD/A) and TcdB toxin (CBD/B) encode domains from the carboxyl-terminal receptor-binding region of TcdA and TcdB and include unique internal restriction sites to allow for easy manipulation. In one embodiment, restrictions sites NheI and AvrII span the cassette to facilitate easy cloning of the cassettes into expression vectors or to facilitate chromosomal insertion. These two cassettes comprise the C-terminal 322 residues of TcdA (amino acids 2389-2710 of TcdA) (14CBD/A) and comprise the C-terminal 533 residues of TcdB (CBD/B) (See FIG. 1). The nucleotide sequence of the codon optimized cassette of TcdA (14CBD/A) is SEQ ID NO:1 and the amino acid sequence is SEQ ID NO:2. The nucleotide sequence of the codon optimized cassette of TcdB (CBD/B) is SEQ ID NO:3 and the amino acid sequence is SEQ ID NO:4. Shown in FIG. 7 is the TcdB (CBD/B) cassette inserted into the NheI-AvrII sites of the pSEC 10 expression plasmid, creating the genetic fusion gene clyA-cbdb. The invention further provides a synthetic gene encoding the cell-binding subunit of binary toxin, CdtB, that has been optimized for both genetic stability and efficient expression within the *S. Tyhi* live vectors of the invention. The nucleotide sequence of the codon optimized gene cassette comprising the cell-binding subunit of binary toxin (CdtB) (encoding amino acids 2-876 of the wild-type sequence) is SEQ ID NO:5 and the amino acid sequence is SEQ ID NO:6.

As used herein the term "polypeptide" is used interchangeably with the term "protein" and is further meant to encompass peptides. Therefore, as used herein, a polypeptide is a polymer of two or more amino acids joined together by peptide linkages.

As used herein the term "antigenic fragment" of a particular protein is a fragment of that protein that is antigenic. For example, an antigenic fragment of TcdA (CBD/A), TcdB (CBD/B) or CdtB polypeptide can include a large fragment that is missing as little as a single amino acid. In a particular embodiment, an antigenic fragment of the polypeptide comprises at least 7 amino acid residues. In some embodiments, an antigenic fragment comprises at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues or at least 50 amino acid residues. In another embodiment, an antigenic fragment of TcdA (CBD/A), TcdB (CBD/B) or CdtB polypeptide comprises between 50 and 100 amino acid residues.

In yet another embodiment, an antigenic fragment of TcdA (CBD/A) comprises 100 amino acids or more, but fewer than 879 amino acids. In some embodiments, the antigenic fragment of TcdA (CBD/A) comprises between 150 and 850 amino acids, between 150 and 700 amino acids or between 200 and 500 amino acids. In some embodiments, the antigenic fragment comprises amino acids 5-325 of SEQ ID NO 2, amino acids 10-325 of SEQ ID NO 2, amino acids 20-325 of SEQ ID NO 2, amino acids 40-325 of SEQ ID NO 2, amino acids 75-325 of SEQ ID NO 2, amino acids 150-325 of SEQ ID NO 2, or amino acids 200-325 of SEQ ID NO 2. In some embodiments, the antigenic fragment comprises ammo acids 4-324 of SEQ ID NO 2, amino acids 4-300 of SEQ ID NO 2, amino acids 4-275 of SEQ ID NO 2, amino acids 4-250 of SEQ ID NO 2, amino acids 4-200 of SEQ ID NO 2, amino acids 4-150 of SEQ ID NO 2, or amino acids 4-100 of SEQ ID NO 2.

In yet another embodiment, an antigenic fragment of TcdB (CBD/B) comprises 100 amino acids or more, but fewer than 533 amino acids. In some embodiments, the antigenic fragment of TcdB (CBD/B) comprises between 150 and 500 amino acids, between 200 and 400 amino acids or between 250 and 350 amino acids. In some embodiments, the antigenic fragment comprises amino acids 5-536 of SEQ ID NO 4, amino acids 10-536 of SEQ ID NO 4, amino acids 20-536 of SEQ ID NO 4, amino acids 40-536 of SEQ ID NO 4, amino acids 75-536 of SEQ ID NO 4, amino acids 150-536 of SEQ ID NO 4, amino acids 250-536 of SEQ ID NO 4, amino acids 350-536 of SEQ ID NO 4, or amino acids 400-536 of SEQ ID NO 4. In some embodiments, the antigenic fragment comprises amino acids 4-535 of SEQ ID NO 4, amino acids 4-500 of SEQ ID NO 4, amino acids 4-400 of SEQ ID NO 4, amino acids 4-350 of SEQ ID NO 4, amino acids 4-275 of SEQ ID NO 4, amino acids 4-200 of SEQ ID NO 4, or amino acids 4-100 of SEQ ID NO 4.

In yet another embodiment, an antigenic fragment of CdtB comprises 100 amino acids or more, but fewer than 876 amino acids. In some embodiments, the antigenic fragment of CdtB comprises between 150 and 650 amino acids, between 200 and 550 amino acids or between 300 and 450 amino acids. In some embodiments, the antigenic fragment comprises amino acids 5-878 of SEQ ID NO 6, amino acids 10-878 of SEQ ID NO 6, amino acids 20-878 of SEQ ID NO 6, amino acids 40-878 of SEQ ID NO 6, amino acids 75-878 of SEQ ID NO 6, amino acids 150-878 of SEQ ID NO 6, amino acids 250-878 of SEQ ID NO 6, amino acids 350-878 of SEQ ID NO 6, amino acids 450-533 of SEQ ID NO 6, amino acids 550-878 of SEQ ID NO 6, amino acids 650-878 of SEQ ID NO 6, or amino acids 750-878 of SEQ ID NO 6. In some embodiments, the antigenic fragment comprises amino acids 4-877 of SEQ ID NO 6, amino acids 4-800 of SEQ ID NO 6, amino acids 4-700 of SEQ ID NO 6, amino acids 4-600 of SEQ ID NO 6, amino acids 4-500 of SEQ ID NO 6, amino acids 4-450 of SEQ ID NO 6, or amino acids 4-250 of SEQ ID NO 6.

There is no limitation on how the antigenic fragment can be made. For example, an antigenic fragment can be obtained from a recombinant source, from a protein isolated from natural sources, or through chemical synthesis. Similarly, an antigenic fragment can be obtained following the proteolytic digestion of such proteins or fragments.

*Salmonella Typhi* Live Vector Vaccines

*Salmonella* has been adapted for use as an attenuated live oral vaccine to deliver foreign antigens. Several attenuated *S. Typhi* strains have been developed over the years, including *S. Typhi* CVD 908 (Hone, D. M., A. M. Harris, S. Chatfield, G. Dougan, and M. M. Levine. 1991. Construction of genetically defined double aro mutants of *Salmonella typhi*. *Vaccine* 9:810-816; Tacket, C. O.,-M. Sztein, G. Losonsky, S. S. Wasserman, J. P. Nataro, R. Edelman, D. Pickard, G. Dougan, S. Chatfield, and M. M. Levine. 1997. Safety of live oral *Salmonella typhi* vaccine strains with deletions in htrA and aroC aroD and immune responses in humans. *Infect. Immun.* 65:452-456; Wang, J. Y., F. Noriega, J. E. Galen, E. M. Barry, and M. M. Levine. 2000. Constitutive expression of the Vi polysaccharide capsular antigen in attenuated *Salmonella enterica* serovar *Typhi* oral vaccine strain CVD 909. *Infect. Immun.* 68:4647-4652; Wang, J. Y., M. F. Pasetti, F. Noriega, R. J. Anderson, S. S. Wasserman, J. E. Galen, M. Sztein, and M. M. Levine. 2001. Construction, genotypic and phenotypic characterization, and immunogenicity of attenuated DguaBA *Salmonella enterica* serovar *Typhi* strain CVD 915. *Infect. Immun.* 69:4734-4741). *S. Typhi* CVD 908 is attenuated through stable chromosomal integration of two non-reverting deletion mutations within the aroC and aroD genes. These two genes encode enzymes critical in the biosynthesis of several aromatic amino acids, as well as biosynthesis of the purine nucleotides ATP and GTP. The pleiotropic effect of the ΔaroCΔaroD double deletion mutations is responsible for the level of attenuation observed when CVD 908 was given to volunteers in Phase 1 studies. Immunization with CVD 908 was quite well tolerated and highly immunogenic (Tacket, C. O., D. M. Hone, R. Curtiss III, S. M. Kelly, G. Losonsky, L. Guers, A. M. Harris, R. Edelman, and M. M. Levine. 1992. Comparison of the safety and immunogenicity of DaroCDaroD and DcyaDcrp *Salmonella typhi* strains in adult volunteers. *Infect. Immun.* 60:536-541). However, a clinically silent primary bacteremia was detected in 100% of volunteers who ingested $5\times10^8$ colony forming units (CFU), wherein vaccine organisms were recovered from blood cultures collected between days 4 and 8 after vaccination (Levine, M. M., J. E. Galen, E. M. Barry, F. Noriega, S. Chatfield, M. Sztein, G. Dougan, and C. O. Tacket. 1996. Attenuated *Salmonella* as live oral vaccines against typhoid fever and as live vectors. *J. Biotechnol.* 44:193-196.) This silent vaccinemia presumably resulted from migration of the vaccine strain to the organs of the reticuloendothelial system, but was not associated with adverse clinical symptoms and spontaneously resolved without antibiotic intervention.

CVD 908 has been further attenuated to avoid this silent vaccinemia by introducing an additional defined deletion mutation into the htrA gene encoding a stress-induced serine protease responsible for degradation of mis-folded periplasmic proteins (Pallen, M. J. and B. W. Wren. 1997. The HtrA family of serine proteases. *Mol. Microbial.* 26:209-221). The htrA locus was chosen because htrA mutants in *S. Typhimurium* were less virulent in mice, and were shown in vitro to be less able to withstand the oxidative burst following phagocytosis into macrophages (Chatfield, S., K. Strahan, D. Pickard, I. G. Charles, C. E. Hormaeche, and G. Dougan. 1992. Evaluation of *Salmonella typhimurium* strains harbouring defined mutations in htrA and aroA in the murine salmonellosis model. *Microb. Pathog.* 12:145-151; Baumler, A. J., J. G. Kusters, I. Stojiljkovic, and F. Heffron. 1994. *Salmonella typhimurium* loci involved in survival within macrophages. *Infect. Immun.* 62:1623-1630). The resulting CVD 908-htrA vaccine strain was found to be well tolerated at doses up to $5\times10^9$ CFU with no positive blood cultures detected. In addition, CVD 908-htrA elicited a broad immune response to *S. Typhi* antigens that included intestinal secretory IgA antibodies, serum IgG antibodies, and cellular immune responses (Salerno-Goncalves, R., T. L. Wyant, M. F. Pasetti, M. Fernandez-Vina, C. O. Tacket, M. M. Levine, and M. B. Sztein. 2003. Concomitant induction of CD4+ and CD8+ T cell responses in volunteers immunized with *Salmonella enterica* serovar typhi strain CVD 908-htrA. *J. Immunol.* 170:2734-2741; Tacket, C. O., M. Sztein, G. Losonsky, S. S. Wasserman, J. P. Nataro, R. Edelman, D. Pickard, G. Dougan, S. Chatfield, and M. M. Levine. 1997. Safety of live oral *Salmonella typhi* vaccine strains with deletions in htrA and aroC aroD and immune responses in humans. Infect. Immun. 65:452-456; Tacket, C. O., M. Sztein, S. S. Wasserman, G. Losonsky, K. Kotloff, T. L. Wyant, J. P. Nataro, R. Edelman, J. G. Perry, P. Bedford, D. Brown, S. Chatfield, G. Dougan, and M. M. Levine. 2000. Phase 2 clinical trial of attenuated *Salmonella enterica* serovar *Typhi* oral live vector vaccine CVD 908-htrA in U.S. volunteers. Infect. Immun. 68:1196-1201). *S. Typhi* is characterized by enteric routes of infection, a quality which permits oral vaccine delivery. *S. Typhi* also infects monocytes and macrophages and can therefore target antigens to professional antigen presenting cells (APCs).

The *Salmonella Typhi* strain that can be used in the present invention as a vaccine is not limited to any particular strain that has been genetically attenuated from the original clinical isolate Ty2. Any attenuated *Salmonella Typhi* strain derived from Ty2 can be used as a live vector in accordance with the invention. Non-limiting, exemplary attenuated *Salmonella Typhi* strains include *S. Typhi* Ty21a, CVD 908, *S. Typhi* CVD 909, CVD 908-htrA, and CVD 915. In some embodiments, the *S. Typhi* strain can carry one or more additional chromosomal mutations in an essential gene that is expressed on a plasmid which also encodes a *C. difficile* toxin, in accordance with the invention, enabling selection and stabilization of the plasmid and preventing loss in *S. Typhi*. In some embodiments, the *S. Typhi* strain carries a mutation in the ssb gene which is encoded on a selection expression plasmid. In some embodiments, the *S. Typhi* strain carrying a ssb mutation is selected from *S. Typhi* CVD 908ssb and CVD 908-htrAssb.

One or more of the TcdA toxin (CBD/A), TcdB (CBD/B) toxin and CdtB toxin proteins can be expressed on one or more plasmids in the live *S. Typhi* vector of the invention. In some embodiments, only one toxin is expressed on a plasmid, while the one or more genes encoding the remaining toxins of *C. difficile* are chromosomally inserted and expressed. In some embodiments, at least two toxin genes are expressed on a plasmid.

Plasmid stability is a key factor in the development of high quality attenuated *S. Typhi* vaccines with the ability to consistently express foreign antigens. Plasmidless bacterial cells tend to accumulate more rapidly than plasmid-bearing cells. One reason for this increased rate of accumulation is that the transcription and translation of plasmid genes imposes a metabolic burden which slows cell growth and gives plasmidless cells a competitive advantage. Furthermore, foreign plasmid gene products are sometimes toxic to the host cell. Thus, it is advantageous for the plasmid to be under some form of selective pressure, in order to ensure that the encoded antigens are properly and efficiently expressed, so that a robust and effective immune response can be achieved.

In some embodiments, the plasmid is selected within *S. Typhi* using a non-antibiotic selection system. For example, the plasmid can encode an essential gene that complements an otherwise lethal deletion/mutation of this locus from the live vector chromosome. Exemplary non-antibiotic expression plasmids that can be used in the invention are described herein and further plasmid systems which can be used in the invention are described, for example, in U.S. Patent Appl. Pub. No. 20070281348, U.S. Pat. Nos. 7,141,408, 7,138,112, 7,125,720, 6,977,176, 6,969,513, 6,703,233, and 6,413,768, which are herein incorporated by reference.

The present inventor has recently developed a non-antibiotic genetic stabilization and selection system for expression plasmids engineered to encode single-stranded binding protein (SSB), an essential protein involved in DNA replication, recombination, and repair which is deleted from the *S. Typhi* live vector chromosome (Lohman T M, Ferrari M E. *Escherichia coli* single-stranded DNA-binding protein: multiple DNA-binding modes and cooperativities. *Annu Rev Biochem.* 1994; 63:527-570; Chase J W, Williams K R. Single-stranded DNA binding proteins required for DNA replication. *Annu Rev Biochem.* 1986; 55:103-136; Galen J E, Wang J Y, Chinchilla M, Vindurampulle C, Vogel J E, Levy H, Blackwelder W C, Pasetti M F, Levine M M. A new generation of stable, nonantibiotic, low-copy-number plasmids improves immune responses to foreign antigens in *Salmonella enterica* serovar *Typhi* live vectors. *Infect Immun.* 2010 January; 78(1):337-47). In some embodiments, the plasmid expression vector for *S. Typhi* encodes a single-stranded binding protein (SSB). In some embodiments, the expression vector is pSEC10S as described herein.

In some embodiments of the invention, expression plasmids are employed in which both the random segregation and catalytic limitations inherent in non-antibiotic plasmid selection systems have been removed. The segregation of these plasmids within *S. Typhi* live vectors is improved using an active partitioning system (parA) for *S. Typhi* CVD 908-htrA (Galen, J. E., J. Nair, J. Y. Wang, S. S. Wasserman, M. K. Tanner, M. Sztein, and M. M. Levine. 1999. Optimization of plasmid maintenance in the attenuated live vector vaccine strain *Salmonella typhi* CVD 908-htrA. *Infect. Immun.* 67:6424-6433). In some embodiments, dependence on catalytic enzymes is avoided by using a plasmid selection/post-segregational killing system based on the ssb gene.

Chromosomal Expression of *C. difficile* Toxins

A solution to the instability of multicopy plasmids and the foreign antigens they encode is to integrate foreign gene cassettes into the chromosome of the live vector. However, the drop in copy number becomes both an advantage and a disadvantage; while the reduced copy number will certainly reduce the metabolic burden associated with both the multicopy plasmid itself and the encoded foreign protein(s), this reduction in foreign antigen synthesis ultimately leads to reduced delivery of these antigens to the host immune system and possibly reduced immunogenicity. This explanation could account for why in clinical trials serum immune responses to chromosomally encoded antigens have to date been modest. (Gonzalez C, Hone D, Noriega F R et al. *Salmonella typhi* vaccine strain CVD 908 expressing the circumsporozoite protein of *Plasmodium falciparum*: strain construction and safety and immunogenicity in humans. *J Infect Dis.* 1994; 169:927-931; Khan. S, Chatfield S, Stratford R et al. Ability of SPI2 mutant of *S. typhi* to effectively induce antibody responses to the mucosal antigen enterotoxigenic *E. coli* heat labile toxin B subunit after oral delivery to humans. *Vaccine.* 2007; 25:4175-4182). To date the only chromosomal locus used in clinical trials for expression of foreign antigens is aroC.

The present invention provides for chromosomal insertion of one or more *C. difficile* toxin cassettes into the guaBA locus and/or htrA locus of *S. Typhi*. It will be appreciated that inserting the gene cassettes into either the guaBA locus or the htrA locus of *S. Typhi* is routine, and can be accomplished, for example, using standard techniques in molecular biology, including the lambda Red recombination system (Datsenko K A and Wanner B L. One-step inactivation of chromosomal genes in *Escherichia coli* K-12 using PCR products. PNAS. 2000. 97(12): 6640-5.).

Immunogenic cassettes can be integrated into either the ΔguaBA or ΔhtrA locus of CVD 910ssb, for example, to compare the immunogenicity of chromosomal integrations versus antigen-specific immunogenicity elicited by plasmid-based expression. In some embodiments, only the open reading frames of ΔguaBA and ΔhtrA are deleted, leaving the original promoters for these sites intact. In some embodiments, insertion cassettes include the $P_{ompC}$ promoter from the low copy expression plasmids, such that integration into ΔguaBA or ΔhtrA results in nested promoters controlling inducible expression of a given cassette at two levels.

Figure 9:
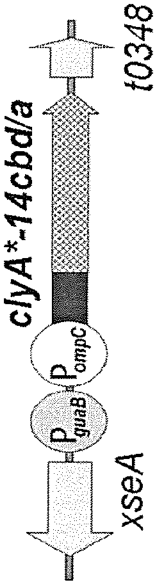
FIG. 9. Integration of a synthetic codon-optimized gene cassette, encoding a fusion of non-hemolytic ClyA* fused to the cell-binding domain of *C. difficile* toxin A (14CBD/A), integrated into the chromosomal ΔguaBA locus of the CVD 910ssb attenuated live vector. The blue and yellow ovals denote nested $P_{guaB}$ and $P_{ompC}$ promoters controlling expression of clyA*-14cbd/A by growth rate and osmolarity respectively. The intact wildtype chromosomal loci xseA and 10348 from *S. Typhi* strain Ty2, which flank the ΔguaBA::clyA*-14cbd/a insertion, are represented by arrows.

For example, integration of a $P_{ompC}$-clyA*-14cbd/a cassette (encoding the ClyA*-14CBD/A fusion) into ΔguaBA of CVD 910ssb would result in inducible transcription of clyA*-14cbd/a with both growth rate and osmolarity, as shown in FIG. 9. A synthetic gene encoding the TcdA toxin (CBD/A) or an antigenic fragment thereof can be inserted into guaBA locus, the htrA locus, or both loci. A synthetic gene encoding the TcdB toxin (CBD/B) or an antigenic fragment thereof can be inserted into guaBA locus, the htrA locus, or both loci. A synthetic gene ecoding CdtB or an antigenic fragment thereof can be inserted into guaBA locus, the htrA locus, or both loci. In one embodiment, the invention provides a *Salmonella Typhi* live vector vaccine wherein CdtB is inserted into the htrA locus, TcdA toxin (CBD/A) is inserted into the guaBA locus and the TcdB toxin (CBD/B) is expressed on a plasmid.

Export of TcdA (CBD/A), TcdB (CBD/B) and CdtB out of *S. Typhi* Live Vectors using ClyA Fusions The invention also provides for the use of an extracellular antigen export system derived from a cryptic hemolysin encoded by clyA within the chromosome of CVD 908-htrA (Galen, J. E., L. Zhao, M. Chinchilla, J. Y. Wang, M. F. Pasetti, J. Green, and M. M. Levine. 2004. Adaptation of the endogenous *Salmonella enterica* serovar Typhi clyA-encoded hemolysin for antigen export enhances the immunogenicity of anthrax protective antigen domain 4 expressed by the attenuated live-vector vaccine strain CVD 908-htrA. *Infect. Immun.* 72:7096-7106). In some embodiments, one or more of TcdA (CBD/A), CdtB and TcdB (CBD/B) are fused to either wild-type or mutant cytolysin A (ClyA) protein from *S. Typhi* to facilitate export from the cell and contact with antibodies to thereby enhance immunogenicity. The ClyA export system is described in U.S. Pat. No. 7,459,161, which is incorporated by reference herein.

The ClyA protein is exported from *S. Typhi* and is capable of exporting passenger proteins that have been genetically fused to the 3'-terminus of the clyA open reading frame. The nucleotide and amino acid sequence for the isolated clyA gene and ClyA protein useful in accordance with the invention are provided as SEQ ID NO:13 and SEQ ID NO:14, respectively. Cytolysin A (ClyA) from *S. Typhi* was first described by Wallace et al., who also reported the crystal structure for the homologous HlyE hemolysin from *E. coli*. (Wallace, A. J., T. J. Stillman, A. Atkins, S. J. Jamieson, P. A. Bullough, J. Green, and P. J. Artymiuk. 2000. *E. coli* hemolysin E (HlyE, ClyA, SheA): X-ray crystal structure of the toxin and observation of membrane pores by electron microscopy. *Cell* 100:265-276.) HlyE is a kinked rod-shaped 35 kDa molecule with a hydrophobic 27 residue transmembrane region comprising one terminus of the folded molecule. HlyE is exported into the surrounding medium, but is not exported by any of the known secretion pathways. This hemolysin has been described previously and variously referred to as ClyA, HlyE, or SheA. To avoid confusion, the *E. coli* hemolysin is referred to herein as HlyE and is encoded by hlyE. Also for clarity, the *S. Typhi* hemolysin is referred to herein as ClyA, which is encoded by clyA.

ClyA protein typically causes hemolysis in target cells. The present invention encompasses use of both hemolytically active and hemolytically inactive forms of ClyA, with hemolytically inactive mutant forms being more preferred where preservation of antigen export and immunogenicity of the resulting protein fusions can be maintained. In some embodiments, the ClyA is mutated to reduce the hemolytic activity of ClyA while still retaining the export function of ClyA. In one embodiment, the ClyA mutant is ClyA I198N. In another embodiment, the ClyA mutant is ClyA C285W.

Pharmaceutical Formulations

It is contemplated that the *S. Typhi* live vector vaccines of the present invention will be administered in pharmaceutical formulations for use in vaccination of individuals, preferably humans. Such pharmaceutical formulations may include pharmaceutically effective carriers, and optionally, may include other therapeutic ingredients, such as various adjuvants known in the art.

The carrier or carriers must be pharmaceutically acceptable in the sense that they are compatible with the therapeutic ingredients and are not unduly deleterious to the recipient thereof. The therapeutic ingredient or ingredients are provided in an amount and frequency necessary to achieve the desired immunological effect.

The mode of administration and dosage forms will affect the therapeutic amounts of the compounds which are desirable and efficacious for the vaccination application. The bacterial live vector materials are delivered in an amount capable of eliciting an immune reaction in which it is effective to increase the patient's immune response to the expressed toxin(s).

Delivery modes may include, without limitation, parenteral administration methods, such as subcutaneous (SC) injection, transdermal, intramuscular (IM), intradermal (ID), as well as non-parenteral, e.g., oral, nasal, intravaginal, pulmonary, opthalmic and/or rectal administration. Oral administration of the live vector vaccine is preferred, while parenteral routes of administration are preferred for peptide based vaccine compositions.

The dose rate and suitable dosage forms for the bacterial live vector vaccine compositions of the present invention may be readily determined by those of ordinary skill in the art without undue experimentation, by use of conventional antibody titer determination techniques and conventional bioefficacy/biocompatibility protocols. Among other things, the dose rate and suitable dosage forms depend on the particular antigen employed, the desired therapeutic effect, and the desired time span of bioactivity.

The bacterial live vector vaccines of the present invention may be usefully administered to the host animal with any other suitable pharmacologically or physiologically active agents, e.g., antigenic and/or other biologically active substances.

Formulations of the present invention can be presented, for example, as discrete units such as capsules, cachets, tablets or lozenges, each containing a predetermined amount of the live *S. Typhi* vector or as a suspension.

Therapeutic Methods

The present invention also includes methods of inducing an immune response in a subject. The immune response may be directed to one or more *Clostridium difficile* antigens expressed by the *Salmonella Typhi* live vector comprising toxin TcdA (CBD/A) or an antigenic fragment thereof, toxin TcdB (CBD/B) or an antigenic fragment thereof, and the colonization factor CdtB or an antigenic fragment thereof.

In another aspect, the present invention is directed to methods of inducing an immune response against *Clostridium difficile* in a subject in need thereof, comprising administering to the subject an immunologically-effective amount of a live *Salmonella Typhi* vector as described herein. In some embodiments, the live vector is administered mucosally.

Vaccine strategies are well known in the art and therefore the vaccination strategy encompassed by the invention does not limit the invention in any manner. In certain aspects of the invention, the *S. Typhi* live vector vaccine expressing the *C. difficile* toxin antigens is administered alone in a single application or administered in sequential applications, spaced out over time.

In other aspects of the invention, the *S. Typhi* live vector vaccine is administered as a component of a heterologous prime/boost regimen. "Heterologous prime/boost" strategies are 2-phase immunization regimes involving sequential administration (in a priming phase and a boosting phase) of the same antigen in two different vaccine formulations by the same or different route. In particular aspects of the invention drawn to heterologous prime/boost regimens, a mucosal prime/parenteral boost immunization strategy is used. For example, one or more *S. Typhi* live vector vaccines as taught herein is administered orally and subsequently boosted parentally with a peptide vaccine comprising one or more of TcdA toxin (CBD/A) or an antigenic fragment thereof, toxin TcdB (CBD/B) or an antigenic fragment thereof, and the colonization factor CdtB or an antigenic fragment thereof, or combinations thereof.

In another aspect, the present invention is directed to methods of inducing an immune response against *Clostridium difficile* in a subject in need thereof, comprising administering to the subject an immunologically-effective amount of a live *Salmonella Typhi* vector of the invention as a prime, and subsequently administering a boost composition comprising a polypeptide selected from the group consisting of TcdA toxin (CBD/A) or an antigenic fragment thereof, TcdB toxin (CBD/B) or an antigenic fragment thereof, and CdtB or an antigenic fragment thereof, and combinations thereof.

In another aspect, the invention is directed to preventing recurrence of a *Clostridium difficile* infection in a subject in need thereof, comprising administering to the subject an immunologically-effective amount of a live *S. Typhi* vector as described herein. In another aspect, the present invention is directed to preventing recurrence of a *Clostridium difficile* infection in a subject in need thereof, comprising administering to the subject an immunologically-effective amount of a live *S. Typhi* vector as described herein as a prime, and subsequently administering a boost composition that comprises a polypeptide selected from the group consisting of TcdA toxin (CBD/A) or an antigenic fragment thereof, TcdB toxin (CBD/B) or an antigenic fragment thereof, and CdtB or an antigenic fragment thereof, and combinations thereof.

In one embodiment, the method of inducing an immune response comprises mucosally administering to the subject in need thereof an immunologically-effective amount of a live *S. Typhi* vector comprising the cell binding domain of toxin TcdA (CBD/A) or an antigenic fragment thereof and the cell binding domain of toxin TcdB (CBD/B) or an antigenic fragment thereof of *Clostridium difficile*, and optionally, further comprising the colonization factor CdtB of *Clostridium difficile* or an antigenic fragment thereof.

In a further embodiment, the method of inducing an immune response comprises administering a *S. Typhi* live vector vaccine of the present invention to a subject in an amount sufficient to induce an immune response in the subject (an immunologically-effective amount).

As used herein, an "immune response" is the physiological response of the subject's immune system to an immunizing composition. An immune response may include an innate immune response, an adaptive immune response, or both. In one embodiment of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

In a further embodiment, the method of inducing an immune response comprises administering a pharmaceutical formulation comprising one or more *Salmonella Typhi* live vectors of the present invention to a subject in an amount sufficient to induce an immune response in the subject (an immunologically-effective amount). In some embodiments, the immune response is sufficient to confer protective immunity upon the subject against a later *Clostridium difficile* infection.

In another aspect, the invention is directed to methods of inducing an immune response, comprising administering to a subject in need thereof a first vaccine comprising an immunologically-effective amount of a *S. Typhi* live vector expressing at least TcdA toxin (CBD/A), and TcdB toxin (CBD/B ) of *Clostridium difficile*, and optionally CtdB or an antigenic fragment thereof, and subsequently a second vaccine comprising an immunologically-effective amount of a peptide vaccine comprising one or more of TcdA toxin (CBD/A) or an antigenic fragment thereof, and TcdB toxin (CBD/B), and CdtB or an antigenic fragment thereof. In one embodiment, a subject is orally administered one or more *S. Typhi* live vectors of the invention, followed by a booster immunization administered parenterally, comprising an immunologically-effective amount of a peptide based vaccine comprising one or more of TcdA toxin (CBD/A) or an antigenic fragment thereof, and TcdB toxin (CBD/B), and CdtB or an antigenic fragment thereof. In some embodiments, the time interval between the first and second vaccinations is 1-2 weeks, 3-4 weeks, 5-6 weeks, 7-9 weeks, 10-12 weeks, 4 months, 5 months, 6 months, 7 months, 8 months, 9 months, 10 months, 11 months, 1 year, 1.5 years, 2 years, 5 years, 7 years, 10 years and 15 years.

In some embodiments, one or more *S. Typhi* live vector vaccines of the invention are mucosally administered in a first priming administration, followed, optionally, by a second (or third, fourth, fifth, etc. . . . ) priming administration of the live vector vaccine from about 2 to about 10 weeks later. In some embodiments, a boosting composition is administered from about 3 to about 12 weeks after the priming administration. In some embodiments, the boosting composition is administered from about 3 to about 6 weeks after the priming administration.

In some embodiments, the vaccine of the invention is administered with a pharmaceutically acceptable carrier, such that it provides host immunity against an infection.

The term "carrier" denotes an organic or inorganic ingredient, natural or synthetic, with which the active ingredient is combined to facilitate the application. The characteristics of the carrier depend on the nature of the vaccine and the route of administration. Physiologically and pharmaceutically-acceptable carriers include diluents, fillers, salts, buffers, stabilizers, solubilizers, and other materials which are well known in the art. The term "pharmaceutically acceptable" is used to refer to a non-toxic material that is compatible with a biological system such as a cell, cell culture, tissue, or organism.

In practicing immunization protocols for treatment and/or prevention, an immunologically-effective amount of a live *Salmonella Typhi* vector is administered to a subject. As used herein, the term "immunologically-effective amount" means the total amount of a live *S. Typhi* vector that is sufficient to show an enhanced immune response in the subject. When "immunologically-effective amount" is applied to an individual therapeutic agent administered alone, the term refers to that therapeutic agent alone. When applied to a combination, the term refers to combined amounts of the ingredients that result in the therapeutic effect, whether administered in combination, serially or simultaneously.

The particular dosage depends upon the age, weight, sex and medical condition of the subject to be treated, as well as on the method of administration. Suitable doses can be readily determined by those of skill in the art.

For peptide based vaccines used for boosting, peptide vaccines can be administered by either single or multiple dosages of an effective amount. In some embodiments, an effective amount of the compositions of the invention can vary from 0.01-200 μg/kg per dose. In other embodiments, an effective amount of the composition of the invention can vary from 0.1-100 μg/kg per dose. Greater doses may be administered on the basis of body weight. The exact dosage can be determined by routine dose/response protocols known to one of ordinary skill in the art. DNA-based vaccines encoding the peptides can also be used as a boost. The boost can also comprise a combination of peptide and DNA-based vaccines.

In some embodiments, the amount of the peptide based vaccine that is effective for boosting is from about 1 μg or less to about 100 μg or more. In some embodiments, it is from about 2, 3, 4, 5, 6, 7, 8, 9, 10, 15, 20, 25, 30, 35, 40, 45 or 50 μg to about 55, 60, 65, 70, 75, 80, 85, 90, or 95 mg per kg body weight.

The term "subject" as used herein, refers to animals, such as mammals. For example, mammals contemplated include humans, primates, dogs, cats, sheep, cattle, goats, pigs, horses, mice, rats, rabbits, guinea pigs, and the like. The terms "subject," "patient," and "host" are used interchangeably.

In some embodiments, the subject to be administered the *S. Typhi* live vector of the invention presents with an existing *C. difficile* infection, in some cases by showing that either toxin A or B is positively identified in the stool. In such patients who are actively colonized with *C. difficile*, it is expected that they will be already immunologically primed against toxins A and B such that oral immunization with the *S. Typhi* live vector vaccine will elicit an anamnestic neutralizing anti-toxin response against both toxins, as well as binary toxin mucosal immunity, reducing the probability of later recurrent infection. In some embodiments, the subject is administered the vaccine while they are concurrently administered antibiotics to treat the infection, such as vancomycin.

In some embodiments, the subject to be administered the vaccine has been recently hospitalized and/or received antibiotic therapy. The leading risk factors associated with CDAD include recent antibiotic therapy and hospitalization, with attack rates peaking in elderly patients. In some embodiments, the patient is administered the live vector vaccine following a course of antibiotics or shortly following a hospital stay. For example, the subject can be administered the live vector vaccine one week following the course of antibiotics, to allow for clearance of antibiotics and improved colonization of the gastrointestinal tract by the attenuated live *S. Typhi* bacterial vaccine. Improved colonization with *S. Typhi* live vectors will result in delivery of high levels of *C. difficile* antigens to the mucosal immune system to enhance protection against recurrence of infection. In such patients, the methods are intended to confer protective immunity in the subject against later recurrent *Clostridium difficile* infection(s).

In some embodiments, a human subject between the ages of 50 and 64 years of age is administered the live vector vaccine mucosally, and is boosted at a later time, either with the live vector vaccine or a peptide toxoid preparation. For example, the subsequent boosting can take place when the levels of antibody caused by the original administration begin to decline or fade. This can occur after about 5-10 years in some cases. In some embodiments, a boost can be administered about 5-10 years after the initial priming. In some embodiments, it can be advantageous to administer the boost before the subject turns 65 years old, when patients, in general, start to become refractory to vaccine administrations.

The live *S. Typhi* vectors of the present invention may confer resistance to *Clostridium difficile* by either passive immunization or active immunization. In one embodiment of passive immunization, the vaccine is provided to a subject (e.g. a human or mammal) volunteer, and the elicited antisera is recovered and directly provided to a recipient suspected of having an infection caused by *Clostridium difficile*.

In some embodiments, the present invention provides a means for preventing or attenuating infection by *Clostridium difficile*. As used herein, a vaccine is said to prevent or attenuate a disease if its administration to an individual results either in the total or partial attenuation (i.e. suppression) of a symptom or condition of the disease, or in the total or partial immunity of the individual to the disease.

The invention also provides a method for inducing an immune response which comprises administering to an individual suspected of being at risk for infection caused by *Clostridium difficile* an immunologically-effective amount of an antisera elicited from the exposure of a second individual to a live *S. Typhi* vector of the invention, such that it provides host immunity to the infection.

The live *Salmonella Typhi* vectors of the invention may be administered to warm-blooded mammals of any age. The live *Salmonella Typhi* vectors can be administered as a single or multiple priming doses, followed by one or more boosters. For example, a subject can receive a single dose, then be administered a booster dose up to 1 month, 2 months, 3 months, 4 months, 5 months, 6 months, 9 months, 1 year, 2 years, 3 years, 4 years, 5 years, 6 years, 7 years, 8 years, 9 years, or 10 or more years later. In some embodiments, two booster injections of about 10 μg, 30 μg, 60 μg, 90 μg, 60 μg, 90 μg, 120 μg, 150 μg, 180 μg, 210 μg, 240 μg, 270 μg or about 300 μg are administered at about 2 and again about 13 months after the initial injection. Alternatively, three booster injections are given at 2, 4 and 16 months after the initial injection.

The present invention may be better understood by reference to the following non-limiting Examples, which are provided as exemplary of the invention. The following examples are presented in order to more fully illustrate some embodiments of the invention. They should in no way be construed, however, as limiting the broad scope of the invention.

EXAMPLES

Example 1

Expression of TcdA and TcdB in Attenuated *S. Typhi* Live Vectors

Two synthetic codon-optimized genes have been engineered for efficient expression in attenuated *S. Typhi* live vectors. Both cassettes encode domains from the carboxyl-terminal receptor-binding region of TcdA and TcdB and include unique internal restriction sites to allow truncation should expression of the full-length cassettes prove toxic. These two cassettes encode the C-terminal 322 residues of TcdA (14CBD/A) and 533 residues of TcdB (CBD/B) (See FIG. 1). The nucleotide sequence of the codon optimized cassette of CBD/A is SEQ ID NO:1 and the amino acid sequence is SEQ ID NO:2. The nucleotide sequence of the codon optimized cassette of CBD/B is SEQ ID NO:3 and the amino acid sequence is SEQ ID NO:4.

Based on recent work from Greco et al, 14CBD/A would be expected to contain at least 3 carbohydrate receptor-binding sites (Greco A, Ho J G, Lin Palcic M M, Rupnik M, Ng K K. Carbohydrate recognition by *Clostridium difficile* toxin A. *Nat Struct Mol. Biol.* 2006; 13:460-461). The entire C-terminal region of TcdB was elected to be expressed because no structural data has specifically defined any receptor-binding site(s) for TcdB.

Both synthetic genes were engineered with codon usage optimized for efficient expression in *S. Typhi*. Since both cassettes encode highly repetitive regions of the *C. difficile* toxins, the DNA sequences were also engineered to enhance genetic stability by removing inverted repeats and palindromes, and minimizing direct repeats to less than 12 bases in length with theoretical melting temperatures ≤39° C. Previous work by Ward et al. has show that expression of a cassette similar to 14CBD/A fused to the carboxyl-terminus of tetanus toxin fragment C and delivered by an auxotrophic strain of *S. Typhimurium* (BRD509), elicited serum neutralizing antibody responses against toxin A in mice immunized intranasally with two doses of $10^7$ cfu of live vector followed by boosting with purified 14CDTA. (Ward S J, Douce G, Figueiredo D, Dougan G, Wren B W. Immunogenicity of a *Salmonella Typhimurium* aroA aroD vaccine expressing a nontoxic domain of *Clostridium difficile* toxin A. *Infect Immun.* 1999; 67:2145-2152).

Figure 2:
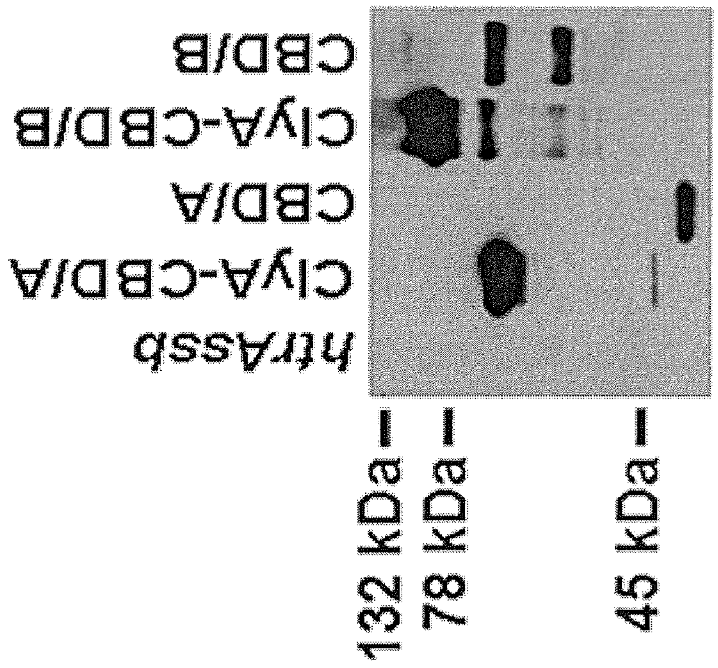
FIG. 2. Western immunoblot of whole cell lystes from attenuated *S. Typhi* CVD 908-htrAssb expressing fused and unfused CBD/B antigens from the cell-binding domain of *C. difficile* toxin B.

Both synthetic genes were designed as Nhe I-Avr II cassettes for insertion into expression plasmids either as fusions to clyA (to allow antigen export out of live vectors) or as unfused genes (for cytoplasmic expression). Of note, fusion of the C-terminal domain of a much larger region of C-terminal TcdA (720 residues, ~6 carbohydrate binding sites) to the *E. coli* hemolysin A secretion system was previously hypothesized to improve immunogenicity by allowing export of this domain out of an attenuated *Vibrio cholerae* live vector. (Ryan E T, Butterton J R, Smith R N, Carroll P A, Crean T I, Calderwood S B. Protective immunity against *Clostridium difficile* toxin A induced by oral immunization with a live, attenuated *Vibrio cholerae* vector strain. *Infect Immun.* 1997; 65:2941-2949). The cassettes did not insert into higher copy number (~15 copies per chromosomal equivalent) SSB-stabilized expression plasmids, but both cassettes were readily inserted, in both fused and unfused configurations, into an SSB-encoding low copy (~5 copies) replicon. Desired constructs were confirmed by DNA sequence analysis, and are designated here as pSEC10S-14CBD/A (expressing a truncated Cell Binding Domain of TcdA fused to ClyA), p14CBD/A (expressing unfused TcdA antigen), pSEC10S-CBD/B (expressing the full-length Cell Binding Domain of TcdB fused to ClyA), and pCBD/B (expressing unfused TcdB antigen). These four constructs were electroporated into CVD 908-htrAssb and examined using western immunoblots whole cell lysates for expression of fused and unfused 14CBD/A and CBD/B. As shown in FIG. 2, excellent expression of both unfused antigens and antigens fused to ClyA was observed; other experiments confirmed equivalent expression of these *C. difficile* antigens in the less attenuated isogenic parental strain of CVD 908-htrAssb called CVD 908ssb (data not shown).

An initial experiment was conducted in mice, vaccinating only with live vectors, to determine the immunogenicity of ClyA-CBD/B versus unfused CBD/B in both CVD 908-htrAssb and less attenuated parent strain CVD 908ssb live vectors. In this experiment, the immunogenicity of a non-hemolytic double mutant (DM) version of ClyA was also tested, in which the substitutions I198N and C285W were both introduced into the wildtype sequence, expressed by the pSEC10S2-DM expression plasmid. BALB/c mice were randomly assorted into 5 groups of 10 mice, and immunized on days 0, 14, and 28 with 5×10$^{9}$ colony forming units (CFU) of live vector. Sera were collected on days 0, 13, 27, 42, and 49. ELISA titers (EU/ml) against purified toxin B are shown in table 1 below. These initial results are highly promising and strongly suggest that 1] the less attenuated CVD 908ssb elicits higher anti-CBD/B titers than the highly attenuated CVD 908-htrAssb live vector, and 2] the immunogenicity of CBD/B fused to ClyA may be superior to unfused CBD/B, possibly due to cytoplasmic degradation of CBD/B as suggested in western data in FIG. 2, lane 5; breakdown of unfused CBD/A by western analysis was not observed (data not shown). The nucleotide sequences of the entire plasmids or the amino acids of the encoded antigens as shown in Table 1, below, are as follows:
pSEC10S-CBD/B nucleotide (SEQ ID NO:7); pSEC10S-CBD/B polypeptide (SEQ ID NO:8); pSEC10S2-DM-CBD/B nucleotide (SEQ ID NO:9); pSEC 10S2-DM-CBD/B polypeptide (SEQ ID NO:10); pCBD/B nucleotide (SEQ ID NO: 11); pCBD/B polypeptide (SEQ ID NO: 12). In the nomenclature scheme, plasmids with an "S" are SSB-stabilized versions of the original plasmids (i.e. pSEC10S is SSB-stabilized pSEC10). Therefore, pSEC10S2-DM is pSEC10 carrying SSB, and also carrying the double mutant (DM) of ClyA (pSEC10S2-DM).

TABLE 2

Hemolytic activity of CVD 908-htrA expressing protein fusions of ClyA fused to 14CBD/A or CDB/B.

| Strain | Hemolytic activity ($OD_{545}$) |
|---|---|
| htrA | 0.028 |
| htrA(pSEC10) | 1.231 |
| htrA(pSEC10-14CBD/A) | 0.583 |
| htrA(pSEC10-CBD/B) | 1.151 |
| Ty21a | 0.106 |

Example 2

Molecular Evolution of Non-Hemolytic Alleles of clyA

ClyA was phenotypically identified in *Salmonella* strains as a cryptic hemolysin, present in several serovars including the licensed *S. Typhi* vaccine strain Ty21a (Oscarsson J, Westermark M, Lofdahl S et al. Characterization of a pore-forming cytotoxin expressed by *Salmonella enterica* serovars *typhi* and paratyphi A. *Infect Immun.* 2002; 70:5759-5769). Although in all murine and non-human primate experiments conducted to date adverse reactions to the vaccine strains have never been observed, ClyA still possesses hemolytic activity in vitro, and could therefore theoretically be considered a virulence factor with the potential to cause adverse reactions in humans. To remove hemolytic activity from *S. Typhi* clyA, it was elected to molecularly evolve a codon-optimized allele of clyA genetically fused to the gfpuv allele of pSEC92gfpuv. Fusion of foreign protein domains to the carboxyl terminus of ClyA reduces the hemolytic activity of the ClyA domain, probably by

TABLE 1

Anti-TcdB IgG responses in mice immunized intranasaily with attenuated *S. Typhi* live vectors carrying SSB-stabilized low-copy-number expression plasmids.

| Group | Strain | Day 0 | Day 13 (after 1$^{st}$ dose) | Day 27 (after 2$^{nd}$ dose) | Day 42 (after 3$^{rd}$ dose) | Day 49 (3 wk after 3$^{rd}$ dose) |
|---|---|---|---|---|---|---|
| 1 | PBS | 12.5 | 14.4 | 14.4 | 21.0 | 14.9 $^{A}$ |
| 2 | 908-htrAssb(pSEC10S-CBD/B) | 12.5 | 35.3 | 296.4 | 1676.4 | 1618.3 $^{B}$ |
| 3 | 908ssb(pSEC10S-CBD/B) | 13.4 | 25.8 | 284.9 | 4591.3 | 5368.5 $^{C}$ |
| 4 | 908-htrAssb(pCBD/B) | 12.5 | 12.5 | 12.5 | 14.4 | 14.4 $^{D}$ |
| 5 | 908ssb(pCBD/B) | 14.4 | 15.4 | 36.0 | 154.4 | 220.3 $^{E}$ |
| 6 | 908-htrAssb(pSEC10S2-DM-CBD/B) | 13.4 | 13.4 | 13.4 | 17.5 | 19.7 |
| 7 | 908ssb(pSEC10S2-DM-CBD/B) | 12.5 | 12.5 | 12.5 | 15.8 | 14.8 |

For Day 49, the two-sided p-values from Student t-tests on the logs of antitoxin values are:
$^{C}$ vs $^{B}$ = 0.78; $^{E}$ vs $^{D}$ = 0.0001; $^{B}$ vs $^{D}$ = 0.0001; $^{B}$ vs $^{E}$ = 0.018; $^{C}$ vs $^{D}$ = 0.0001.

Quantitative hemolytic assays were performed on constructs expressing ClyA-CBD fusions, and results are summarized in Table 2 (Sansonetti, P. J., A. Ryter, P. Clerc, A. T. Maurelli, and J. Mounier. 1986. Multiplication of *Shigella flexneri* within HeLa cells: lysis of the phagocytic vacuole and plasmid-mediated contact hemolysis. *Infect. Immun.* 51:461-469). As expected, fusion of the 36.3 kDa 14CBD/A passenger domain to ClyA reduces hemolytic activity to ~50% of unfused ClyA expressed by pSEC10. Surprisingly, fusion of the larger 61.6 kDa domain of CDB/B to ClyA only reduces hemolytic activity slightly. Although the apparent export of ClyA fusions, resulting in hemolysis of RBCs, suggests successful export of ClyA fusions out of our live vectors, we recognize that introduction of non-hemolytic mutations into clyA that still preserve export will be required for clinical acceptability.

perturbing the natural folding of ClyA and possibly affecting outer membrane vesicle formation. It is therefore believed that evolving ClyA in the context of a fusion domain would increase chances of successfully switching this domain with antigens from *C. difficile* to preserve export of these vaccine antigens. Fusion of ClyA to the fluorescent reporter GFPuv was chosen since it is well documented that GFPuv will not fluoresce in the context of improperly folded upstream domains (Waldo G S, Standish B M, Berendzen J, Terwilliger T C. Rapid protein-folding assay using green fluorescent protein. *Nat Biotechnol.* 1999; 17:691-695).

Subjecting clyA to a single round of molecular evolution yielded 111 clones that appeared non-hemolytic on sheep blood agar plates, but still fluoresced. Sequencing of these mutagenized constructs revealed that 18 recombinants had single amino acid substitutions that removed hemolytic activity. These 18 constructs expressing non-hemolytic ClyA (ClyA*) were retransformed into DH5α and export of ClyA*-GFPuv into the culture supernatant was examined using Western immunoblot analysis with anti-GFP polyclonal antibody. Six individual mutations (S195N, I198N, A199D, E204K, E204D, G205D) abrogated hemolytic activity while preserving export of ClyA*-GFPuv into the supernatant. Quantitative hemolytic assays performed on these 6 ClyA variants revealed that mutations S195N, I198N, and A199D each dramatically reduced hemolytic activity to 2-8% of wildtype (Sansonetti P J, Ryter A, Clerc P, Maurelli A T, Mounier J. Multiplication of *Shigella flexneri* within HeLa cells: lysis of the phagocytic vacuole and plasmid-mediated contact hemolysis. *Infect Immun.* 1986; 51:461-469). The G205D mutation reduced the hemolytic activity to less than 50%. Interestingly, the 2 mutations at residue 204 (E204K, E204D) reduced hemolytic activity to different degrees, depending on which amino acid replaced the wildtype glutamic acid. The E204D substitution reduced hemolytic activity to 30% of wildtype, while the E204K substitution reduced hemolysis to less than 2%. These results demonstrate that hemolytic activity and export activity can be separated, and illustrate the power of using random molecular evolution to engineer desired phenotypes.

Figure 3:
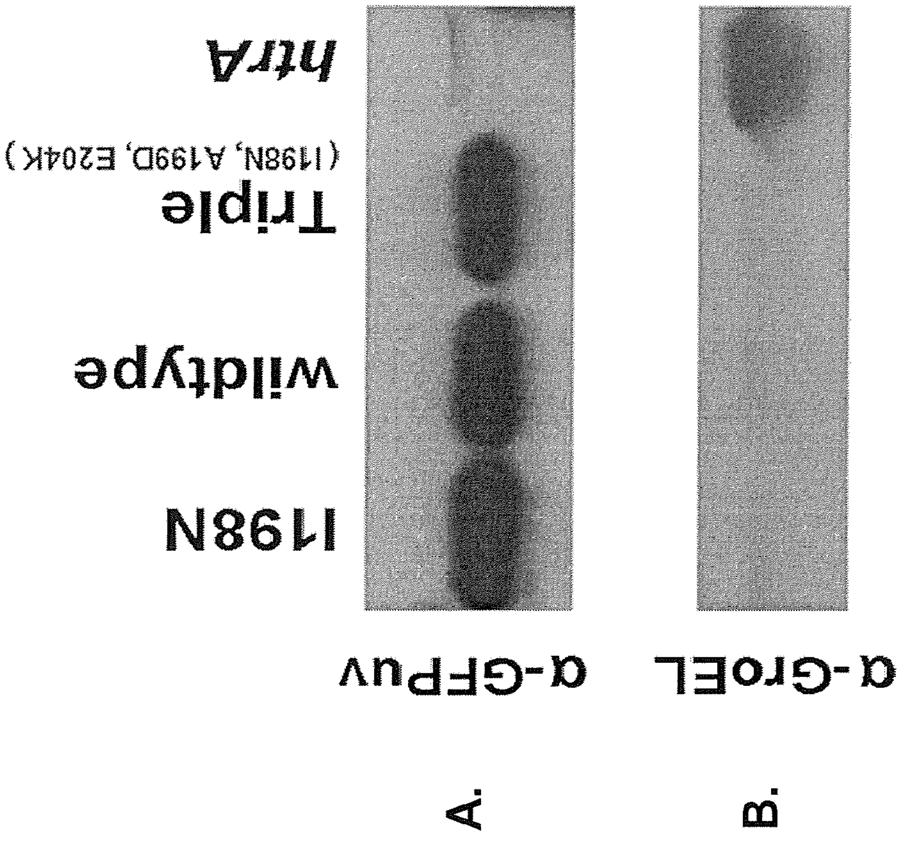
FIG. 3. Western immunoblot of culture supernatants from DH5αexpressing non-hemolytic fusions of ClyA fused to the fluorescent reporter protein GFPuv (ClyA*-GFPuv) or wildtype ClyA-GFPuv protein. (A.) Culture supernatants stained with anti-GFP polyclonal antibody to detect properly exported ClyA*-GFPuv fusions. (B.) Culture supernatants stained with polyclonal antibody against the cytoplasmic protein GroEL; a lysate of CVD 908-htrA (pClyA-GFPuv) was included as a control for background autolysis of live vectors.

A triple mutant clyA* gene containing the mutations of I198N, A199D, and E204K was genetically engineered. Plasmids expressing single or triple mutant ClyA* were introduced into CVD 908-htrA and the resulting live vector constructs tested both for hemolytic activity and export of ClyA*-GFPuv into the culture supernatant. Export of the triple mutant fusion was identical to that observed for wildtype ClyA-GFPuv, as judged by western immunoblot analysis of culture supernatants (FIG. 3A); note that the absence of GroEL in the supernatants strongly suggests that ClyA fusions are being exported into the supernatant in the absence of detectable autolysis (FIG. 3B).

Figure 4:
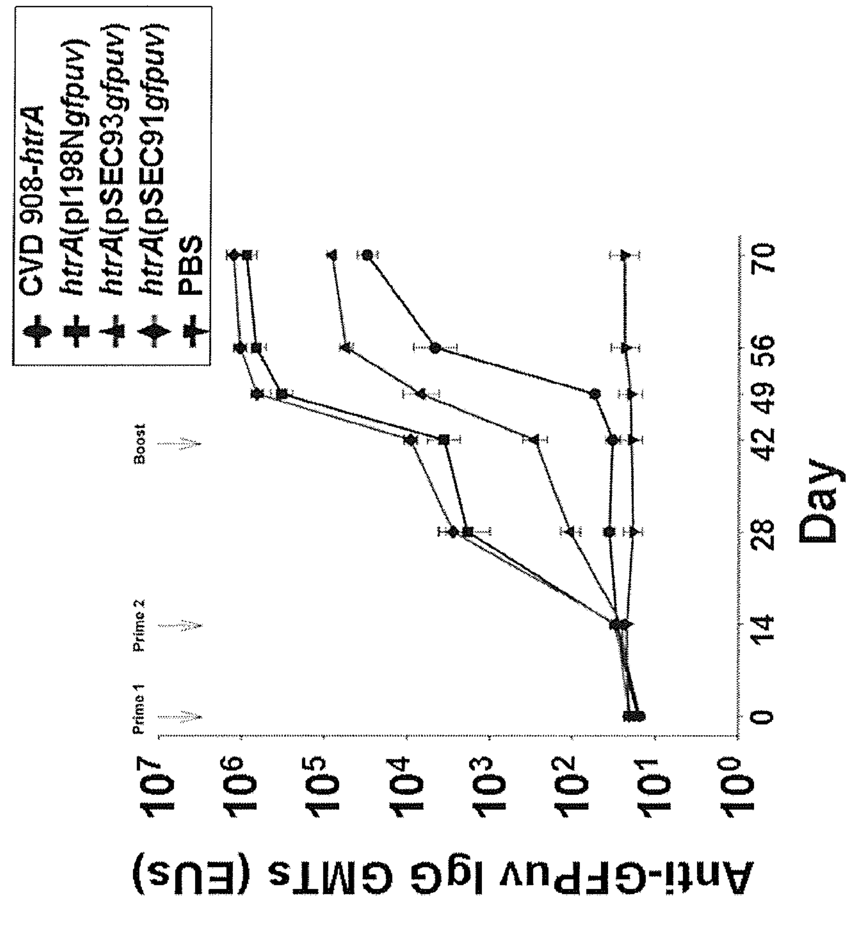
FIG. 4. Immunogenicity of attenuated *S. Typhi* CVD 908-htrA in mice using a heterologous mucosal prime-parenteral boost strategy. Animals were immunized intranasally on days 0 and 14 with $5\times10^9$ colony forming units (CFU) of plasmid-bearing live vectors, and boosted intramuscularly on day 42 with 0.5 μg purified GFPuv adsorbed to 0.5 mg Alhydrogel in a total volume of 50 μl. Mice were immunized with live vectors carrying medium copy number expression plasmids encoding GFPuv fused to the carboxyl terminus of ClyA, in which ClyA also contained either: 1] a single mutation abolishing hemolytic activity (pI198Ngfpuv); 2] the set of triple mutations I198N,A199D, E204K abolishing hemolytic activity (pSEC93gfpuv); or 3] wildtype ClyA (pSEC91gfpuv). CVD 908-htrA was included as an empty vector control.

The immunogenicity of these single and triple ClyA*-GFPuv mutants was then tested using the murine intranasal model of immunogenicity. Mice were primed with $5\times10^9$ CFU of plasmid-bearing live vectors on days 0 and 14, and boosted intramuscularly on day 42 with 0.5 μg purified GFPuv adsorbed to 0.5 mg Alhydrogel in a total volume of 50 μl. Results are shown in FIG. 4. As expected, wildtype ClyA-GFPuv fusions encoded by pSEC91gfpuv were highly immunogenic, with serum IgG titers rising 100 fold after the second priming dose of live vector was given. The immunogenicity of the single I198N non-hemolytic mutant encoded by pI198Ngfpuv was indistinguishable from that of the wildtype fusion. Surprisingly, the triple mutant ClyA*-GFPuv fusion encoded by pSEC93gfpuv was poorly immunogenic, eliciting GFPuv-specific titers 10 fold less than wildtype and single mutant constructs. These data suggest that if the folding of ClyA is significantly perturbed by the accumulation of point mutations that abolish hemolytic activity, the immunogenicity of the passenger domain (GFPuv in this case) is reduced.

Example 3

Immunogenicity in Mice of PA83 Delivered by SSB-Stabilized Plasmids in CVD 908-htrA and CVD 908

To further improve the clinical acceptability of the live vector vaccine, a non-antibiotic plasmid selection system has been developed for use in attenuated bacterial vaccine strains. Typically, foreign proteins are expressed within live vectors from multicopy expression plasmids that do not encode transfer functions and are not considered to be self-transmissible. Antibiotic resistance markers are usually inserted into expression plasmids for selection purposes after introduction of plasmids into live vectors. Until recently, these resistance markers were considered to pose no risk for complicating or causing failure of clinical antimicrobial treatments for 3 important reasons: 1] the expression plasmids (and accompanying resistance markers) could not be efficiently mobilized from live vector donors to a recipient, 2] the genes used encoded resistance to antibiotics not in widespread medical use, and 3] with no relevant antibiotic selective pressure, even rare plasmid transfers would not lead to de novo resistances becoming established within a new bacterial population (Levine, M. M., J. B. Kaper, H. Lockman, R. E. Black, M. L. Clements, and S. Falkow. 1983. Recombinant DNA risk assessment studies in humans: efficacy of poorly mobilizable plasmids in biologic containment. J. Infect. Dis. 148:699-709). However, the Food and Drug Administration is now recommending that all vaccines intended for use as mucosal vaccines in humans be free of resistance to antibiotics. Therefore, the clinical acceptability of the live vector vaccines has been improved by engineering an ssb—derived selection system for the expression plasmids.

Figure 5:
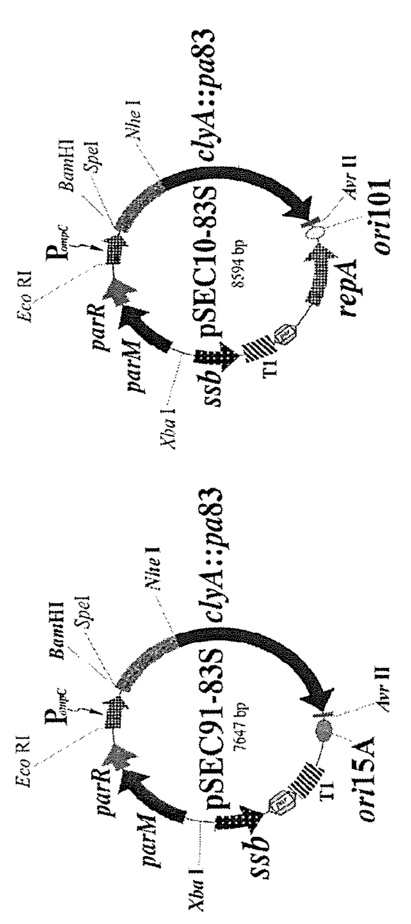
FIG. 5. SSB-stabilized medium copy (pSEC91-83S, ~15 copies per chromosomal equivalent) or low copy (pSEC10-83S, ~5 copies per chromosomal equivalent) plasmids in which PA83 is fused to ClyA.

A set of isogenic expression plasmids was engineered in which PA83 fused to ClyA was expressed from SSB-stabilized medium copy (pSEC91-83S, ~15 copies per chromosomal equivalent) or low copy (pSEC10-83S, ~5 copies per chromosomal equivalent) plasmids (FIG. 5). Plasmids were introduced into either CVD 908-htrAssb or the less attenuated parent CVD 908ssb. As a control, the immunogenic CVD 908-htrA (pSEC91-83) was included from previous non-human primate studies. Immunogenicity of these constructs was tested in BALB/c mice primed intranasally on days 0 and 14 with $5\times10^9$ cfu of live vector and boosted intramuscularly 28 days later (day 42) with 10 μg purified PA83 (List Biochemical Laboratories) adsorbed to Alhydrogel in a total volume of 50 μl. Preliminary results with pooled sera are shown in Table 3 (serum IgG) (see Galen J E, M. Chinchilla, M. F. Pasetti, J. Y. Wang, L. Zhao, I. Arciniega-Martinez, D. J. Silverman, and M. M. Levine. Mucosal immunization with attenuated *Salmonella Typhi* expressing anthrax PA83 primes monkeys for accelerated serum antibody responses to parenteral PA83 vaccine. *J. Infect. Dis.* 2009. 199: 326-35).

TABLE 3

Anti-PA83 IgG responses in pooled serum from mice immunized intranasally with PA83-expressing *S. Typhi* live vectors and boosted with purified PA83.

| Group | Strain | Plasmid Copy number | Foreign Antigen | SSB? | Day 41 (pre-boost) | Day 49 (1 wk post boost) | Day 55 (2 wks post boost) | Day 70 (4 wks post boost) |
|---|---|---|---|---|---|---|---|---|
| 1 | htrAssb(pSEC91dS) | ~15 | (–) control | YES | 25 | 1,105 | 5,690 | 41,824 |
| 2 | htrAssb(pSEC91-83S) | ~15 | ClyA-PA83 | YES | 25 | 2,944 | 80,710 | 598,700 |

TABLE 3-continued

Anti-PA83 IgG responses in pooled serum from mice immunized intranasally with PA83-expressing *S. Typhi* live vectors and boosted with purified PA83.

| Group | Strain | Plasmid Copy number | Foreign Antigen | SSB? | Day 41 (pre-boost) | Day 49 (1 wk post boost) | Day 55 (2 wks post boost) | Day 70 (4 wks post boost) |
|---|---|---|---|---|---|---|---|---|
| 3 | htrAssb(pSEC10-83S) | ~5 | ClyA-PA83 | YES | 4,436 | 314,166 | 475,045 | 209,389 |
| 4 | 908ssb(pSEC91dS) | ~15 | (−) control | YES | 25 | 25 | 8,484 | 206,628 |
| 5 | 908ssb(pSEC91-83S) | ~15 | ClyA-PA83 | YES | 2,631 | 296,222 | 630,795 | 1,180,372 |
| 6 | 908ssb(pSEC10-83S) | ~5 | ClyA-PA83 | YES | 18,431 | 856,485 | 1,219,323 | 504,111 |
| 7 | htrA(pSEC91-83) | ~15 | ClyA-PA83 | NO | 442.9 | 108,283 | 108,283 | 755,215 |

Surprisingly, humoral responses engendered using CVD 908-htrAssb(pSEC91-83S), carrying an SSB-stabilized medium copy expression plasmid were clearly lower than responses elicited by the conventional CVD 908-htrA (pSEC9'-83) live vector, carrying the kanamycin resistance medium copy pSEC91-83 plasmid (group 2 versus group 7). Prior to boosting (day 41), anti-PA83 responses were 10 fold lower for SSB-stabilized constructs versus conventional constructs, and responses for these two strains did not converge until 4 weeks after the boost. However, when the copy number for SSB-stabilized plasmids was reduced, serum responses with CVD 908-htrAssb(pSEC10-83S) rose 10 fold versus conventional CVD 908-htrA(pSEC91-83) on day 41, and remained elevated 2 weeks after boosting (group 3 versus group 7). These data clearly suggest that as copy number is reduced, the immunogenicity of the foreign antigen improves. It is believed that this effect is due to the reduced metabolic burden associated with the lower copy number of pSEC10-83S. Indeed, when pSEC10-83S is carried by the less attenuated CVD 908ssb live vector, immunogenicity of the foreign antigen increases yet again and remains elevated 4 weeks post boost (group 3 versus group 6). Here it is stressed that CVD 908-htrAssb and CVD 908ssb are isogenic strains, differing only in the deletion of a single htrA chromosomal locus. However, identical expression plasmids elicit higher serum antibody responses in the less attenuated CVD 908ssb live vector than when carried by CVD 908-htrAssb. It is believed that any metabolic burden still associated with pSEC10-83S is compensated for in the less attenuated background of CVD 908ssb. Based on these highly encouraging data, the immunogenicity will be examined of *C. difficile* antigens expressed using low copy number pSEC10 expression plasmids, genetically stabilized with the SSB system, and carried either by CVD 908-htrAssb or CVD 908ssb.

Example 4

Genetic Stability of SSB-Stabilized Plasmids Expressing GFPuv

Figure 6:
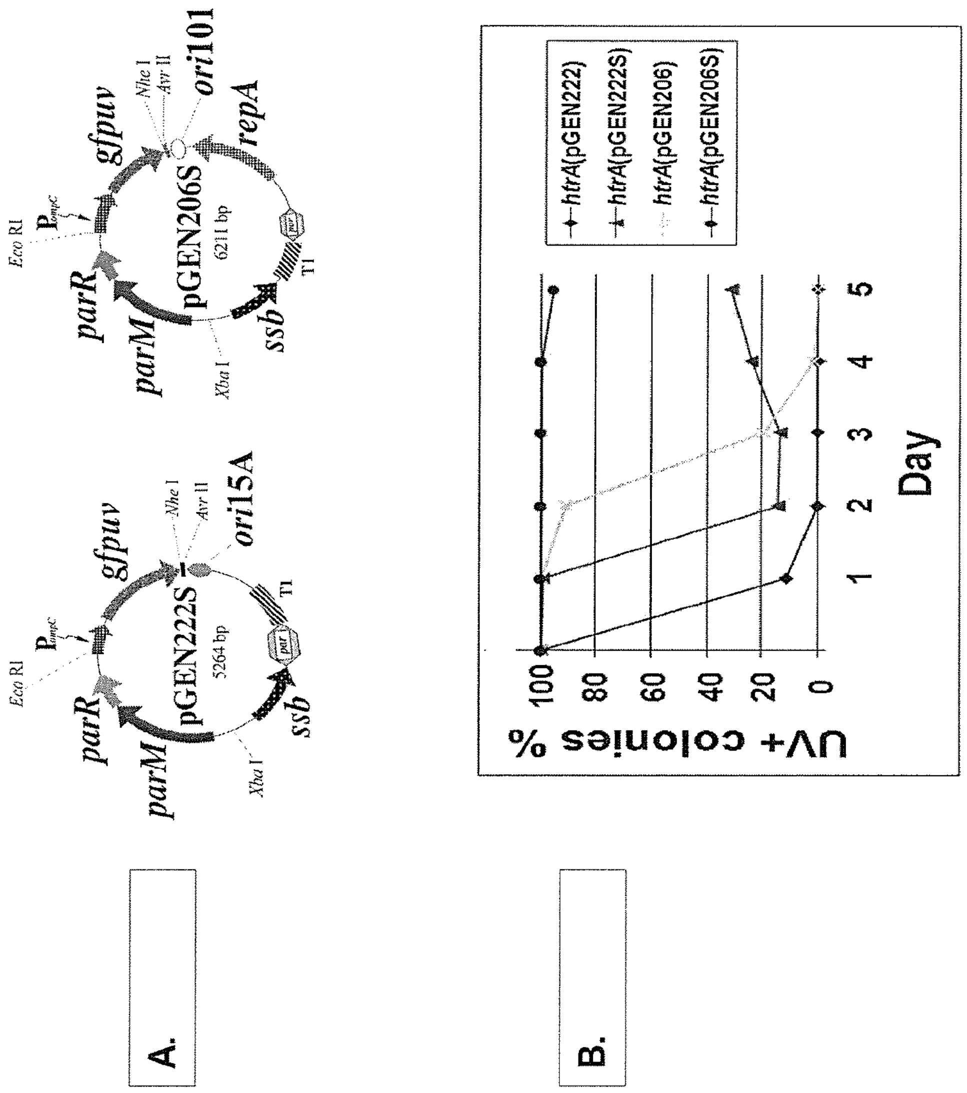
FIG. 6. (A) Isogenic SSB-stabilized versions of pGEN222 and pGEN206. (B) After electroporating these four isogenic expression plasmids into CVD 908-htrA, the desired live vector strains were recovered, and an in vitro plasmid stability experiment was carried out. Viable counts were recovered on non-selective medium, and the percentage of fluorescing colonies determined.

The 10-fold drop in immunogenicity of ClyA-PA83 delivered using SSB-stabilized pSEC91-83S versus conventional pSEC91-83 suggested that perhaps SSB-stabilized higher copy number plasmids encoding a potentially toxic foreign protein may lead to genetic instability and perhaps rearrangements or deletions of foreign genes from the expression plasmid. To investigate this further, previously described GFPuv-encoding plasmids pGEN222 and pGEN206 were tested (Galen, J. E., J. Nair, J. Y. Wang, S. S. Wasserman, M. K. Tanner, M. Sztein, and M. M. Levine. 1999. Optimization of plasmid maintenance in the attenuated live vector vaccine strain *Salmonella Typhi* CVD 908-htrA. Infect. Immun. 67:6424-6433; Stokes, M. G., R. W. Titball, B. N. Neeson, J. E. Galen, N. J. Walker, A. J. Stagg, D. C. Jenner, J. E. Thwaite, J. P. Nataro, L. W. Baillie, and H. S. Atkins. 2007. Oral administration of a *Salmonella enterica*-based vaccine expressing *Bacillus anthracis* protective antigen confers protection against aerosolized *B. anthracis. Infect. Immun.* 75:1827-1834). The expected copy number of pGEN222 is 15 copies per chromosomal equivalent, and that of pGEN206 is 5 copies per chromosomal equivalent. Isogenic SSB-stabilized versions of pGEN222 and pGEN206 were engineered, as shown in FIG. 6A. After electroporating these four isogenic expression plasmids into CVD 908-htrA, the desired live vector strains were recovered, and an in vitro plasmid stability experiment was carried out. Frozen stocks were streaked onto appropriately supplemented solid media, and incubated at 30° C. for 48 hours to obtain isolated colonies. 2-3 fluorescing colonies were then inoculated into 20 ml liquid medium without selection and incubated shaking at 225 rpm overnight at 30° C. (0 hour starting cultures for serial passages). Overnight starter cultures were then diluted 1:50 into fresh non-selective medium, incubated for 24 hr at 37° C., and then serially passaged every 24 hours in the same way for 5 days. Viable counts were recovered on non-selective medium, and the percentage of fluorescing colonies determined, as reported in FIG. 6B. As expected, conventional plasmids were unstable, with less than 20% of strains carrying pGEN222 remaining fluorescent after passage for 24 hr; live vectors maintained the lower copy number pGEN206 for 48 hr, but then plasmid-bearing strains dropped precipitously on day 3. Surprisingly, the fluorescence of strains carrying SSB-stabilized pGEN222S dropped precipitously after 24 hr, despite the fact that these plasmids encode the essential ssb gene. It is expected that the higher copy number pGEN222S constructs encoding GFPuv are toxic, possibly leading to non-homologous integration into the chromosome accompanied by loss of the foreign antigen-encoding gene (in this case gfpuv). Notably, the observed stability of the low copy number SSB-stabilized pGEN206S plasmid was excellent after 120 hours of culturing in the absence of selection. This observation potentially explains the superior immunogenicity of pSEC 10-83S constructs versus the higher copy number pSEC91-83S plasmids reported in Table 2, and again supports the use of pSEC10 plasmids for expression of potentially toxic *C. difficile* foreign antigens.

Example 5

Preparation of an Attenuated Bacterial Strain Derived from *S. Typhi* Ty2 and Carrying Deletions in both guaBA and htrA A new vaccine strain will be constructed, carrying deletions in guaBA and htrA, which will be attenuated within half the logarithmic value of CVD 908-htrA.

Deletion cassettes, targeting guaBA and htrA, for use with the lambda Red-mediated site-directed mutagenesis method will be used to successfully delete either guaBA or htrA from wildtype *S. Typhi* Ty2 (Datsenko K A, Wanner B L. One-step inactivation of chromosomal genes in *Escherichia coli* K-12 using PCR products. *Proc Natl Acad Sci USA.* 2000; 97:6640-6645). The deletion cassettes will be introduced into a single strain, creating CVD 910. The degree of attenuation of CVD 910 will be assessed by comparing the minimum lethal dose causing death in 50% of a group of BALB/c mice (LD50) for CVD 910 versus both CVD 908-htrA and its wildtype parent Ty2, using the hog gastric mucin intraperitoneal murine challenge model. For this model, the guidelines recommended in the Code of Federal Regulations for Food and Drugs, Title 21, Part 620.13 (c-d), 1986 for intraperitoneal challenge of mice with *S. Typhi* will be followed. Using this method the LD50 of an attenuated strain of Ty2, carrying a single deletion in guaBA, was observed to be $7.7\times10^7$ CFU, versus an LD50 of 140 CFU for wildtype Ty2 and $>5\times10^9$ CFU for CVD 908-htrA (unpublished observations) (Wang J Y, Pasetti M F, Noriega F et al. Construction, genotypic and phenotypic characterization, and immunogenicity of attenuated DguaBA *Salmonella enterica* serovar *Typhi* strain CVD 915. *Infect Immun.* 2001; 69:4734-4741). An LD50 of between 1 and $5\times10^9$ CFU will be acceptable for use of CVD 910 in the development of the proposed *C. difficile* vaccine.

The immunogenicity of CVD 910 will then be compared to that of CVD 908-htrA using the murine intranasal model of immunogenicity. Adult BALB/c mice will be randomized into three groups and immunized with either CVD 910, CVD 908-htrA, or PBS. Mice will be immunized intranasally on days 0 and 14 with $5\times10^9$ CFU of attenuated vaccine. Serum IgG antibody responses to both lipopolysacchriade (LPS) and flagella (H antigen) will be measured on days 0, 14, 28, and 42 to confirm comparable humoral immune responses against CVD 910 versus CVD 908-htrA.

One antigen (e.g., TcdB) will be expressed on a low copy number SSB-stabilized expression plasmid, and the other antigens (TcdA and CdtB) will be integrated into the deleted loci of the attenuated *S. Typhi* strain derived from wildtype Ty2

Example 6

Expression of Cell-Binding Domains from *C. difficile* Enterotoxins A (TcdA), B (TcdB), or Binary Toxin (CdtB) from Plasmids in an Attenuated *S. Typhi* Vaccine Strain and Testing for Toxin-Specific Antibody Responses in Mice using a Heterologous Prime-Boost Strategy SSB-stabilized low copy (~5 copies per chromosomal equivalent) expression plasmids encoding either a truncated version of the Cell Binding Domain of TcdA (14CBD/A) or the full-length Cell Binding Domain of TcdB (CBD/B) were constructed. Plasmids were constructed encoding 14CBD/A and CBD/B expressed either cytoplasmically or exported out of the cytoplasm as a fusion to ClyA. Transcription of these cassettes is osmotically controlled by a $P_{ompC}$ promoter (Galen J E, Nair J, Wang if et al. Optimization of plasmid maintenance in the attenuated live vector vaccine strain *Salmonella Typhi* CVD 908-htrA. *Infect Immun.* 1999; 67:6424-6433). When introduced into the live vector CVD 908-htrAssb, excellent expression as judged by western immunoblotting using toxin specific sera was observed (see Example 1), and CVD 908-htrAssb expressing ClyA-CBD/B fusions proved immunogenic using a murine intranasal model of immunogenicity (Table 1). Since ClyA possesses hemolytic activity in vitro, ClyA can theoretically be considered a virulence factor, a concern that could complicate moving forward into future clinical trials. To improve the clinical acceptability of the trivalent vaccine strain, the immunogenicity of *C. difficile* antigens fused to a modified version of ClyA, in which hemolytic activity has been removed by introducing the substitution of a hydrophilic arginine residue for the hydrophobic wildtype isoleucine residue 198 (I198N) will be examined; preliminary data indicate that this substitution abolishes hemolytic activity while preserving export of a carboxyl-terminal biologically active fusion of GFPuv. This non-hemolytic allele is referred to as ClyA*, encoded by clyA*. It will be confirmed that all ClyA* fusions are non-hemolytic using a previously described quantitative hemolysis assay (Sansonetti P J, Ryter A, Clerc P, Maurelli A T, Mounier J. Multiplication of *Shigella flexneri* within HeLa cells: lysis of the phagocytic vacuole and plasmid-mediated contact hemolysis. *Infect Immun.* 1986; 51:461-469).

Six low copy SSB-stabilized expression plasmids encoding the cell-binding domains of either TcdA (14CBD/A), TcdB (CBD/B), or binary toxin (CBD/BT), and expressed either cytoplasmically or exported from the cytoplasm as fusions to non-hemolytic ClyA (I198N) will be constructed. All cassettes will be transcriptionally controlled by the osmotically inducible $P_{ompC}$ promoter (Galen J E, Nair J, Wang J Y et al. Optimization of plasmid maintenance in the attenuated live vector vaccine strain *Salmonella Typhi* CVD 908-htrA. *Infect Immun.* 1999; 67:6424-6433). ssb from CVD 910 will be deleted to generate a live vector analogous to previous CVD 908-htrAssb, creating CVD 910ssb. Upon completion, the six expression plasmids will be introduced into CVD 910ssb by electroporation as previously described (Galen J E, Wang J Y, Chinchilla M et al. A new generation of stable, nonantibiotic, low-copy-number plasmids improves immune responses to foreign antigens in *Salmonella enterica* serovar *Typhi* live vectors. *Infect Immun.* 2010; 78:337-347). The immunogenicity of the resulting strains will be tested using a heterologous mucosal prime-parenteral boost immunization strategy to identify the most immunogenic way to deliver each of the *C. difficile* antigens (i.e. fused or unfused). Adult BALB/c mice will be randomized into 7 groups and primed with CVD 910ssb live vectors expressing the following *C. difficile* antigens:

group 1) ClyA*-14CBD/A fusion protein,
group 2) Unfused 14CBD/A,
group 3) ClyA*-CBD/B fusion protein,
group 4) Unfused CBD/B,
group 5) ClyA*-CBD/BT fusion protein
group 6) Unfused CBD/BT
group 7) CVD 910ssb carrying an empty plasmid encoding SSB Mice will be primed intranasally on days 0 and 14 with a dose of $5\times10^9$ CFU, and boosted intramuscularly on day 42 with homologous antigen adsorbed to alum; use of this immunization strategy was demonstrated by our group to elicit neutralizing antibody responses against anthrax toxin when used with both mice and non-human primates (Galen J E, Chinchilla M, Pasetti M F et al. Mucosal immunization with attenuated *Salmonella enterica* serovar *Typhi* expressing protective antigen of anthrax toxin (PA83) primes monkeys for accelerated serum antibody responses to parenteral PA83 vaccine. *J Infect Dis.* 2009; 199:326-335). Boosting antigens will be purified. Serum IgG antibody responses will be measured by ELISA on days 0, 14, 28, 42, 56, and 70. To more fully characterize the breadth of immune responses, enterotoxin-specific fecal IgA antibody responses will be determined on day 70, as an indicator of mucosal immunity (Lasaro M O, Luiz W B, Sbrogio-Almeida M E, Ferreira L C. Prime-boost vaccine regimen confers protective immunity to human-derived enterotoxigenic *Escherichia coli. Vaccine.* 2005; 23:2430-2438). However, a primary endpoint for immunity against TcdA and TcdB will be serum neutralizing antitoxin responses on days 56 and 70, measured using IMR-90 cells which are sensitive to both toxin A and toxin B. Biologically active holotoxins A and B, to be used in the neutralization assays and as the coating antigen for ELISA analyses, will be provided. Neutralization assays have been established for other toxins including tetanus toxin and anthrax toxin (Galen J E, Gomez-Duarte O G, Losonsky G et al. A murine model of intranasal immunization to assess the immunogenicity of attenuated *Salmonella Typhi* live vector vaccines in stimulating serum antibody responses to expressed foreign antigens. *Vaccine.* 1997; 15:700-708; Galen J E, Chinchilla M, Pasetti M F et al. Mucosal immunization with attenuated *Salmonella enterica* serovar *Typhi* expressing protective antigen of anthrax toxin (PA83) primes monkeys for accelerated serum antibody responses to parenteral PA83 vaccine. *J Infect Dis.* 2009; 199:326-335). Anti-Cdt immunity will be examined by measuring serum IgG antibody responses against CBD/BT on days 56 and 70 for fused versus unfused CBD/BT, as well as Cdt-specific fecal IgA on day 70 (Lasaro M O, Luiz W B, Sbrogio-Almeida M E, Ferreira L C. Prime-boost vaccine regimen confers protective immunity to human-derived enterotoxigenic *Escherichia coli. Vaccine.* 2005; 23:2430-2438).

If expression of a truncated version of the carboxyl terminus of toxin A does not elicit neutralizing antibodies, then additional cassettes will be inserted encoding the remaining repeat regions to improve folding and immunogenicity of the larger protein. In the unlikely event that the I198N substitution diminishes the immunogenicity of ClyA*-CBD/B, possibly indicating improper folding of this fusion compared to previous success with hemolytic ClyA-CBD/B, other previously identified non-hemolytic mutations including A199D or E204K will be tested.

Example 7

Chromosomal Integration of Cassettes Encoding *C. difficile* Antigens Generates a Multivalent Strain and Testing the Strain in Mice using a Heterologous Prime-Boost Strategy Immunogenic cassettes will be integrated into either the ΔguaBA or ΔhtrA locus of CVD 910ssb, to compare the immunogenicity of chromosomal integrations versus antigen-specific immunogenicity elicited by plasmid-based expression. For the engineering of the ΔguaBA and ΔhtrA attenuating deletions of CVD 910ssb, only the open reading frames were deleted, leaving the original promoters for these sites intact. Therefore, to compensate for loss of copy number with chromosomal expression, cassettes will include the $P_{ompC}$ promoter from the low copy expression plasmids, such that integration into ΔguaBA or ΔhtrA results in nested promoters controlling inducible expression of a given cassette at two levels. For example, integration of a $P_{ompC}$-clyA*-14cbd/a cassette (encoding the ClyA*-14CBD/A fusion) into ΔguaBA of CVD 910ssb would result in inducible transcription of clyA*-14cbd/a with both growth rate and osmolarity, as shown in FIG. 9. This will generate a bivalent live vector to be used in Example 8 for creation of the final trivalent live vector vaccine.

All chromosomal integrations will first be introduced into CVD 910, prior to final introduction of the ssb deletion to generate strains that can be compared to plasmid-bearing CVD 910ssb strains. Three separate mouse experiments will then be carried out, testing the immunogenicity of chromosomally integrated genetic cassettes; the objective of these experiments is to identify which chromosomal integrations elicit antigen-specific immunogenicity comparable to that observed for plasmid-based expression. It is assumed that the most immunogenic cassettes encode fusions of ClyA* fused to 14CBD/A (encoded by clyA*-14cbd/a) or CBD/B (encoded by clyA*-cbd/b), while CBD/BT remains unfused. For all experiments, BALB/c mice will be randomly assorted into groups, immunized intranasally on days 0 and 14 with 5×10$^9$ CFU of live vector, and then boosted intramuscularly on day 42 with homologous purified antigen adsorbed to alum. Study 1, below, will determine how chromosomal expression of optimized genetic cassettes encoding *C. difficile* antigens integrated into the guaBA locus compares with plasmid-based expression of the identical antigen cassette:

group 1) 910ssb ΔguaBA::clyA*-14cbd/a
group 2) 910ssb (pClyA*-14CBD/A)
group 3) 910ssb ΔguaBA::clyA*-cbd/b
group 4) 910ssb (pClyA*-CBD/B)
group 5) 910ssb ΔguaBA::cbd/bt
group 6) 910ssb (pCBD/BT)
group 7) 910ssb carrying only the empty plasmid encoding SSB Study 2 examines how chromosomal expression of *C. difficile* antigens integrated into the htrA locus will compare with plasmid-based expression of the identical antigen cassette:

group 1) 910ssb ΔhtrA::clyA*-14cbd/a
group 2) 910ssb (pClyA*-14CBD/A)
group 3) 910ssb ΔhtrA::clyA*-cbd/b
group 4) 910ssb (pClyA*-CBD/B)
group 5) 910ssb ΔhtrA::cbd/bt
group 6) 910ssb (pCBD/BT) group 7) 910ssb carrying only the empty plasmid encoding SSB.

For Study 3, the most immunogenic chromosomal integrations identified in the previous two previous experiments will be introduced into a single bivalent strain and compare the immunogenicity of both integrated antigens to plasmid-based expression of the identical antigen cassette in monovalent strains. It is assumed that ΔguaBA::clyA*-14cbd/a and ΔhtrA::clyA*-cbd/b elicit antigen-specific immunogenicity comparable to that observed for plasmid-based expression. Therefore, in this particular scenario, it is assumed that the immunogenicity of chromosomally integrated CBD/BT will be found to be significantly less than plasmid-based expression, so pCBD/BT will be used to construct the final trivalent vaccine. Therefore, BALB/c mice will be randomly assorted into 4 groups for intranasal immunization with:

group 1) 910ssb ΔguaBA::clyA*-14cbd/a ΔhtrA::clyA*-cbd/b
group 2) 910ssb (pClyA*-14CBD/A)
group 3) 910ssb (pClyA*-CBD/B)
group 4) 910ssb carrying only the empty plasmid encoding SSB Mice will be immunized intranasally with live vectors on days 0 and 14 and boosted intramuscularly with a mixture of the three purified antigens adsorbed to alum. For all 3 studies, toxin-specific serum IgG antibody responses will be measured on days 0, 14, 28, 42, 56 and 70, and fecal IgA on day 70. The primary endpoints will be 1] serum neutralizing antitoxin responses against TcdA and TcdB on days 56 and 70, measured using IMR-90 cells, and 2] Cdt-specific fecal IgA on day 70.

These studies will allow final construction of the multivalent vaccine, in which two *C. difficile* antigens are efficiently expressed from the chromosome and the remaining antigen is expressed from a low copy SSB-stabilized plasmid. It is possible that chromosomal integration of *C. difficile* antigens fused to ClyA* will integrate into the wildtype clyA locus present in CVD 910ssb, rather than guaBA or htrA. If the presence the wildtype clyA allele causes improper integration of incoming cassettes, wildtype clyA from the live vector chromosome can be deleted. This deletion is not expected to further attenuate the resulting live vector.

Example 8

Figure 10:
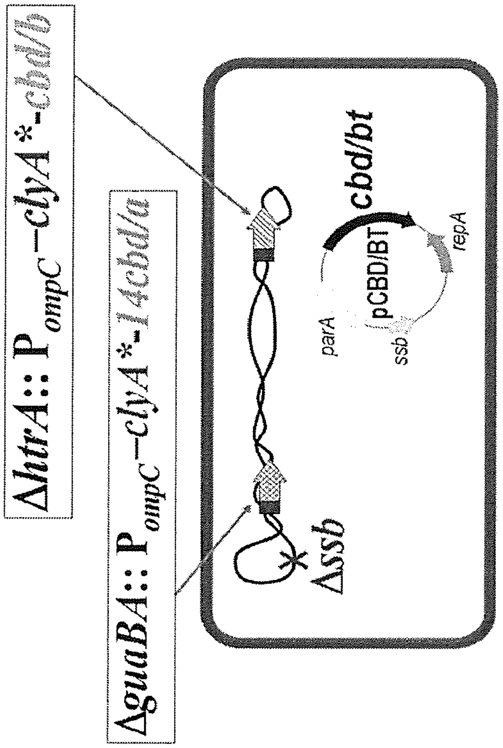
FIG. 10. Attenuated *S. Typhi*-based trivalent live vector vaccine against recurrent *C. difficile* infections (RCDD. Genetic fusions encoding the non-hemolytic clyA* antigen export protein fused to the cell-binding domain of TcdA (clyA*-14cbd/a) or TcdB (clyA*-cbd/b) are depicted as chromosomal insertions into the deleted guaBA and htrA loci of CVD 910ssb respectively. The remaining CBD/BT antigen of this trivalent vaccine is encoded by the low copy number SSB-stabilized plasmid, pCBD/BT, which also encodes a plasmid inheritance function (parA) and the plasmid replication protein repA.

Immunization of Hamsters with a Trivalent Live Vector Vaccine Expressing Cell-Binding Domains from TcdA, TcdB, and Cdt, Followed by Oral Challenge with *C. Difficile* Spores An SSB-stabilized expression plasmid encoding the remaining *C. difficile* antigen will be introduced into the final bivalent live vector vaccine identified in the above example. Assuming the bivalent strain to be 910ssb ΔguaBA::clyA*-14cbd/a ΔhtrA::clyA*-cbd/b, a trivalent vaccine is represented in FIG. 10. Prior to challenge experiments, the immunogenicity of the trivalent live vector in Syrian golden hamsters immunized intranasally will be established. Two experiments will be performed, testing both a heterologous mucosal live vector prime-intramuscular boost immunization strategy (as was done for mice; Study 1), as well as reversing the order and administering an intramuscular prime-mucosal live vector boost (Study 2). Using live vectors as a mucosal boost tests an immunization strategy that more closely resembles the proposed manner in which the trivalent vaccine would be used in a clinical setting to vaccinate patients recovering from a primary CDL Study 1:

group 1) mucosal priming with trivalent 910ssb expressing 14CBD/A, CBD/B, and CBD/BT antigens, and boosting with purified antigens group 2) mucosal priming with bivalent 910ssb expressing 14CBD/A and CBD/B antigens only, and boosting with purified antigens group 3) mucosal priming with monovalent 910ssb expressing only CBD/BT and boosting with purified antigens group 4) mucosal priming with 910ssb carrying only the empty plasmid encoding SSB, boosting with purified antigens Study 2:

group 1) priming with purified antigens, mucosal boosting with trivalent 910ssb expressing 14CBD/A, CBD/B, and CBD/BT group 2) priming with purified antigens, mucosal boosting with bivalent 910ssb expressing 14CBD/A and CBD/B antigens only group 3) priming with purified antigens, mucosal boosting with monovalent 910ssb expressing only CBD/BT group 4) priming with purified antigens, mucosal boosting with 910ssb carrying only the empty plasmid encoding SSB For priming with live vectors (Study 1), animals will be immunized intranasally on days 0 and 14 with $5\times10^9$ CFU of the vaccine strains and boosted intramuscularly with purified antigens plus alum on day 42. For boosting with live vectors (Study 2), animals will be primed intramuscularly on day 0 with purified antigens plus alum and boosted on days 28 and 42 with live vectors. As with the mouse experiments, toxin-specific IgG antibody responses will be measured by ELISA on days 0, 14, 28, 42, 56, and 70, with serum neutralizing enterotoxin responses measured on days 56 and 70.

Upon confirming the most immunogenic of these two strategies in hamsters, an identical intranasal immunization protocol will be carried out, prior to orogastric challenge with *C. difficile* spores. Two weeks after administration of the booster dose (day 56), hamsters will be then treated with clindamycin administered intraperitoneally 24 hrs prior to orogastric challenge with 100 colony-forming units of *C. difficile* spores. Animals will be scored for mortality over a 5 day period. With this protocol, 100% of unimmunized animals succumb to disease between 36 and 72 hrs after spore challenge (Babcock G J, Broering T J, Hernandez H J et al. Human monoclonal antibodies directed against toxins A and B prevent *Clostridium difficile*-induced mortality in hamsters. *Infect Immun.* 2006; 74:6339-6347). It is expected that there will be 100% mortality for animals in group 4 that receive only a single dose of purified antigens. It is expected that hamsters in group 1, primed with trivalent live vectors and boosted with purified antigens, will be fully protected from challenge with an epidemic strain of *C. difficile*. By contrasting protection in group 1 with that of groups 2 and 3, the relative contributions to protection of enterotoxin immunity (group 2) versus immunity to binary toxin (group 3) will be determined.

Studies 1 and 2 of this example can be repeated using C57BL/6 mice and the murine *C. difficile* challenge model recently described by Chen et al. (Chen X, Katchar K, Goldsmith J D et al. A mouse model of *Clostridium difficile*-associated disease. Gastroenterology. 2008; 135:1984-1992).

It is expected that these examples will result in an *S. Typhi*-based live vector vaccine against CDI and it is further expected to provide broad humoral and mucosal immunogenicity in humans that may not be easily achieved using purified protein subunit vaccines.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

What is claimed is:

1. An immunogenic composition comprising a live *Salmonella Typhi* vector comprising a cell binding domain of TcdA toxin (CBD/A) of *Clostridium difficile*, a cell binding domain of TcdB toxin (CBD/B) of *Clostridium difficile* and a cell-binding subunit (CdtB) of the *Clostridium difficile* colonization factor binary toxin, wherein at least one of said toxins is inserted into a *Salmonella Typhi* chromosomal locus selected from the group consisting of guaBA and htrA.

2. The immunogenic composition of claim 1, wherein the TcdB toxin (CBD/B) is expressed on a plasmid in *Salmonella Typhi*.

3. The immunogenic composition of claim 2, wherein the plasmid has a non-antibiotic based plasmid selection system.

4. The immunogenic composition of claim 3, wherein the plasmid expresses a gene that is essential for the growth of *Salmonella Typhi* and has been chromosomally mutated in *Salmonella Typhi*.

5. The immunogenic composition of claim 4, wherein the gene encodes single stranded binding protein (SSB).

6. The immunogenic composition of claim 5, wherein the TcdA toxin (CBD/A) and CdtB from binary toxin are chromosomally integrated in *Salmonella Typhi.*

7. The immunogenic composition of claim 6, wherein the TcdA toxin (CBD/A), the TcdB toxin (CBD/B) and CdtB from binary toxin are fused to cytolysin A (ClyA) protein from *Salmonella Typhi* to facilitate export from the cell.

8. The immunogenic composition of claim 7, wherein ClyA has been mutated to reduce hemolytic activity of ClyA and the ClyA mutant is selected from the group consisting of ClyA I198N and ClyA C285W, wherein the isoleucine residue at position 198 and the cysteine residue at position 285 correspond to isoleucine and cysteine residues at those positions in SEQ ID NO: 14.

9. The immunogenic composition of claim 6, wherein the TcdA toxin (CBD/A) and CdtB from binary toxin are inserted into the guaBA locus of *Salmonella Typhi.*

10. The immunogenic composition of claim 6, wherein CdtB from binary toxin is inserted into the htrA locus of *Salmonella Typhi* and the TcdA toxin (CBD/A) is inserted into the guaBA locus of *Salmonella Typhi.*

11. The immunogenic composition of claim 6, wherein one or more nucleic acid sequences encoding the TcdA toxin (CBD/A), the TcdB toxin (CBD/B) or CdtB from binary toxin are codon optimized for expression in *Salmonella Typhi.*

* * * * *